United States Patent [19]
Ishida et al.

[11] Patent Number: 5,861,108
[45] Date of Patent: *Jan. 19, 1999

[54] NAPHTHALENE COMPOUND, AND LIQUID CRYSTAL COMPOSITION AND LIQUID CRYSTAL ELEMENT USING THE SAME

[75] Inventors: Tsutomu Ishida; Atsuo Otsuji; Yoshiyuki Totani, all of Yokohama; Motokazu Hirao, Kabato; Hiroe Kayashima; Masakatsu Nakatsuka, both of Yokohama, all of Japan

[73] Assignee: Mitsui Chemicals, Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 673,093

[22] Filed: Jul. 1, 1996

[30] Foreign Application Priority Data

Jul. 7, 1995 [JP] Japan .................................. 7-171665
Dec. 20, 1995 [JP] Japan .................................. 7-331383

[51] Int. Cl.$^6$ .......................... C09K 19/32; C07C 69/76; C07C 22/00
[52] U.S. Cl. ...................... 252/299.62; 560/100; 570/144
[58] Field of Search ...................... 252/299.62; 560/100; 570/144

[56] References Cited

U.S. PATENT DOCUMENTS 4,680,137  7/1987  Isoyama et al. .................... 252/299.62

(List continued on next page.)

FOREIGN PATENT DOCUMENTS 0458320  11/1991  European Pat. Off. .

(List continued on next page.)

OTHER PUBLICATIONS

Patent Abstracts of Japan, vol. 015, No. 154, (C–0825), Apr. 18, 1991 & JP 03031392 A, (Mitsui Toatsu Chemicals, Inc.), Feb. 12, 1991 *Abstract*.

(List continued on next page.)

*Primary Examiner*—C. H. Kelly
*Attorney, Agent, or Firm*—Burns, Doane, Swecker & Mathis, L.L.P.

[57] ABSTRACT

Provided is a naphthalene compound represented by the following Formula (1):

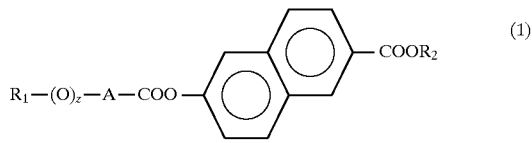

wherein $R_1$ and $R_2$ each represent a linear or branched alkyl group having 1 to 20 carbon atoms, an alkoxyalkyl group having 2 to 20 carbon atoms or an alkenyl group having 2 to 20 carbon atoms which may be substituted with halogen atoms and have no asymmetric carbon atoms; A represents any of the groups represented by the following formulas:

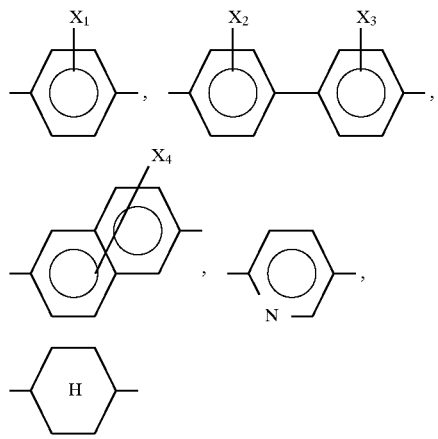

(wherein $X_1$, $X_2$, $X_3$ and $X_4$ each represent a hydrogen atom or a halogen atom); and z represents 0 or 1. The addition of this naphthalene compound to a liquid crystal composition makes it possible to improve various characteristics such as the high speed response property of the liquid crystal composition and the temperature dependency of the response time. The above naphthalene compound is useful as a liquid crystal material for liquid crystal compositions, particularly ferroelectric liquid crystal compositions.

11 Claims, 2 Drawing Sheets

U.S. PATENT DOCUMENTS

| | | | |
|---|---|---|---|
| 4,696,759 | 9/1987 | Isoyama et al. | 252/299.62 |
| 5,082,587 | 1/1992 | Janulis | 252/299.01 |
| 5,190,688 | 3/1993 | Sage et al. | 252/299.01 |
| 5,194,177 | 3/1993 | Nohira et al. | 252/299.61 |
| 5,196,140 | 3/1993 | Poetsch et al. | 252/299.6 |
| 5,246,622 | 9/1993 | Shimizu et al. | 252/299.62 |
| 5,254,747 | 10/1993 | Janulis | 568/650 |
| 5,262,082 | 11/1993 | Janulis et al. | 252/299.01 |
| 5,310,500 | 5/1994 | Aihara et al. | 242/299.62 |
| 5,495,037 | 2/1996 | Hsu et al. | 556/441 |

FOREIGN PATENT DOCUMENTS

| | | |
|---|---|---|
| 0518636 | 12/1992 | European Pat. Off. . |
| 56-107216 | 8/1981 | Japan . |
| 59-118744 | 7/1984 | Japan . |
| 61-195187 | 8/1986 | Japan . |
| 63-246346 | 10/1988 | Japan . |
| 1-193390 | 8/1989 | Japan . |
| 3031392 | 2/1991 | Japan . |
| 3-68686 | 3/1991 | Japan . |
| 3-106850 | 5/1991 | Japan . |

OTHER PUBLICATIONS

Patent Abstracts of Japan, vol. 95, No. 006 & JP 07165672 A (Idemitsu Kosan Co. Ltd.), Jun. 27, 1995, *Abstract*.

N. Clark et al., "Submicrosecond Bistable Electro–Optic Switching In Liquid Crystals", *Appl. Phys. Lett.*, 36(11), 1980, pp. 899–901.

L.A. Beresnev et al, "Ferroelectricity in Titled Smectics Doped With Optically Active Additives", *Mol. Cryst. Liq. Crtst.*, vol.89, 1989, pp. 327–338.

B. Jones, "Apparent Cases of Liquid–Crystal Formation in p–Alkoxybenzoic Acids", *J. Chem. Soc.*, 1935 p. 1874.

Gray et al, "The Preparation of 4–and 5–n–Alkoxy–1–Naphthoic and 6–and 7–n–Alkoxy–2–Naphthoic Acids", *J. Chem. Soc.*, 1954, pp. 678–683.

Gray et al, "Mesomorphism and Chemical Constitution. Part III, The Effect of Halogen Substitutes on the Mesomorphism of the 4–Alkoxybenzoic Acids", *J. Chem. Soc.*, 1954, pp. 2556–2562.

Gray et al, "Mesomorphism and Chemical Constitution, Part V, the Mesomorphic Properties of the 4'–n–Alkoxydiphenyl–4–Carboxylic Acids and Their Simple Alkyl Esters",*J. Chem. Soc.*, 1955, pp. 1412–1420.

Gray et al, "Mesomorphism and Chemical Constitution. Part VIII, The Effect of 3'–Substituents on the Mesomorphism of the 4'–n–Alkoxydiphenyl–4–Carboxylic Acids and Their Simple Alkyl Esters",*J. Chem. Soc.*, 1957, pp. 393–394.

Gray et al, "The Mesomorphic Transition Temperatures of 3'–Substituted 4'–n–Octyloxydiphenyl–4–Carboxylic Acids", *J. Chem. Soc.*, 1959, pp. 1545–1550.

NAPHTHALENE COMPOUND, AND LIQUID CRYSTAL COMPOSITION AND LIQUID CRYSTAL ELEMENT USING THE SAME

BACKGROUND OF THE INVENTION

1. Field of the Invention

The present invention relates to a naphthalene compound, more specifically to a novel naphthalene compound and a naphthalene compound to be useful as an intermediate product for producing said compound and to a liquid crystal composition containing said novel naphthalene compound and a liquid crystal element using the liquid crystal composition.

2. Description of the Related Art

Liquid crystal display elements have so far widely been used for various display elements by making the best use of excellent characteristics thereof such as low voltage actuation, low power consumption, possibility of thin type display, and no fatigue of eyes because of light-receptive display element.

Among them, there have widely been used TN (twisted nematic) type liquid crystal display elements using nematic liquid crystal and STN (super twisted nematic) type liquid crystal display elements having a torsion angle adjusted from 180° to 270°. These display elements are nematic liquid crystal display elements using nematic liquid crystal. These nematic liquid crystal display elements have the defect that they have a long response time and therefore can provide only a response time falling on the order of some ten msec.

A recent progress in industrial techniques has been followed by strong requirement of high speed response to liquid crystal elements, and in order to meet such requirement, various attempts have been made by improving liquid crystal materials. For example, a display device making use of a photoswitching phenomenon of ferroelectric liquid crystal has been proposed [Appl. Phys. Lett., 36, 899 (1980)]. The liquid crystal elements are expected to be applied to not only displays for liquid crystal televisions, etc., but also to materials for optoelectronics-related elements such as optical printer heads, optical Fourier transform elements and light valves.

Ferroelectric liquid crystals belong to tilt series chiral smectic phases in terms of a liquid crystal phase, and among them, liquid crystal phase called a chiral smectic C phase having a low viscosity is preferred from a viewpoint of practical use. Various liquid crystal compounds showing chiral smectic C phases have so far been investigated, and a lot of compounds have already been found and produced. Conditions for using them for ferroelectric liquid crystal elements include:

showing a chiral smectic C phase in a wide temperature range including room temperature, having a suitable phase series on a high temperature part of a chiral smectic C phase and large helical pitches thereof in order to obtain good orientation, having a suitable tilt angle, having a low viscosity, having spontaneous polarization which is large to some extent, and the like.

No single ferroelectric liquid crystal which can satisfy these conditions has ever been known. Accordingly, ferroelectric liquid crystal compositions obtained by blending several liquid crystal compounds or non-liquid crystal compounds have to be used in practical uses.

A ferroelectric liquid crystal composition does not always comprise only ferroelectric liquid crystal compounds, and it is disclosed in, for example, Japanese Patent Application Laid-Open No. 61 195187 (1986) that compositions showing ferroelectric liquid crystal phases as a whole can be obtained by employing compounds or compositions showing non-chiral smectic C, F, G, H and I phases for fundamental materials and blending them with one or plural compounds showing ferroelectric liquid crystal phases. Further, it is reported that ferroelectric liquid crystal compositions can be obtained as a whole by employing compounds or compositions showing phases such as a non-chiral smectic C phase for fundamental materials and blending them with one or plural compounds which are optically active but do not show ferroelectric liquid crystal phases [Mol. Cryst. Liq. Cryst., 89, 327 (1982)].

Phenylpyrimidine series liquid crystal compounds and phenylbenzoate series liquid crystal compounds as shown below have so far been known as typical compounds showing chiral smectic C phases:

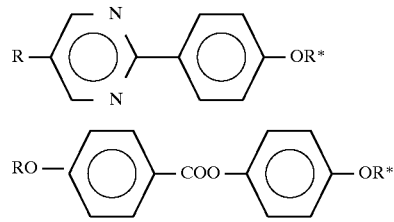

wherein R represents an alkyl group, and R* represents an optically active alkyl group.

Further, naphthalene series liquid crystal compounds as shown below are proposed in Japanese Patent Application Laid-open No. 63-246346 (1988), Japanese Patent Application Laid-open No. 1-193390 (1989), Japanese Patent Application Laid-open No. 3-68686 (1991) and Japanese Patent Application Laid-open No. 3-106850 (1991):

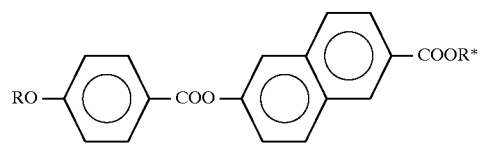

wherein R represents an alkyl group, and R* represents an optically active alkyl group.

However, ferroelectric liquid crystal compositions using the phenylpyrimidine series liquid crystal compounds or phenylbenzoate series liquid crystal compounds described above have had the problems that they are liable to cause orientation unevenness so as to bring about defects when they are put into liquid crystal cells and that the good memory property can not be obtained and the contrast ratio is low. Meanwhile, ferroelectric liquid crystal compositions comprising the naphthalene series compounds described above show good orientation when liquid crystal cells are charged with them, and can provide a good memory property without having defects. However, it is not reasonable to say that they have sufficiently satisfactory characteristics in terms of high speed response and temperature dependency of a response time.

SUMMARY OF THE INVENTION

The present invention provides a liquid crystal compound suited to improve such various characteristics as high speed response, orientation and high contrast ratio when the liquid crystal compound is blended into a ferroelectric liquid crystal composition in order to put a ferroelectric liquid crystal element into practical use, a compound useful as a component for a liquid crystal composition, an intermediate product for producing the above compound and a liquid crystal composition containing the above compound, and a liquid crystal element using said liquid crystal composition.

First, the present invention relates to a naphthalene compound represented by the following Formula (1):

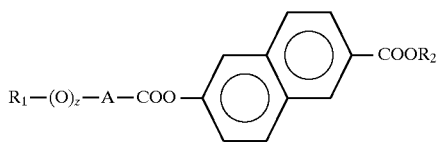

wherein $R_1$ and $R_2$ each represent a linear or branched alkyl group having 1 to 20 carbon atoms, an alkoxyalkyl group having 2 to 20 carbon atoms or an alkenyl group having 2 to 20 carbon atoms which may be substituted with halogen atoms and have no asymmetric carbon atoms; A represents any of the groups represented by the following formulas:

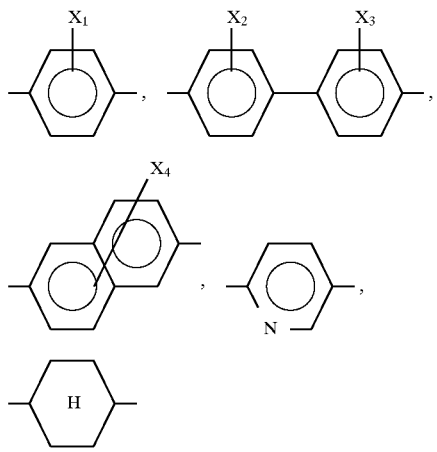

(wherein $X_1$, $X_2$, $X_3$ and $X_4$ each represent a hydrogen atom or a halogen atom, and 1,4-cyclohexylene ring is disposed in a trans position); and z represents 0 or 1.

Further, the present invention relates to a naphthalene compound represented by the following Formula (2) which is useful as an intermediate product when producing the naphthalene compound represented by Formula (1):

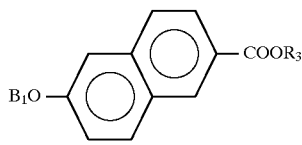

wherein $R_3$ represents a branched alkyl group having no asymmetric carbon atoms and having 3 to 20 carbon atoms, or a linear or branched alkyl group having 1 to 20 carbon atoms, an alkoxyalkyl group having 2 to 20 carbon atoms or an alkenyl group having 2 to 20 carbon atoms which are substituted with halogen atoms and have no asymmetric carbon atoms; and $B_1$ represents a hydrogen atom or a benzyl group.

Furthermore, the present invention relates to a liquid crystal composition using the compound represented by Formula (1), and a liquid crystal element using said liquid crystal composition.

The liquid crystal composition using the naphthalene compound of the present invention is improved in various characteristics such as high speed response, temperature dependency of a response time, etc.

DETAILED DESCRIPTION OF THE PREFERRED EMBODIMENTS

Figure 1:
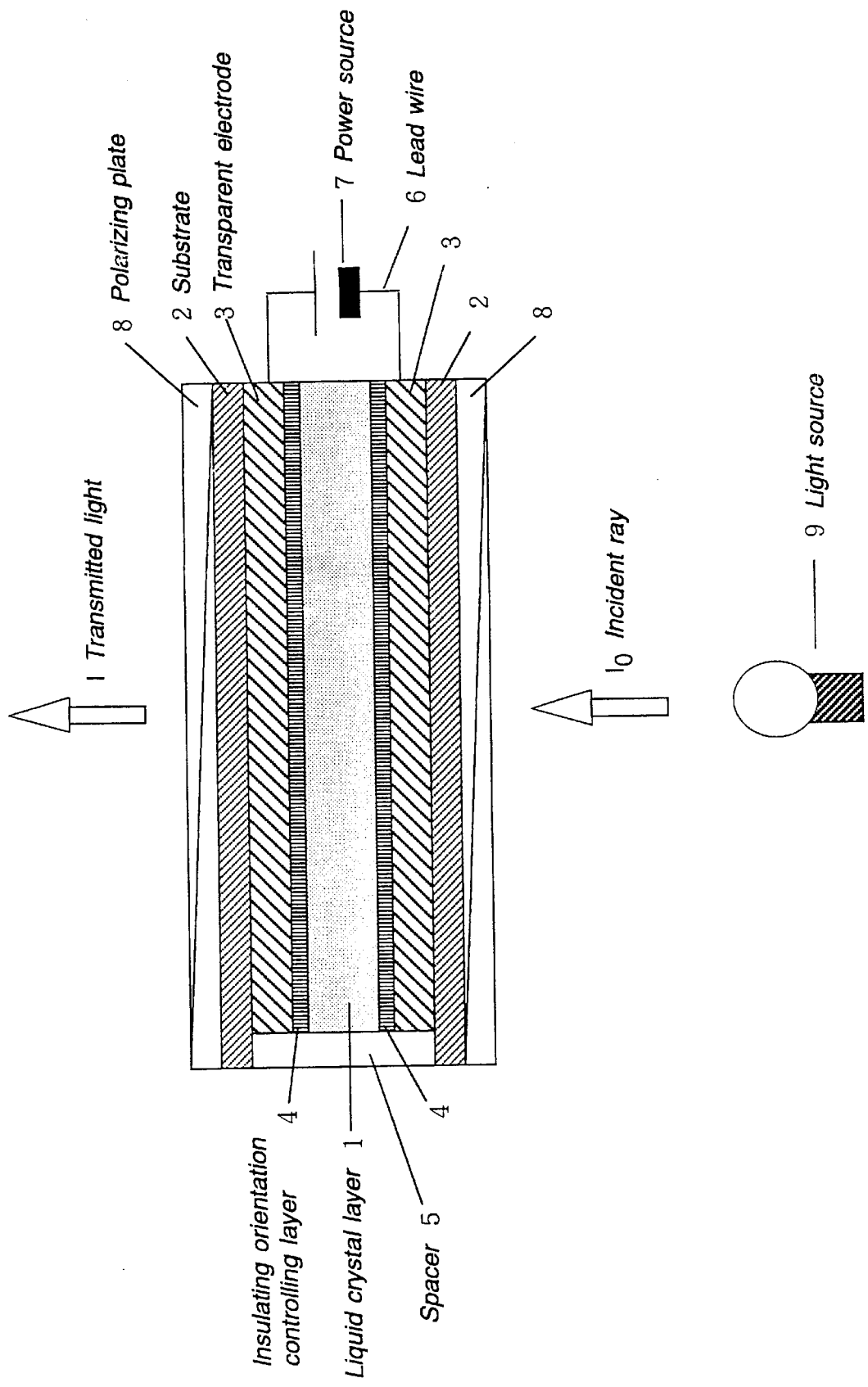
FIG. 1 is a schematic, cross-sectional view of one example of a liquid crystal element using a liquid crystal showing a chiral smectic phase.

The present invention will be explained below in detail.

The naphthalene compound of the present invention represented by Formula (1) is a novel compound.

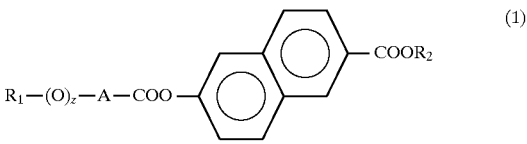

In Formula (1), $R_1$ and $R_2$ each represent a linear or branched alkyl group having 1 to 20 carbon atoms, an alkoxyalkyl group having 2 to 20 carbon atoms or an alkenyl group having 2 to 20 carbon atoms which may be substituted with halogen atoms and have no asymmetric carbon atoms. More preferably, $R_1$ and $R_2$ each represent a linear or branched alkyl group represented by Formulas (I) and (II):

$$-C_aH_{2a+1}(n) \qquad (I)$$

$$-(CH_2)_bCH(C_cH_{2c+1})_2 \qquad (II)$$

wherein a represents a natural number of 1 to 20; b represents a natural number of 0 to 17; and c represents a natural number of 1 to 9, provided that $b+c\times2\leq19$, an alkoxyalkyl group represented by Formula (III):

$$-C_dH_{2d}O(C_eH_{2e}O)_fC_gH_{2g+1} \qquad (III)$$

wherein d represents a natural number of 1 to 10; e represents a natural number of 1 to 10; f represents a natural number of 0 to 5; and g represents a natural number of 1 to 12, provided that $d+e\times f+g\leq20$, or a halogenated alkyl group represented by Formula (IV), (V) or (VI):

$$-(CH_2)_h(CX_2)_iH \qquad (IV)$$

$$-(CH_2)_j(C_kX_{2k})_lC_mH_{2m+1} \qquad (V)$$

$$-(CH_2)_n(CX_2)_pX \qquad (VI)$$

wherein X represents a halogen atom; h represents a natural number of 0 to 19; i represents a natural number of 1 to 20; j represents a natural number of 0 to 18; k represents a natural number of 1 to 10; l represents a natural number of 1 to 19; and m represents a natural number of 1 to 19; n represents a natural number of 0 to 19; p represents a natural number of 1 to 20, provided that $h+i\leq20$, $j+k\times l+m\leq20$ and $n+p\leq20$.

More preferably, $R_1$ and $R_2$ each represent the group represented by Formula (I), (II), (III), (IV) or (VI).

Further preferably, $R_1$ represents the group represented by Formula (I), (III), (IV) or (VI).

The concrete examples of the groups represented by $R_1$ and $R_2$ include linear alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl and n-eicocyl, branched alkyl groups such as 1-methylethyl, 2-methylpropyl, 3-methylbutyl, 4-methylpentyl, 5-methylhexyl, 6-methylheptyl, 7-methyloctyl, 8-methylnonyl, 9-methyldecyl, 11-methyldodecyl, 3-pentyl, 2-ethylbutyl, 3-ethylpentyl, 4-ethylhexyl, 5-ethylheptyl, 6-ethyloctyl, 4-heptyl, 2-n-propylpentyl, 3-n-propylhexyl, 4-n-propylheptyl, 5-n-propyloctyl, 6-n-propylnonyl, 7-n-propyldecyl, 8-n-propylundecyl, 9-n-propyldodecyl, 1-n-butylpentyl, 2-n-butylhexyl, 3-n-butylheptyl, 4-n-butyloctyl, 5-n-butylnonyl, 6-n-butyldecyl, 7-n-butylundecyl, 8-n-butyldodecyl, 2-n-pentylheptyl, 3-n-pentyloctyl, 5-n-pentyldecyl, 3-n-hexylnonyl, 4-n-hexyldecyl, 6-n-hexyldodecyl, 2,2-dimethylpropyl, 2,2-dimethylbutyl, 3,3-dimethylbutyl, 3,3-dimethylpentyl, 4,4-dimethylpentyl, 5,5-dimethylhexyl, 6,6-dimethylheptyl, 3,3-diethylpentyl and 2,2,4,4-tetramethylpentyl, halogenated alkyl groups such as fluoromethyl, difluoromethyl, 2-fluoroethyl, 3-fluoro-n-propyl, 4-fluoron-n-butyl, 5-fluoro-n-pentyl, 6-fluoro-n-hexyl, 2-chloroethyl, 3-chloro-n-propyl, 4-chloro-n-butyl, 5-chloro-n-pentyl, trifluoromethyl, perfluoroethyl, perfluoro-n-propyl, perfluoroisopropyl, perfluoro-n-butyl, perfluoroisobutyl, perfluoro-n-pentyl, perfluoroisopentyl, perfluoro-n-hexyl, perfluoro-n-heptyl, perfluoro-n-octyl, perfluoro-n-nonyl, perfluoro-n-decyl, perfluoro-n-undecyl, perfluoro-n-dodecyl, perfluoro-n-tetradecyl, 1-hydroperfluoroisopropyl, 1,1-dihydroperfluoroethyl, 1,1-dihydroperfluoro-n-propyl, 1,1-dihydroperfluoro-n-butyl, 1,1-dihydroperfluoroisobutyl, 1,1-dihydroperfluoro-n-pentyl, 1,1-dihydroperfluoro-n-hexyl, 1,1-dihydroperfluoro-n-heptyl, 1,1-dihydroperfluoron-n-octyl, 1,1-dihydroperfluoro-n-nonyl, 1,1-dihydroperfluoron-n-decyl, 1,1-dihydroperfluoro-n-undecyl, 1,1-dihydroperfluoro-n-dodecyl, 1,1-dihydroperfluoro-n-tetradecyl, 1,1-dihydroperfluoro-n-pentadecyl, 1,1-dihydroperfluoro-n-hexadecyl, 1,1,2-trihydroperfluoroethyl, 1,1,3-trihydroperfluoro-n-propyl, 1,1,4-trihydroperfluoro-n-butyl, 1,1,5-trihydroperfluoro-n-pentyl, 1,1,6-trihydroperfluoro-n-hexyl, 1,1,7-trihydroperfluoro-n-heptyl, 1,1,8-trihydroperfluoro-n-octyl, 1,1,9-trihydroperfluoro-n-nonyl, 1,1,11-trihydroperfluoro-n-undecyl, 2-(perfluoroethyl)ethyl, 2-(perfluoro-n-propyl)ethyl, 2-(perfluoro-n-butyl)ethyl, 2-(perfluoro-n-pentyl)ethyl, 2-(perfluoro-3-methylbutyl)ethyl, 2-(perfluoro-n-hexyl)ethyl, 2-(perfluoro-n-heptyl)ethyl, 2-(perfluoro-5-methylhexyl)ethyl, 2-(perfluoro-n-octyl)ethyl, 2-(perfluoro-7-methyloctyl)ethyl, 2-(perfluoro-n-decyl)ethyl, 2-(perfluoro-n-nonyl)ethyl, 2-(perfluoro-9-methyldecyl)ethyl, 2-(perfluoro-n-dodecyl)ethyl, 2,2-bis(trifluoromethyl)propyl, 3-(perfluoro-n-propyl)-n-propyl, 3-(perfluoro-n-butyl)-n-propyl, 3-(perfluoro-n-hexyl)-n-propyl, 3-(perfluoro-n-heptyl)-n-propyl, 3-(perfluoro-n-octyl)-n-propyl, 3-(perfluoro-n-decyl)-n-propyl, 3-(perfluoro-n-dodecyl)-n-propyl, 4-(perfluoroethyl)-n-butyl, 4-(perfluoro-n-propyl)n-butyl, 4-(perfluoro-n-butyl)-n-butyl, 4-(perfluoro-n-pentyl)-n-butyl, 4-(perfluoro-n-hexyl)-n-butyl, 4-(perfluoro-n-heptyl)-n-butyl, 4-(perfluoro-n-octyl)-n-butyl, 4-(perfluoro-n-decyl)-n-butyl, 5-(perfluoro-n-propyl)-n-pentyl, 5-(perfluoro-n-butyl)-n-pentyl, 5-(perfluoro-npentyl)-n-pentyl, 5-(perfluoro-n-hexyl)-n-pentyl, 5-(perfluoro-n-heptyl)-n-pentyl, 5-(perfluoro-n-octyl)-n-pentyl, 6-(perfluoroethyl)-n-hexyl, 6-(perfluoro-n-propyl)-n-hexyl, 6-(perfluoro-1-methylethyl)-n-hexyl, 6-(perfluoro-n-butyl)-n-hexyl, 6-(perfluoro-n-hexyl)-n-hexyl, 6-(perfluoro-n-heptyl)-n-hexyl, 6-(perfluoro-5-methylhexyl)-nhexyl, 6-(perfluoro-n-octyl)-n-hexyl, 6-(perfluoro-7-methyloctyl)-n-hexyl, 7-(perfluoroethyl)-n-heptyl, 7-(perfluoro-n-propyl)-n-heptyl, 7-(perfluoro-n-butyl)-n-heptyl and 7-(perfluoro-n-pentyl)-n-heptyl, alkoxyalkyl groups such as methoxymethyl, 2-methoxyethyl, 3-methoxypropyl, 4-methoxybutyl, 5-methoxypentyl, 6-methoxyhexyl, 7-methoxyheptyl, 8-methoxyoctyl, 9-methoxynonyl, 10-methoxydecyl, ethoxymethyl, 2-ethoxyethyl, 3-ethoxypropyl, 4-ethoxybutyl, 5-ethoxypentyl, 6-ethoxyhexyl, 7-ethoxyheptyl, 8-ethoxyoctyl, 9-ethoxynonyl, 10-ethoxydecyl, n-propoxymethyl, 2-n-propoxyethyl, 3-n-propoxypropyl, 4-n-propoxybutyl, 5-n-propoxypentyl, 6-n-propoxyhexyl, 7-n-propoxyheptyl, 8-n-propoxyoctyl, 9-n-propoxynonyl, 10-n-propoxydecyl, n-butoxymethyl, 2-n-butoxyethyl, 3-n-butoxypropyl, 4-n-butoxybutyl, 5-n-butoxypentyl, 6-n-butoxyhexyl, 7-n-butoxyheptyl, 8-n-butoxyoctyl, 9-n-butoxynonyl, 10-n-butoxydecyl, n-pentyloxymethyl, 2-n-pentyloxyethyl, 3-n-pentyloxypropyl, 4-n-pentyloxybutyl, 5-n-pentyloxypentyl, 6-n-pentyloxyhexyl, 7-n-pentyloxyheptyl, 8-n-pentyloxyoctyl, 9-n-pentyloxynonyl, 10-n-pentyloxydecyl, n-hexyloxymethyl, 2-n-hexyloxyethyl, 3-n-hexyloxypropyl, 4-n-hexyloxybutyl, 5-n-hexyloxypentyl, 6-n-hexyloxyhexyl, 7-n-hexyloxyheptyl, 8-n-hexyloxyoctyl, 9-n-hexyloxynonyl, 10-n-hexyloxydecyl, n-heptyloxymethyl, 2-n-heptyloxyethyl, 3-n-heptyloxypropyl, 4-n-heptyloxybutyl, 5-n-heptyloxypentyl, 6-n-heptyloxyhexyl, 7-n-heptyloxyheptyl, 8-n-heptyloxyoctyl, 9-n-heptyloxynonyl, 10-n-heptyloxydecyl, n-octyloxymethyl, 2-n-octyloxyethyl, 3-n-octyloxypropyl, 4-n-octyloxybutyl, 5-n-octyloxypentyl, 6-n-octyloxyhexyl, 7-n-octyloxyheptyl, 8-n-octyloxyoctyl, 9-n-octyloxynonyl, 10-n-octyloxydecyl, n-nonyloxymethyl, 2-n-nonyloxyethyl, 3-n-nonyloxypropyl, 4-n-nonyloxybutyl, 5-n-nonyloxypentyl, 6-n-nonyloxyhexyl, 7-n-nonyloxyheptyl, 8-n-nonyloxyoctyl, 9-n-nonyloxynonyl, 10-n-nonyloxydecyl, n-decyloxymethyl, 2-n-decyloxyethyl, 3-n-decyloxypropyl, 4-n-decyloxybutyl, 5-n-decyloxypentyl, 6-n-decyloxyhexyl, 7-n-decyloxyheptyl, 8-n-decyloxyoctyl, 9-n-decyloxynonyl, 2-n-undecyloxyethyl, 4-n-undecyloxybutyl, 6-n-undecyloxyhexyl, 8-n-undecyloxyoctyl, 2-n-dodecyloxyethyl, 4-n-dodecyloxybutyl, 6-n-dodecyloxyhexyl, isopropoxymethyl, 2-isopropoxyethyl, 3-isopropoxypropyl, 4-isopropoxybutyl, 5-isopropoxypentyl, 6-isopropoxyhexyl, 7-isopropoxyheptyl, 8-isopropoxyoctyl, 9-isopropoxynonyl, 10-isopropoxydecyl, isobutoxymethyl, 2-isobutoxyethyl, 3-isobutoxypropyl, 4-isobutoxybutyl, 5-isobutoxypentyl, 6-isobuyoxyhexyl, 7-isobutoxyheptyl, 8-isobutoxyoctyl, 9-isobutoxynonyl, 10-isobutoxydecyl, tert-butoxymethyl, 2-tert-butoxyethyl, 3-tert-butoxypropyl, 4-tert-butoxybutyl, 5-tert-butoxypentyl, 6-tert-butoxyhexyl, 7-tert-butoxyheptyl, 8-tert-butoxyoctyl, 9-tert-butoxynonyl, 10-tert-butoxydecyl, (2-ethylbutoxy)methyl, 2-(2'-ethylbutoxy)ethyl, 3-(2'-ethylbutoxy)propyl, 4-(2'-ethylbutoxy)butyl, 5-(2'-ethylbutoxy)pentyl, 6-(2'-ethylbutoxy)hexyl, 7-(2'-ethylbutoxy)heptyl, 8-(2'-ethylbutoxy)octyl, 9-(2'-ethylbutoxy)nonyl, 10-(2'-ethylbutoxy)decyl, (3-ethylpentyloxy)methyl, 2-(3'-ethylpentyloxy)ethyl, 3-(3'-ethylpentyloxy)propyl, 4-(3'-ethylpentyloxy)butyl, 5-(3'-ethylpentyloxy)pentyl, 6-(3'-ethylpentyloxy)hexyl, 7-(3'-ethylpentyloxy)heptyl, 8-(3'-ethylpentyloxy)octyl, 9-(3'-ethylpentyloxy)nonyl, 10-(3'- ethylpentyloxy)decyl, 2-(2'-methoxyethoxy)ethyl, 2-(2'-ethoxyethoxy)ethyl, 2-(2'-n-propoxyethoxy)ethyl, 2-(2'-isopropoxyethoxy)ethyl, 2-(2'-n-butoxyethoxy)ethyl, 2-(2'-isobutoxyethoxy)ethyl, 2-(2'-tert-butoxyethoxy)ethyl, 2-(2'-n-pentyloxyethoxy)ethyl, 2-[2'-(2"-ethylbutoxy)ethoxy]ethyl, 2-(2'-n-hexyloxyethoxy)ethyl, 2-[2'-(3"-ethylpentyloxy)ethoxy]ethyl, 2-(2'-n-heptyloxyethoxy)ethyl, 2-(2'-n-octyloxyethoxy)ethyl, 2-(2'-n-nonyloxyethoxy)ethyl, 2-(2'-n-decyloxyethoxy)ethyl, 2-(2'-n-undecyloxyethoxy)ethyl, 2-(2'-n-dodecyloxyethoxy)ethyl, 2-[2'-(2"-methoxyethoxy)ethoxy]ethyl, 2-[2'-(2"-ethoxyethoxy)ethoxy]ethyl, 2-[2'(2"-n-propoxyethoxy)ethoxy]ethyl, 2-[2'-(2"-isopropoxyethoxy)ethoxy]ethyl, 2-[2'-(2"-n-butoxyethoxy)ethoxy]ethyl, 2-[2'-(2"-isobutoxyethoxy)ethoxy]ethyl, 2-[2'-(2"-tert-butoxyethoxy)ethoxy]ethyl, 2-{2'-[2"-(2"'-ethylbutoxy)ethoxy]ethoxy}ethyl, 2-[2'-(2"-n-pentyloxyethoxy)ethoxy]ethyl, 2-[2'-(2"-n-hexyloxyethoxy)ethoxy]ethyl,2-{2'-[2"-(3"'-ethylpentyloxy)ethoxy]ethoxy}ethyl, 2-[2'-(2"-n-heptyloxyethoxy)ethoxy]ethyl, 2-[2'-(2"-n-octyloxyethoxy)ethoxy]ethyl,2-[2'-(2"-n-nonyloxyethoxy)ethoxy]ethyl, 2-[2'-(2"-n-decyloxyethoxy)ethoxy]ethyl, 2-[2'-(2"-n-undecyloxyethoxy)ethoxy]ethyl, 2-{2'-[2"-(2"'-methoxyethoxy)ethoxy]ethoxy}ethyl, 2-{2'-{2"-[2"'-(2-methoxyethoxy)ethoxy]ethoxy}ethoxy}ethyl, 2-{2'-{2"-{2"'-[2-(2-methoxyethoxy)ethoxy]ethoxy}ethoxy}ethoxy}ethyl, (2-ethoxyethoxy)methyl, (2-n-butoxyethoxy)methyl, (2-n-hexyloxyethoxy)methyl, (3-ethoxypropoxy)methyl, (3-n-propoxypropoxy)methyl, (3-n-pentyloxypropoxy)methyl, (3-n-hexyloxypropoxy)methyl, (4-methoxybutoxy)methyl, (4-ethoxybutoxy)methyl, (4-n-butoxybutoxy)methyl, 2-(3'-methoxypropoxy)ethyl, 2-(3'-ethoxypropoxy)ethyl, 2-(4'-methoxybutoxy)ethyl, 2-(4'-ethoxybutoxy)ethyl, 2-[4'-(2"-ethylbutoxy)butoxy]ethyl, 2-[4'-(3"-ethylpentyloxy)butoxy]ethyl, 3-(2'-methoxyethoxy)propyl, 3-(2'-ethoxyethoxy)propyl, 3-(2'-n-pentyloxyethoxy)propyl, 3-(2'-n-hexyloxyethoxy)propyl, 3-(3'-ethoxypropoxy)propyl, 3-(3'-n-propoxypropoxy)propyl, 3-(3'-n-butoxypropoxy)propyl, 3-(4'-ethoxybutoxy)propyl, 3-(5'-ethoxypentyloxy)propyl, 4-(2'-methoxyethoxy)butyl, 4-(2'-ethoxyethoxy)butyl, 4-(2'-isopropoxyethoxy)butyl, 4-(2'-isobutoxyethoxy)butyl, 4-(2'-n-butoxyethoxy)butyl, 4-(2'-n-hexyloxyethoxy)butyl, 4-(3'-n-propoxypropoxy)butyl, 4-[2'-(2"-methoxyethoxy)ethoxy]butyl, 4-[2'-(2"-n-butoxyethoxy)ethoxy]butyl and 4-[2'-(2"-n-hexyloxyethoxy)ethoxy]butyl, halogenated alkoxyalkyl groups such as 2-(2'-fluoroethoxy)ethyl, 4-(2'-fluoroethoxy)butyl, 6-(2'-fluoroethoxy)hexyl, 8-(2'-fluoroethoxy)octyl, 2-(3'-fluoro-n-propoxy)ethyl, 4-(3'-fluoro-n-propoxy)butyl, 6-(3'-fluoro-n-propoxy)hexyl, 8-(3'-fluoro-n-propoxy)octyl, 2-(4'-fluoro-n-butoxy)ethyl, 4-(4'-fluoro-n-butoxy)butyl, 6-(4'-fluoro-n-butoxy)hexyl, 8-(4'-fluoro-n-butoxy)octyl, 2-(2'-chloroethoxy)ethyl, 4-(2'-chloroethoxy)butyl, 6-(2'-chloroethoxy)hexyl, 8-(2'-chloroethoxy)octyl, 2-(3'-chloro-n-propoxy)ethyl, 4-(3'-chloro-n-propoxy)butyl, 6-(3'-chloro-n-propoxy)hexyl, 8-(3'-chloro-n-propoxy)octyl, 2-(4'-chloro-n-butoxy)ethyl, 4-(4'-chloro-n-butoxy)butyl, 6-(4'-chloro-n-butoxy)hexyl and 8-(4'-chloro-n-butoxy)octyl, and alkenyl groups such as vinyl, propenyl, 2-butenyl, 3-butenyl, 3-hexenyl, 5-hexenyl, 2-octenyl, 3-octenyl, 7-octenyl, 2-nonenyl, 3-nonenyl, 6-nonenyl, 8-nonenyl, 2-decenyl, 3-decenyl, 9-decenyl, 2-undecenyl, 3-undecenyl, 10-undecenyl, 2-dodecenyl, 3-dodecenyl, and 11-dodecenyl.

In Formula (1), A represents any of the groups represented by the following formulas:

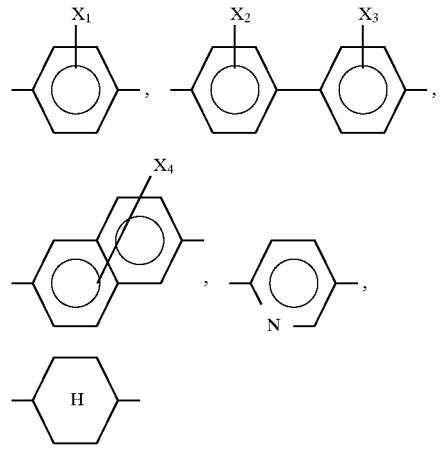

preferably any of the groups represented by the following formulas:

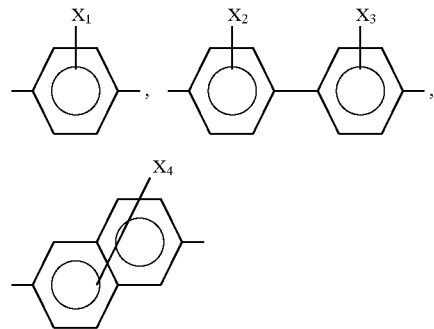

In A, $X_1$, $X_2$, $X_3$ and $X_4$ each represent a hydrogen atom or a halogen atom, preferably a hydrogen atom, a fluorine atom, a chlorine atom or a bromine atom, more preferably a hydrogen atom, a fluorine atom or a chlorine atom, and further preferably a hydrogen atom or a fluorine atom.

The substitution position of $X_1$ or $X_2$ is ortho positions or meta positions to the substituent $R_1$— or $R_1O$—, preferably an ortho position. The substitution position of $X_3$ is an ortho position or a meta position to a —COO— group, preferably an ortho position.

The substitution position of $X_4$ is an α-position or β-position on the naphthalene ring, preferably an ortho position to the substituent $R_1$— or $R_1O$— and/or a —COO— group, more preferably an ortho position to the substituent $R_1$— or $R_1O$— and/or a —COO— group, and an α-position on the naphthalene ring.

In Formula (1), z represents 0 or 1.

The naphthalene compounds represented by Formula (1) of the present invention are classified broadly into five kinds of the following structures (1-1) to (1-5):

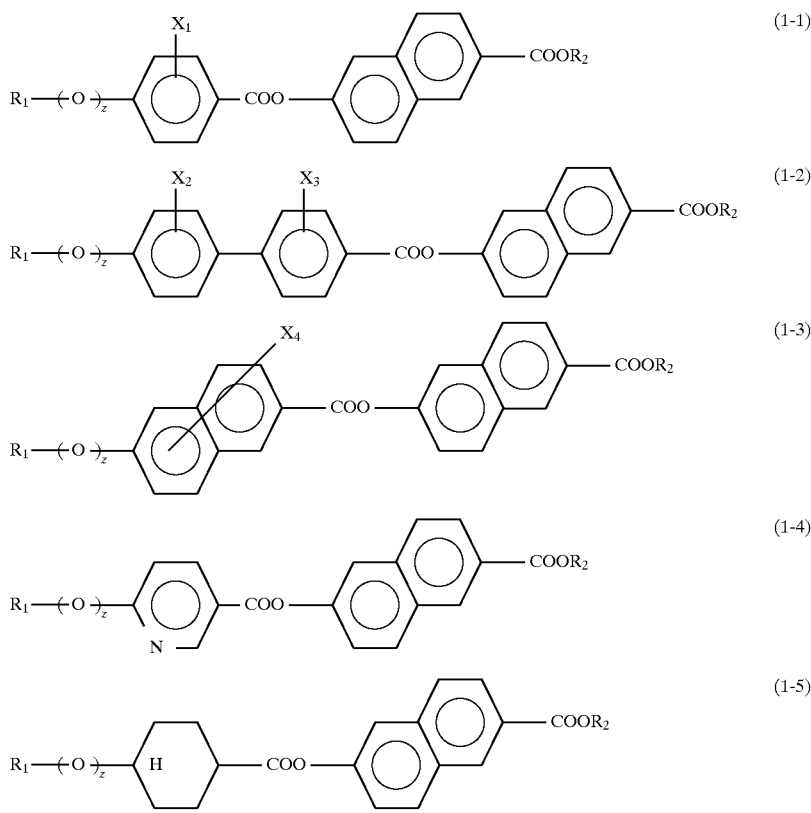
The compounds having the structures shown below can be given as the concrete examples of the naphthalene compound represented by Formula (1):
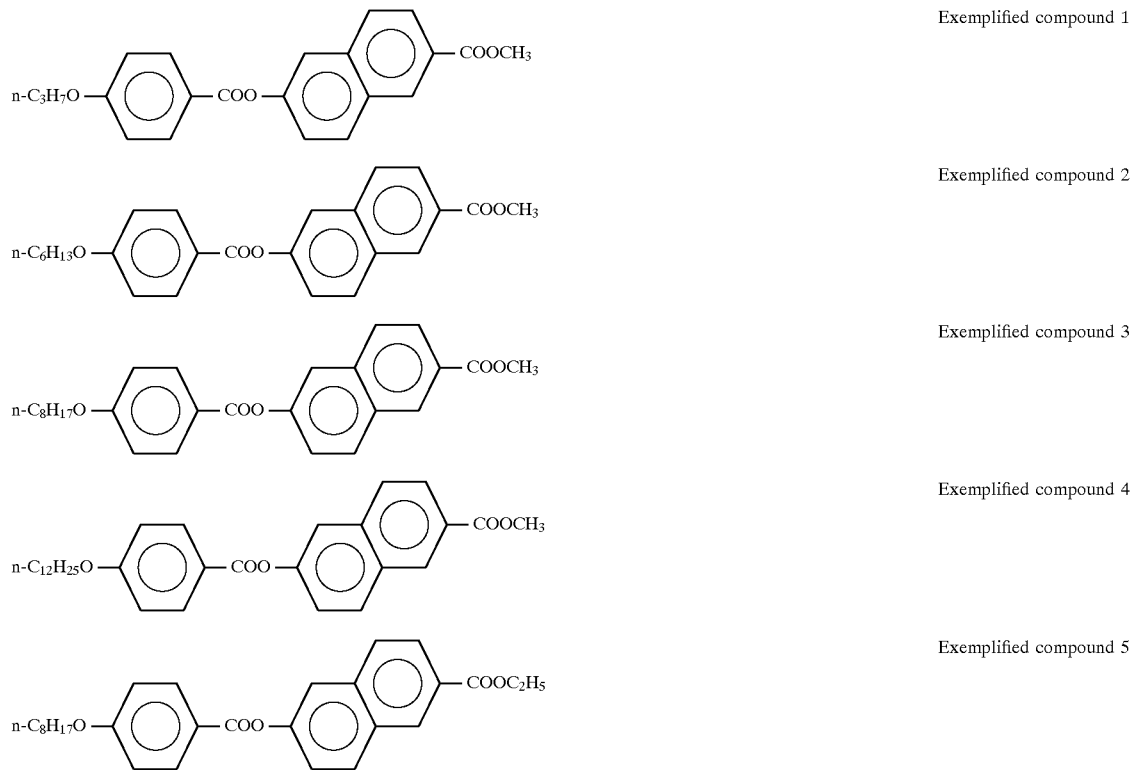

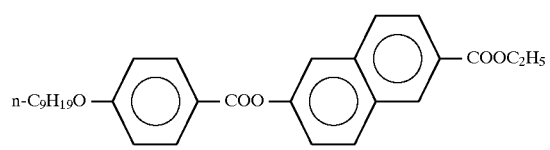
Exemplified compound 6
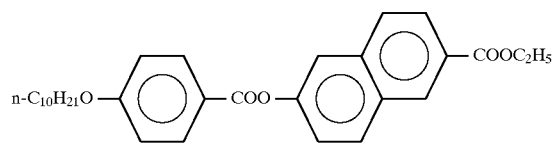
Exemplified compound 7
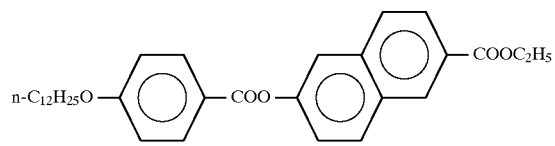
Exemplified compound 8
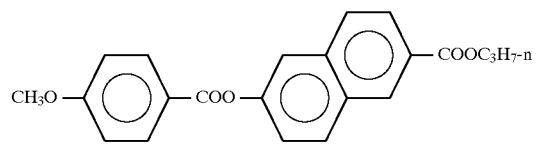
Exemplified compound 9
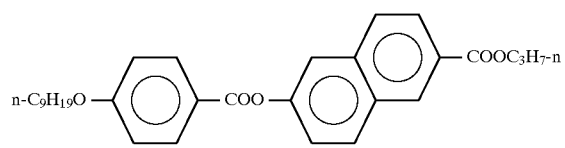
Exemplified compound 10
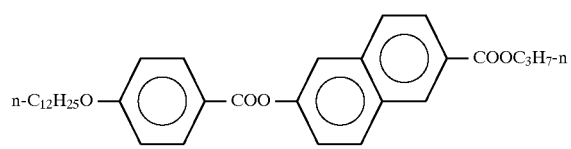
Exemplified compound 11
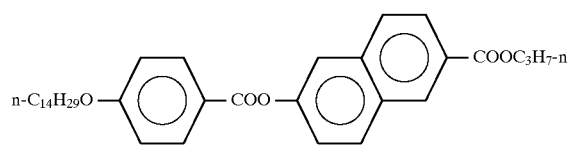
Exemplified compound 12
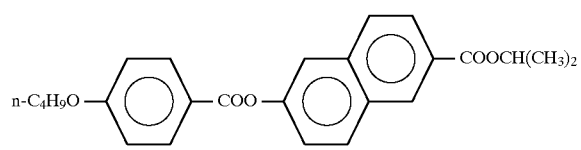
Exemplified compound 13
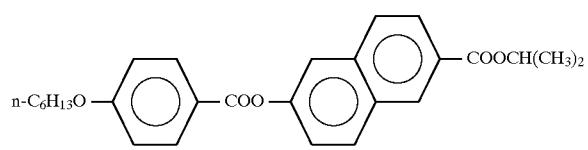
Exemplified compound 14
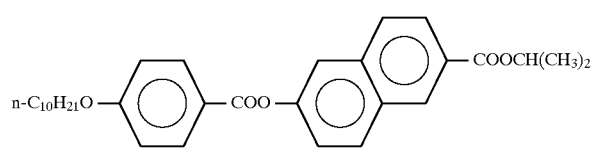
Exemplified compound 15
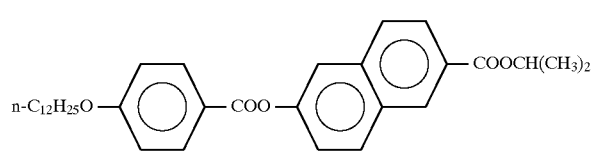
Exemplified compound 16

-continued
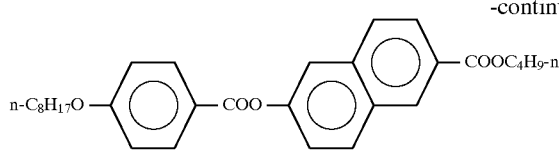
Exemplified compound 17
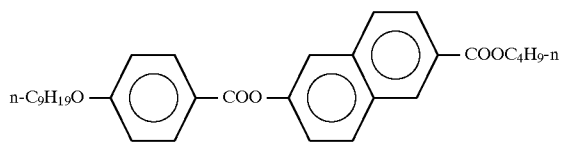
Exemplified compound 18
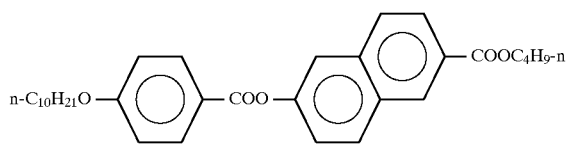
Exemplified compound 19
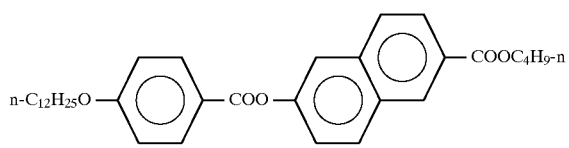
Exemplified compound 20
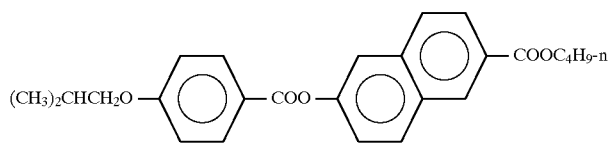
Exemplified compound 21
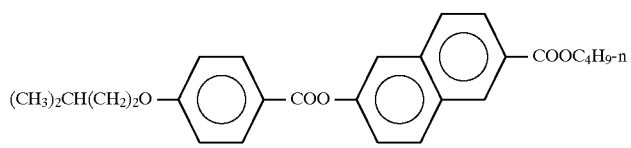
Exemplified compound 22
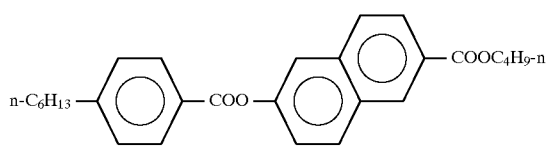
Exemplified compound 23
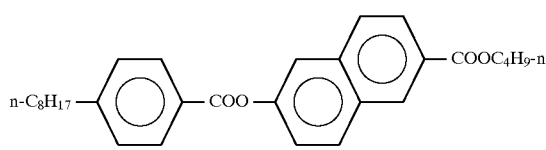
Exemplified compound 24
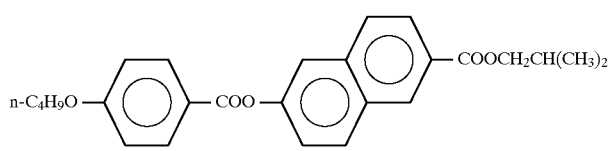
Exemplified compound 25
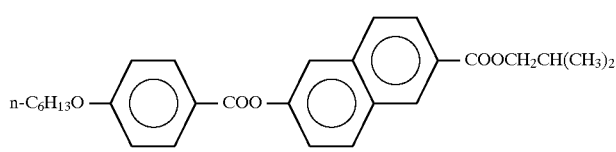
Exemplified compound 26
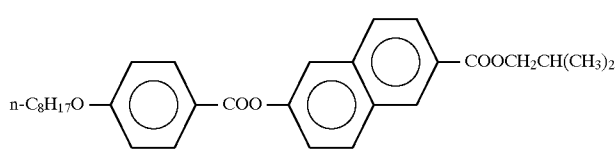
Exemplified compound 27

-continued
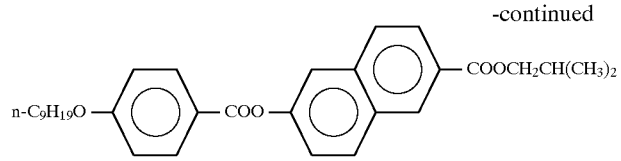
Exemplified compound 28
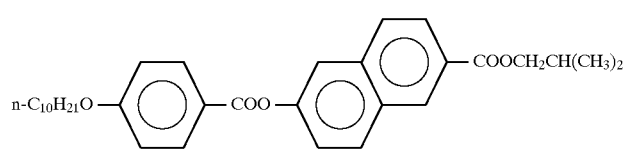
Exemplified compound 29
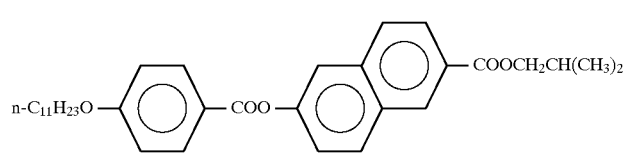
Exemplified compound 30
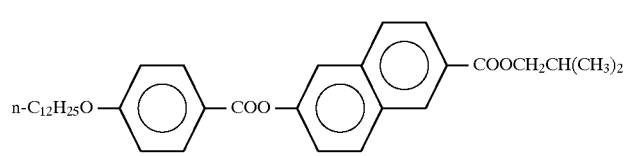
Exemplified compound 31
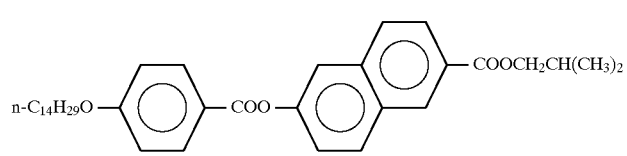
Exemplified compound 32
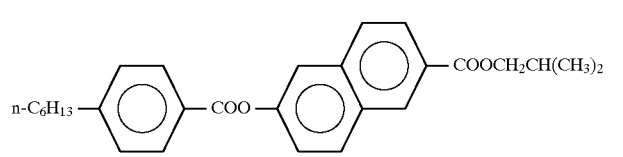
Exemplified compound 33
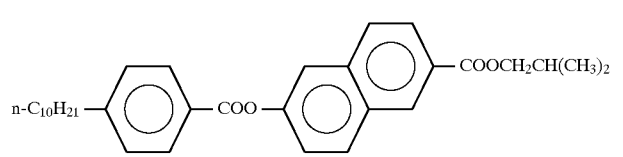
Exemplified compound 34
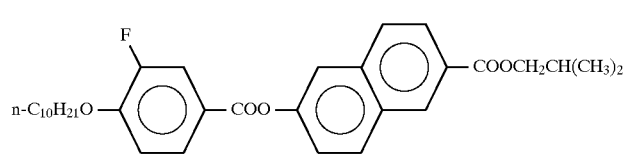
Exemplified compound 35
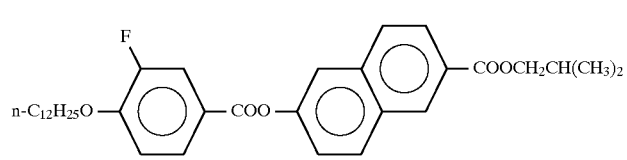
Exemplified compound 36
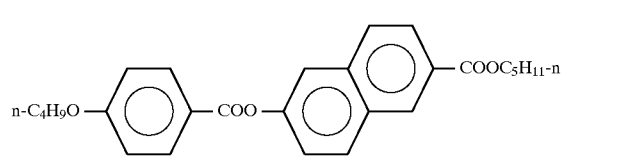
Exemplified compound 37
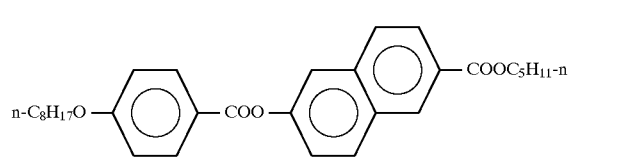
Exemplified compound 38

-continued
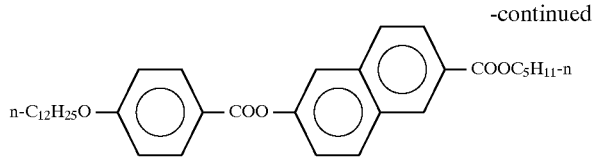
Exemplified compound 39
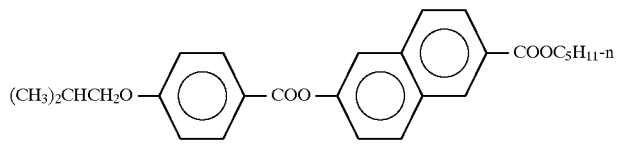
Exemplified compound 40
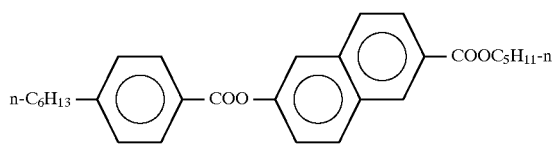
Exemplified compound 41
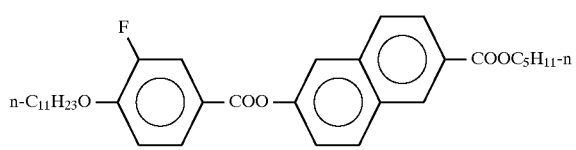
Exemplified compound 42
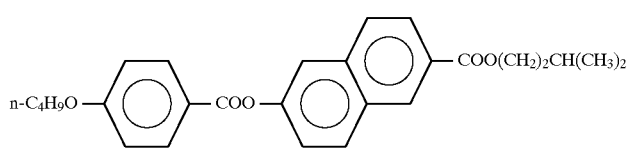
Exemplified compound 43
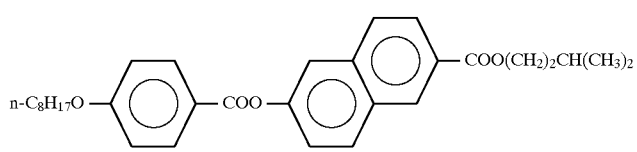
Exemplified compound 44
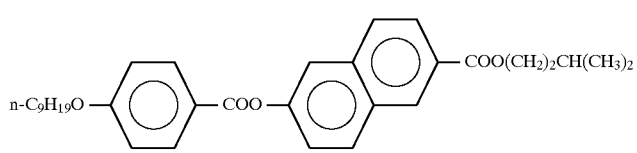
Exemplified compound 45
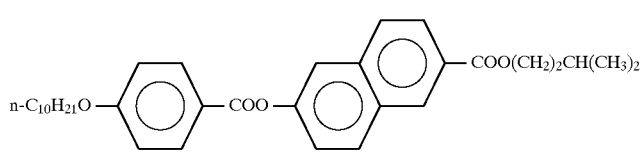
Exemplified compound 46
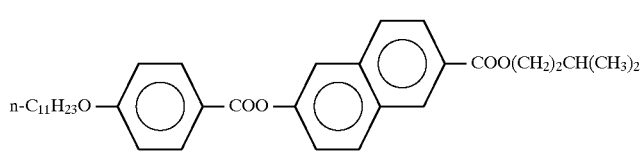
Exemplified compound 47
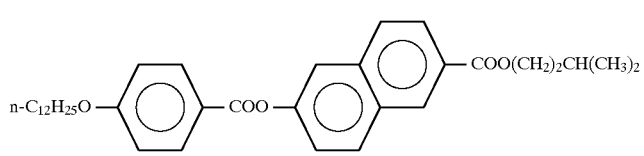
Exemplified compound 48
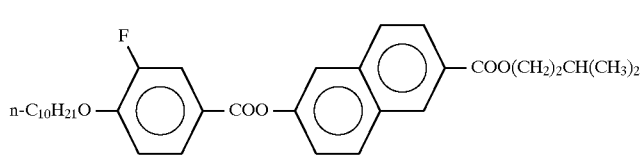
Exemplified compound 49

-continued
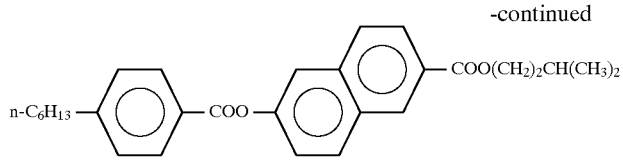
Exemplified compound 50
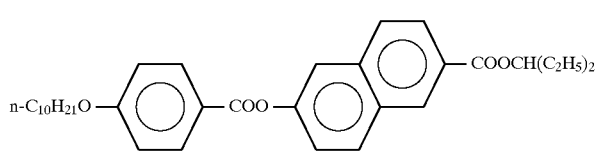
Exemplified compound 51
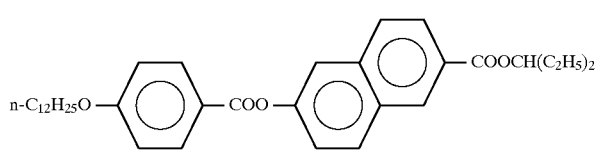
Exemplified compound 52
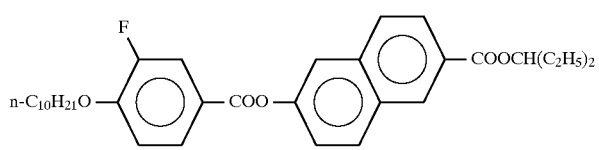
Exemplified compound 53
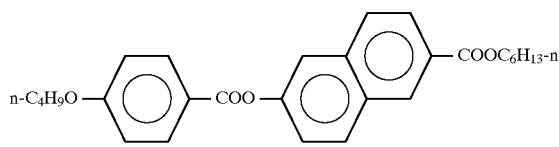
Exemplified compound 54
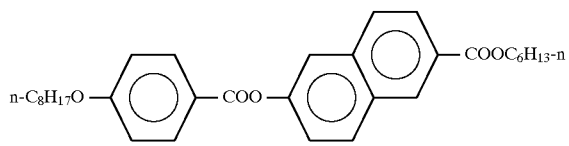
Exemplified compound 55
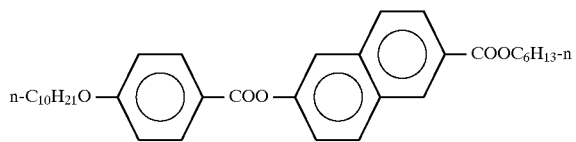
Exemplified compound 56
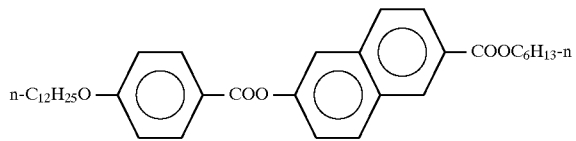
Exemplified compound 57
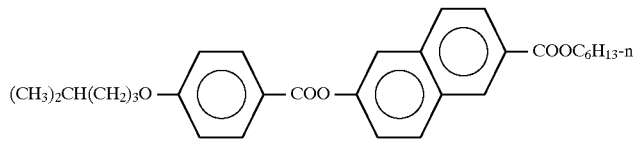
Exemplified compound 58
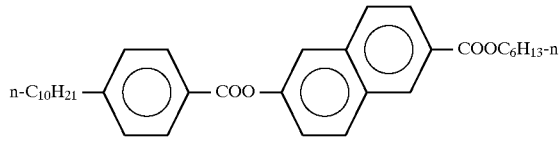
Exemplified compound 59
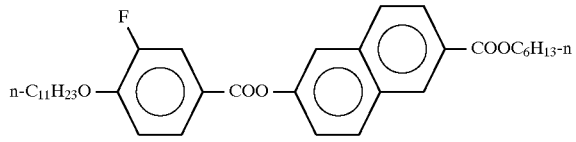
Exemplified compound 60

-continued
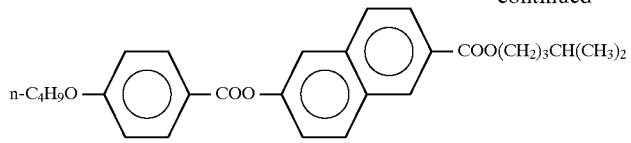
Exemplified compound 61
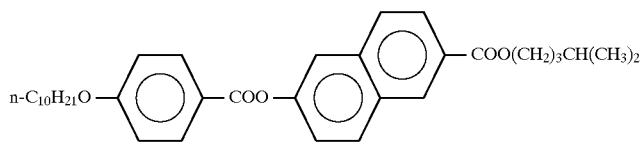
Exemplified compound 62
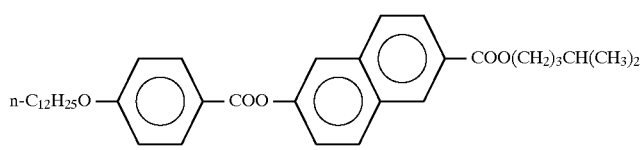
Exemplified compound 63
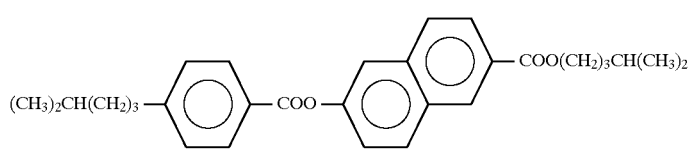
Exemplified compound 64
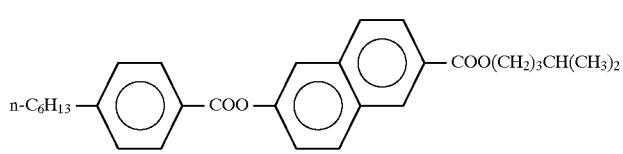
Exemplified compound 65
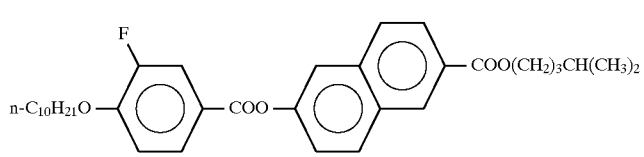
Exemplified compound 66
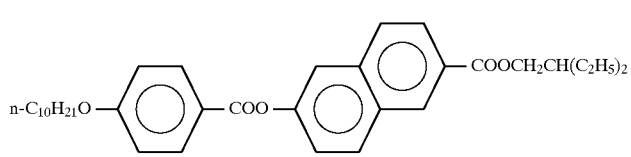
Exemplified compound 67
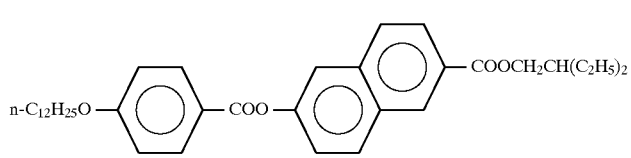
Exemplified compound 68
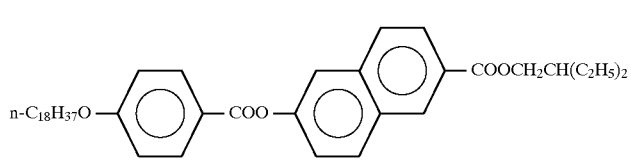
Exemplified compound 69
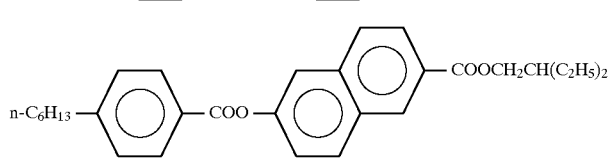
Exemplified compound 70
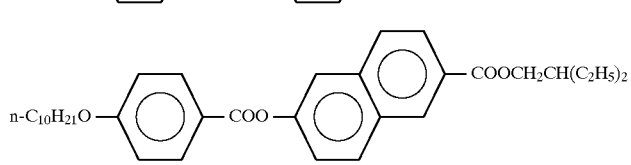
Exemplified compound 71

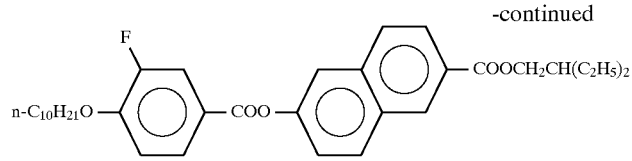
Exemplified compound 72
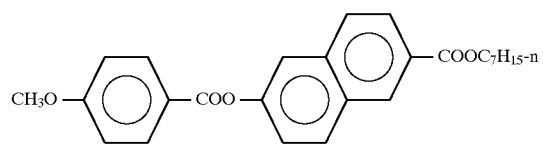
Exemplified compound 73
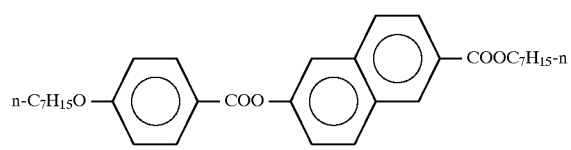
Exemplified compound 74
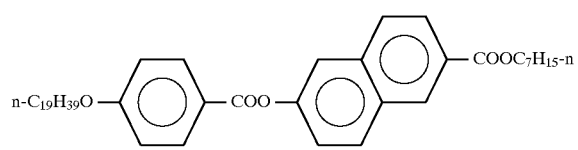
Exemplified compound 75
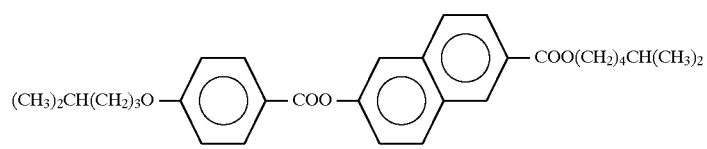
Exemplified compound 76
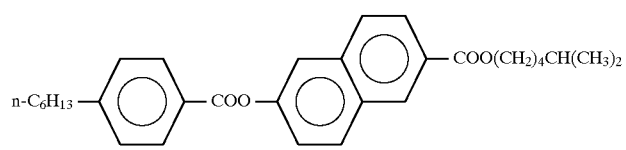
Exemplified compound 77
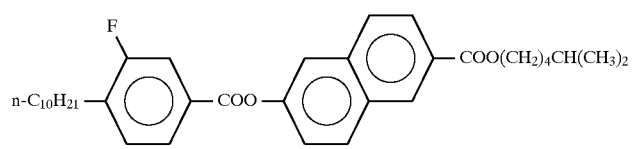
Exemplified compound 78
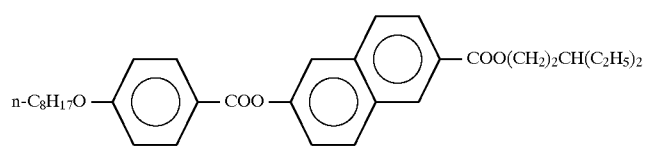
Exemplified compound 79
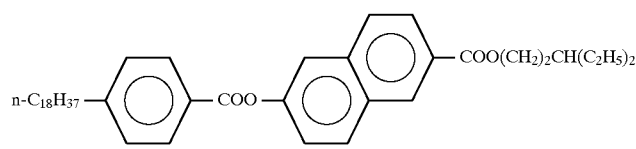
Exemplified compound 80
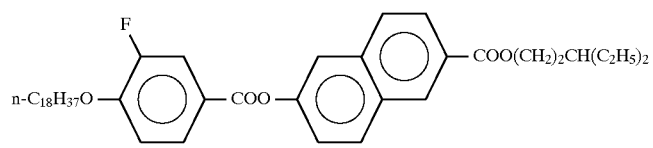
Exemplified compound 81
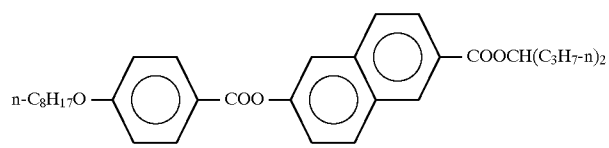
Exemplified compound 82

-continued
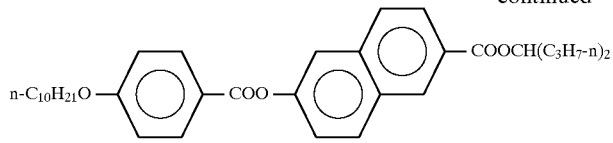
Exemplified compound 83
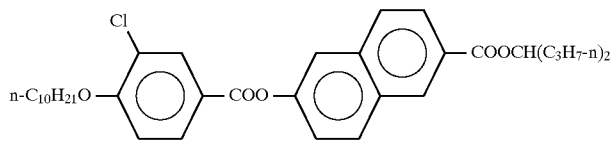
Exemplified compound 84
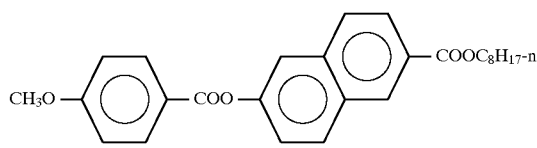
Exemplified compound 85
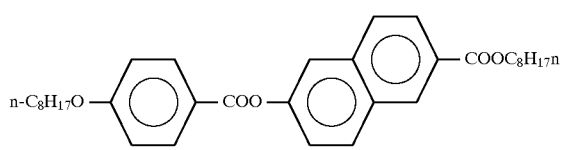
Exemplified compound 86
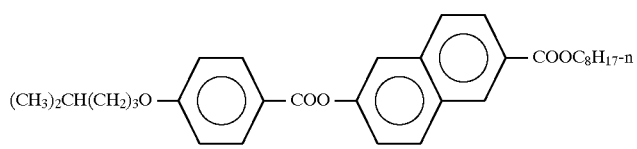
Exemplified compound 87
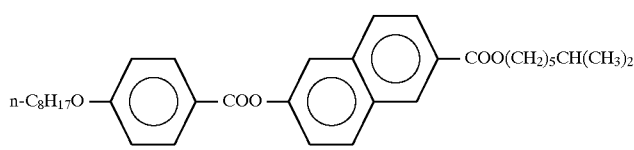
Exemplified compound 88
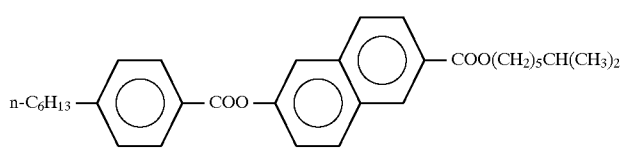
Exemplified compound 89
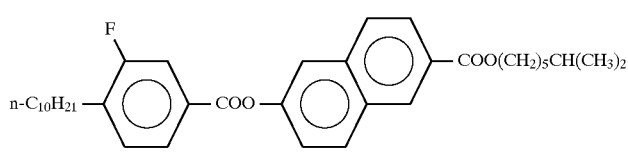
Exemplified compound 90
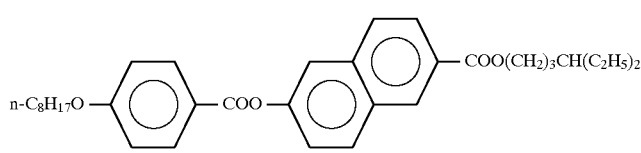
Exemplified compound 91
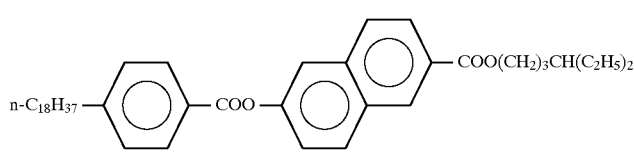
Exemplified compound 92
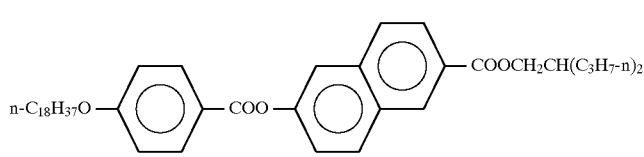
Exemplified compound 93

-continued
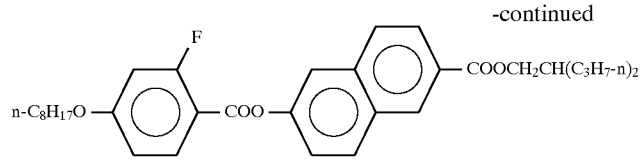
Exemplified compound 94
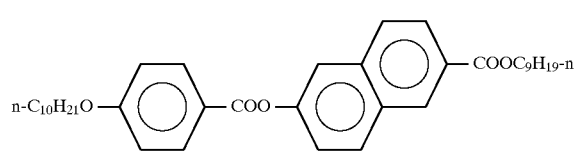
Exemplified compound 95
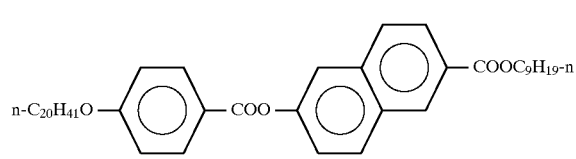
Exemplified compound 96
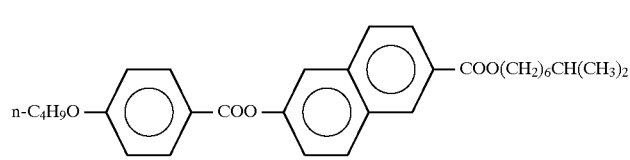
Exemplified compound 97
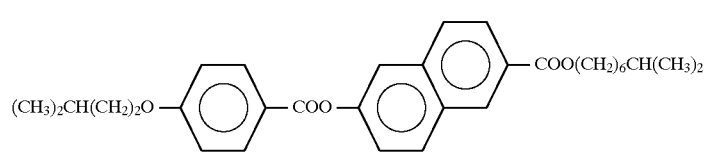
Exemplified compound 98
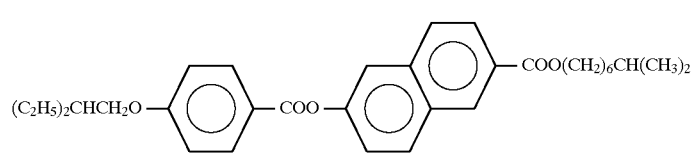
Exemplified compound 99
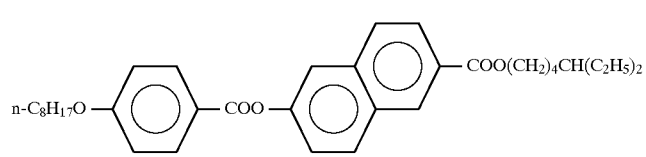
Exemplified compound 100
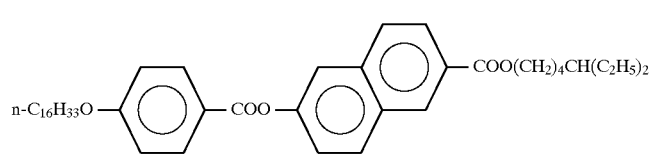
Exemplified compound 101
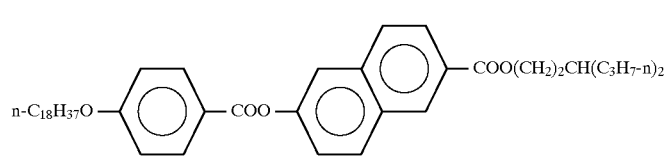
Exemplified compound 102
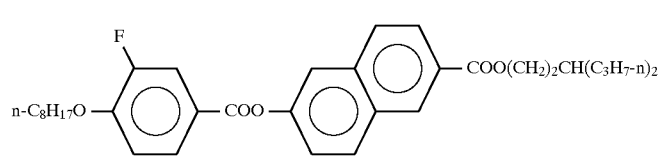
Exemplified compound 103
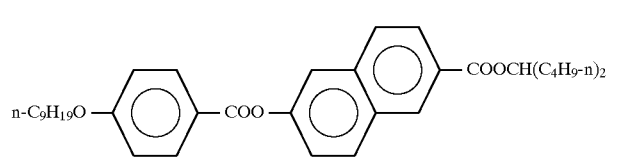
Exemplified compound 104

-continued
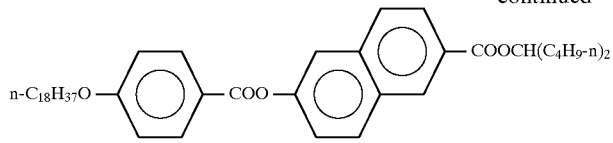
Exemplified compound 105
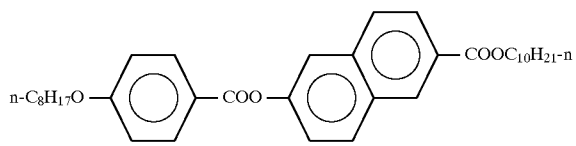
Exemplified compound 106
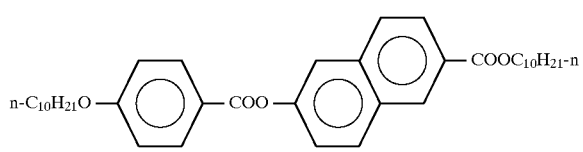
Exemplified compound 107
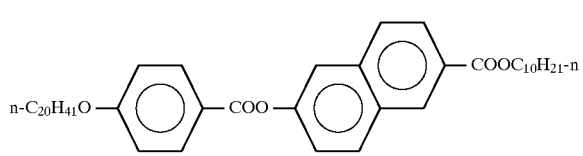
Exemplified compound 108
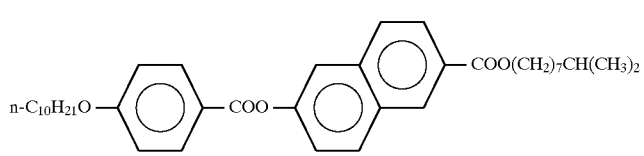
Exemplified compound 109
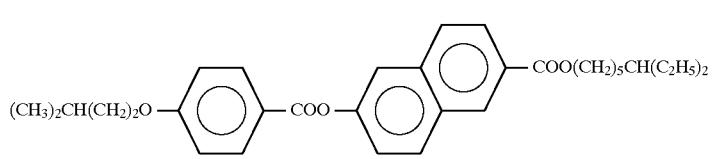
Exemplified compound 110
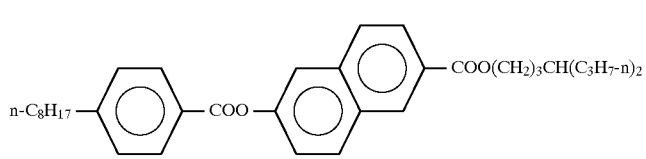
Exemplified compound 111
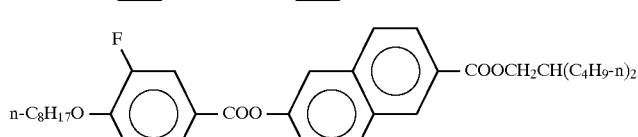
Exemplified compound 112
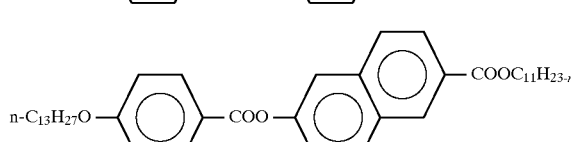
Exemplified compound 113
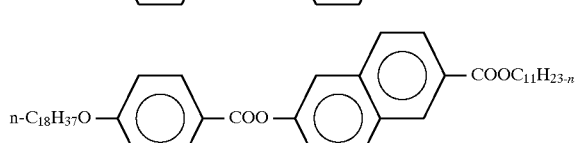
Exemplified compound 114
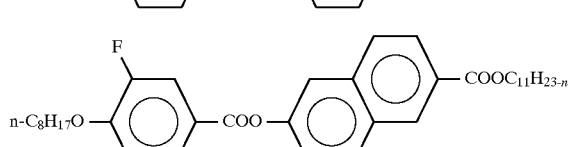
Exemplified compound 115

-continued
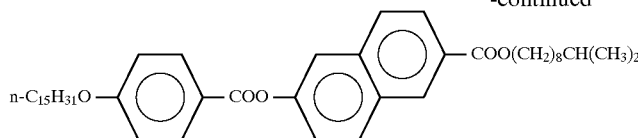
Exemplified compound 116
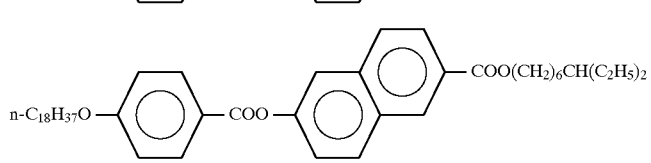
Exemplified compound 117
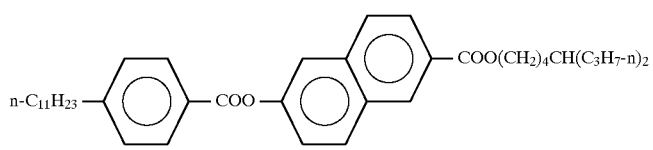
Exemplified compound 118
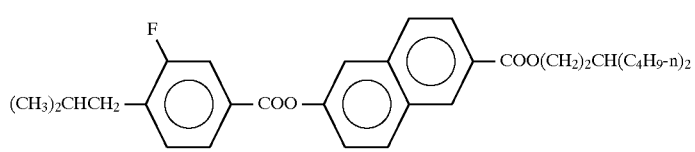
Exemplified compound 119
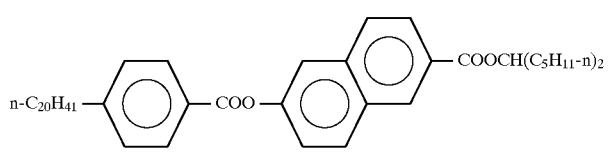
Exemplified compound 120
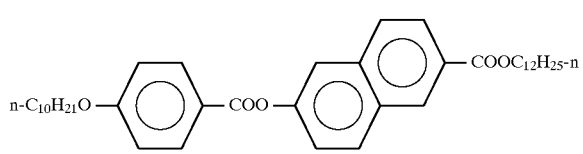
Exemplified compound 121
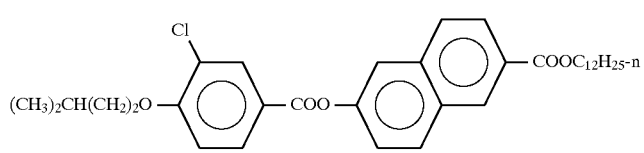
Exemplified compound 122
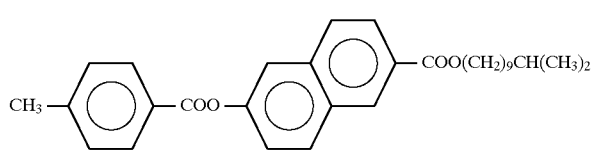
Exemplified compound 123
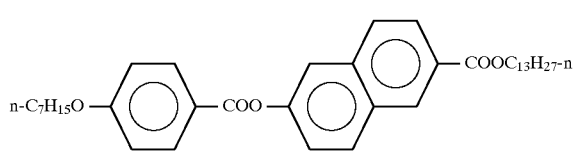
Exemplified compound 124
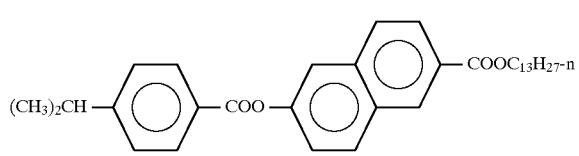
Exemplified compound 125
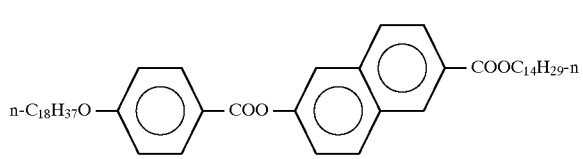
Exemplified compound 126

-continued
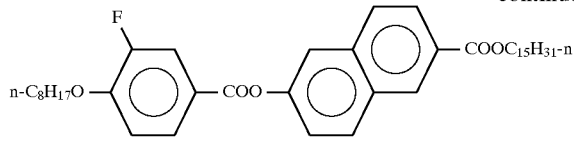
Exemplified compound 127
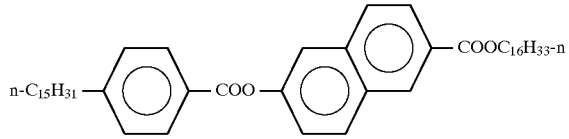
Exemplified compound 128
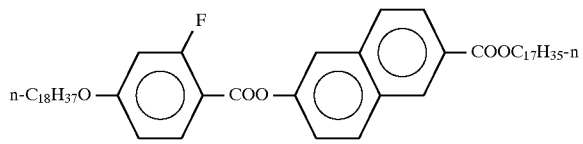
Exemplified compound 129
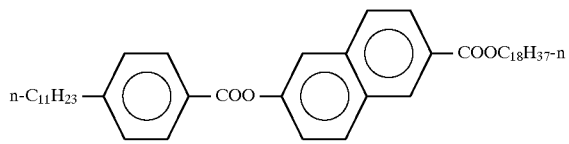
Exemplified compound 130
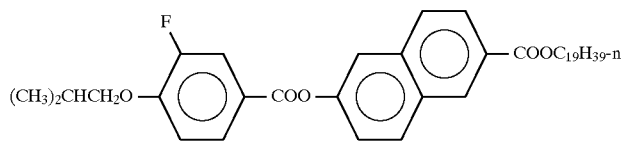
Exemplified compound 131
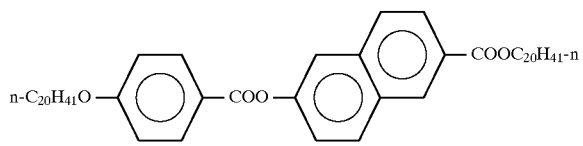
Exemplified compound 132
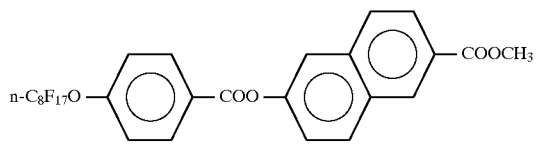
Exemplified compound 133
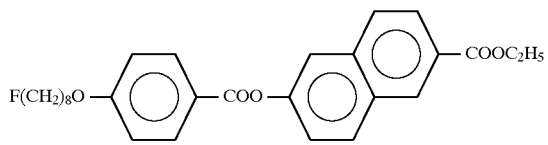
Exemplified compound 134
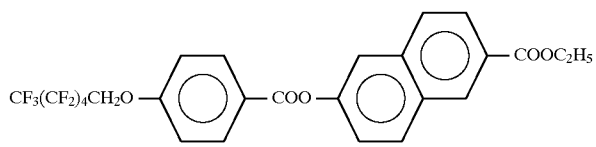
Exemplified compound 135
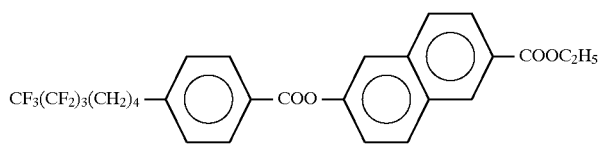
Exemplified compound 136
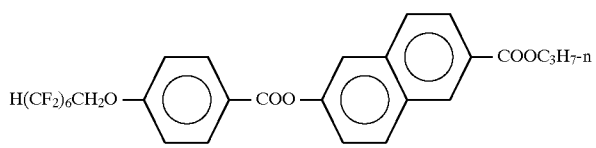
Exemplified compound 137

-continued
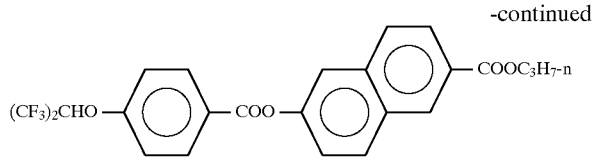
Exemplified compound 138
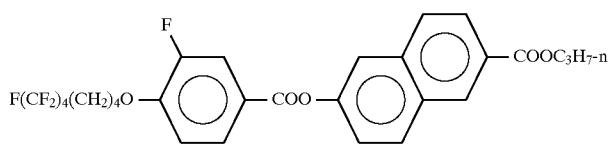
Exemplified compound 139
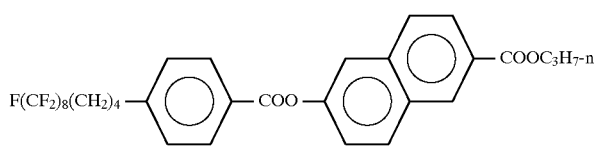
Exemplified compound 140
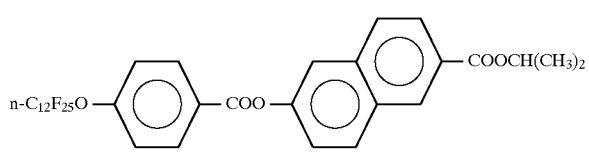
Exemplified compound 141
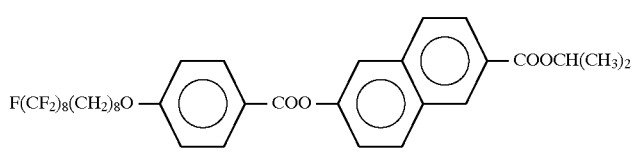
Exemplified compound 142
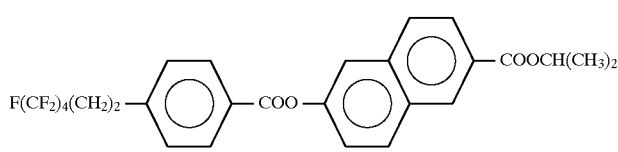
Exemplified compound 143
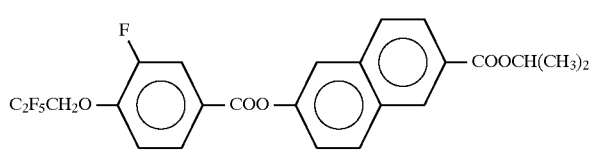
Exemplified compound 144
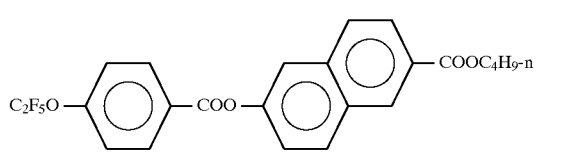
Exemplified compound 145
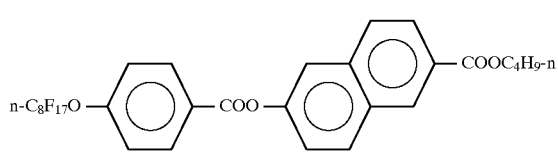
Exemplified compound 146
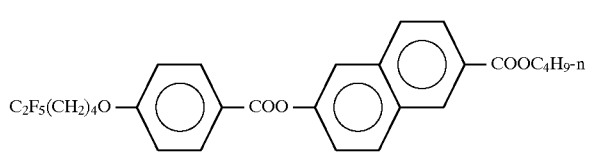
Exemplified compound 147
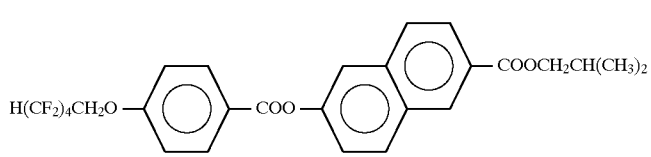
Exemplified compound 148

-continued
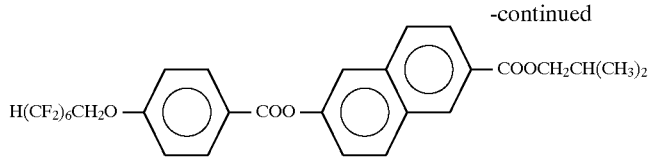
Exemplified compound 149
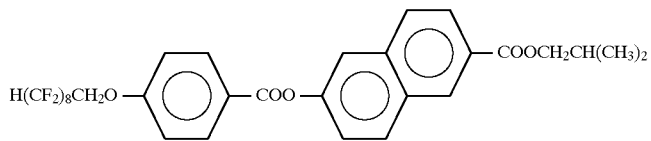
Exemplified compound 150
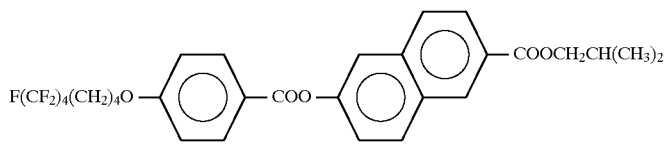
Exemplified compound 151
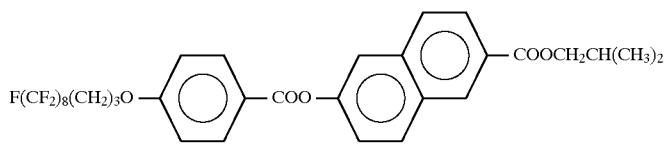
Exemplified compound 152
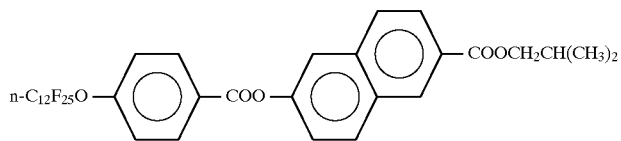
Exemplified compound 153
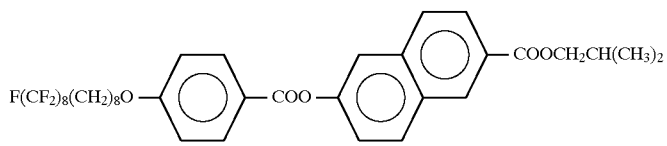
Exemplified compound 154
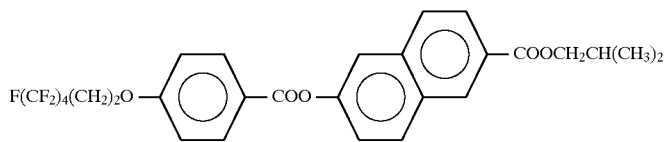
Exemplified compound 155
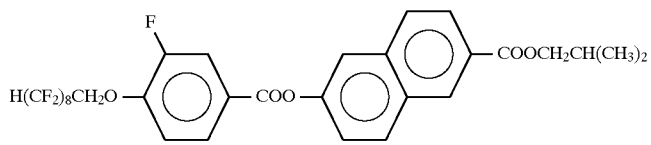
Exemplified compound 156
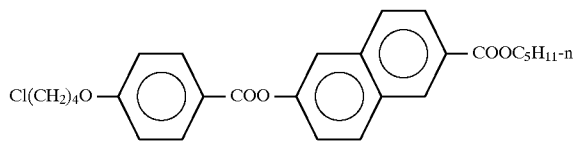
Exemplified compound 157
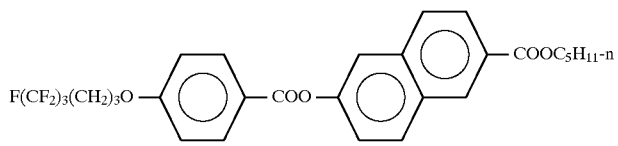
Exemplified compound 158
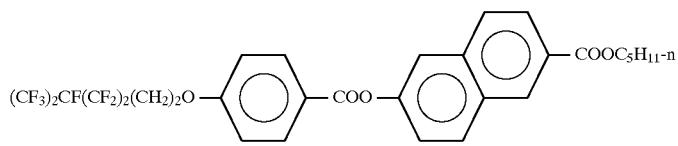
Exemplified compound 159

-continued
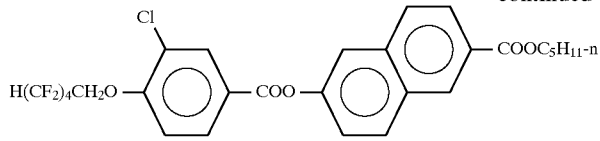 Exemplified compound 160
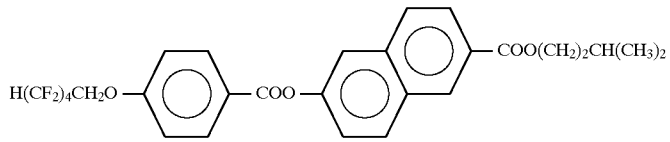 Exemplified compound 161
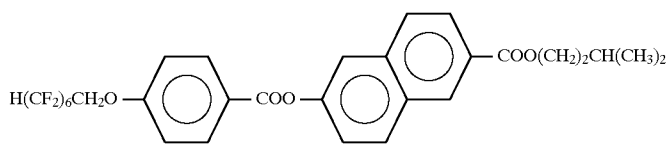 Exemplified compound 162
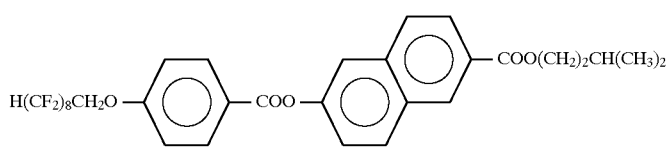 Exemplified compound 163
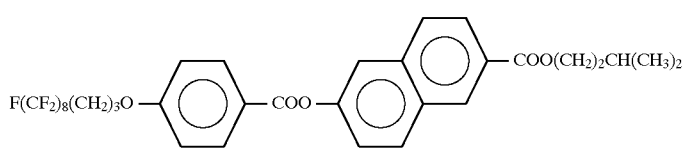 Exemplified compound 164
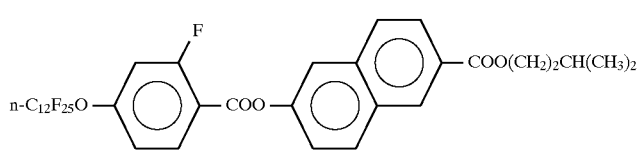 Exemplified compound 165
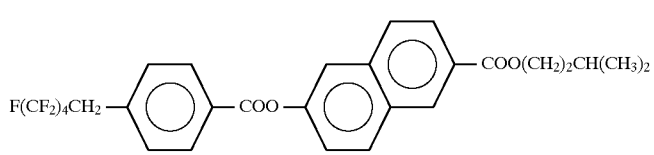 Exemplified compound 166
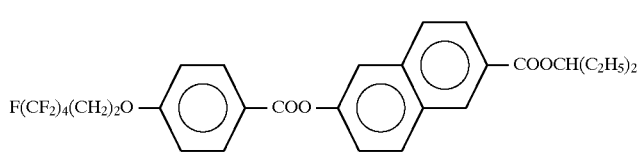 Exemplified compound 167
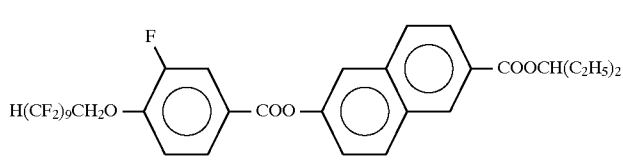 Exemplified compound 168
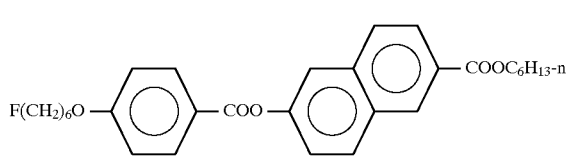 Exemplified compound 169
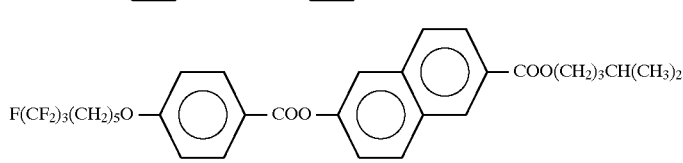 Exemplified compound 170

-continued
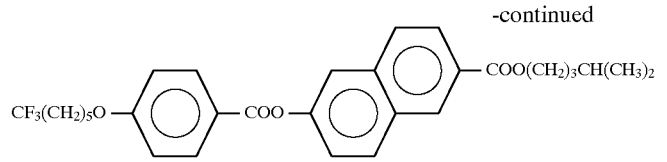
Exemplified compound 171
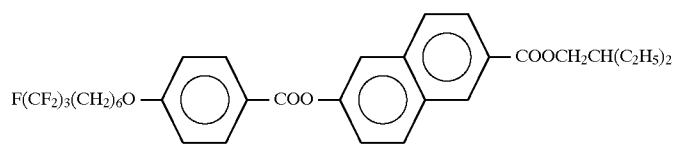
Exemplified compound 172
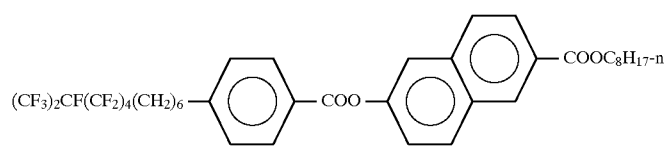
Exemplified compound 173
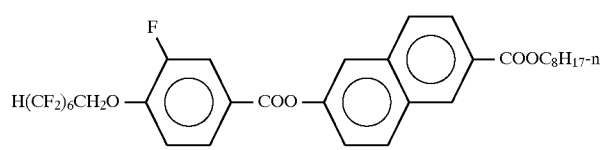
Exemplified compound 174
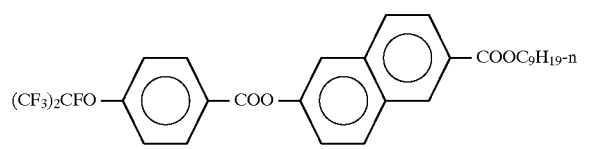
Exemplified compound 175
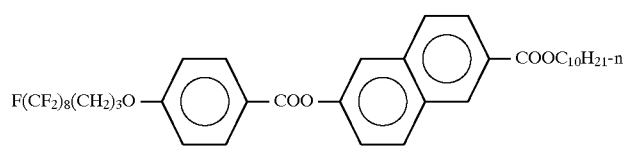
Exemplified compound 176
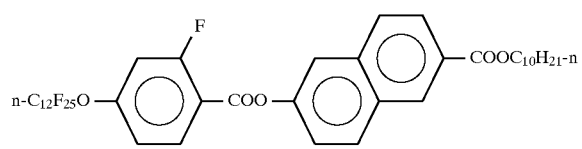
Exemplified compound 177
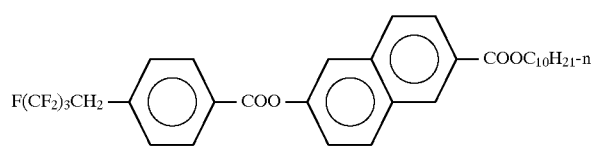
Exemplified compound 178
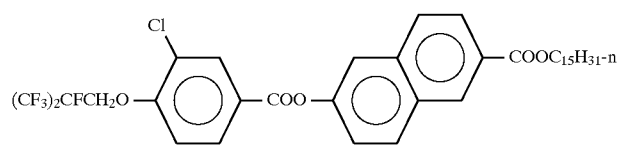
Exemplified compound 179
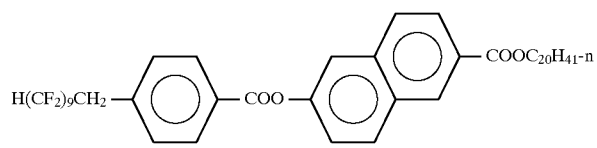
Exemplified compound 180
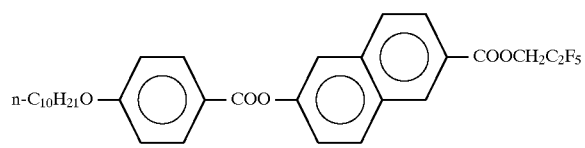
Exemplified compound 181

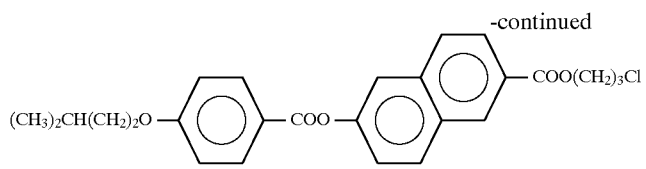
Exemplified compound 182
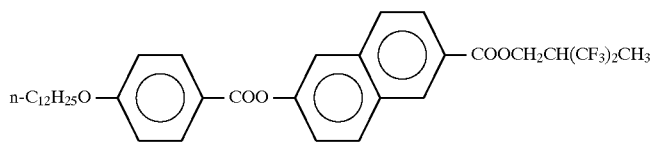
Exemplified compound 183
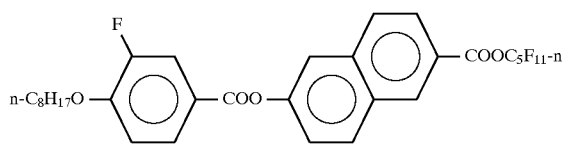
Exemplified compound 184
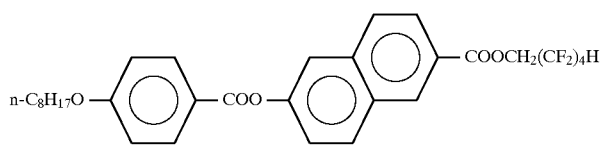
Exemplified compound 185
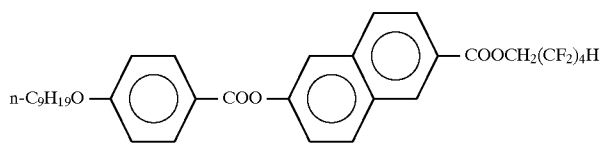
Exemplified compound 186
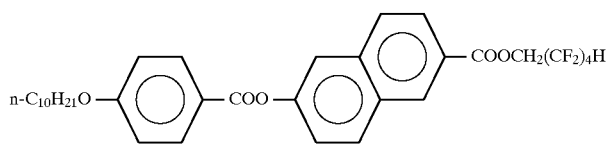
Exemplified compound 187
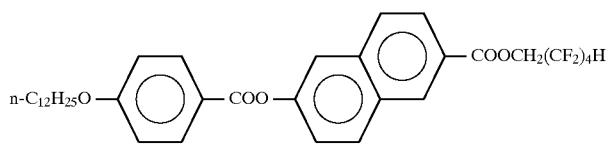
Exemplified compound 188
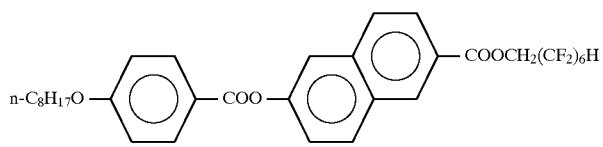
Exemplified compound 189
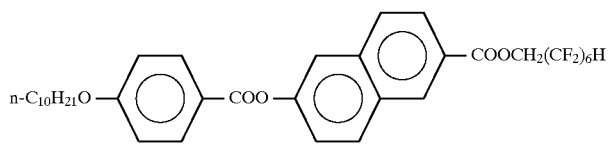
Exemplified compound 190
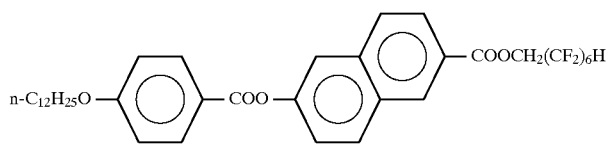
Exemplified compound 191
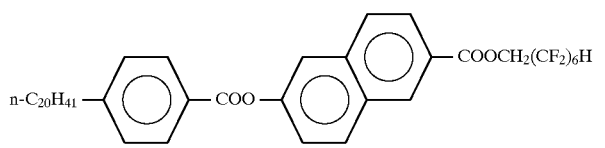
Exemplified compound 192

-continued
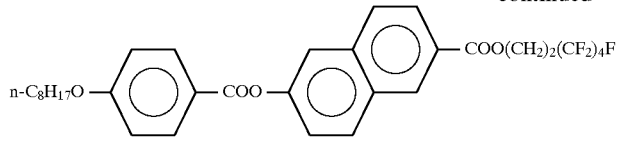
Exemplified compound 193
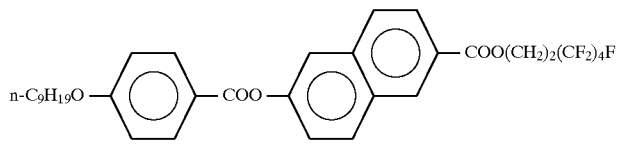
Exemplified compound 194
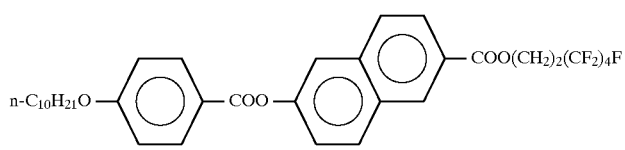
Exemplified compound 195
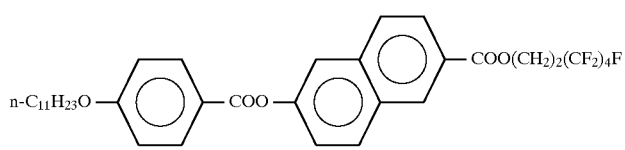
Exemplified compound 196
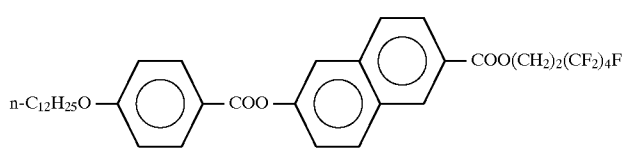
Exemplified compound 197
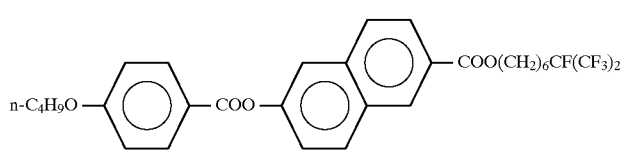
Exemplified compound 198
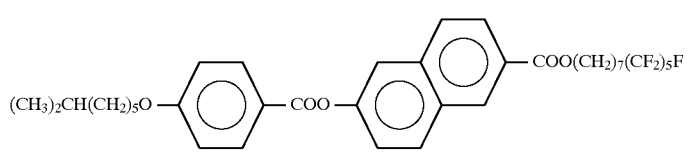
Exemplified compound 199
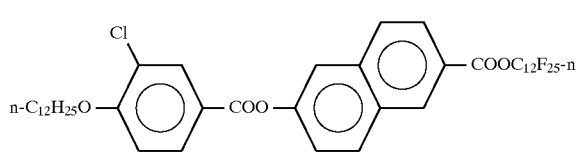
Exemplified compound 200
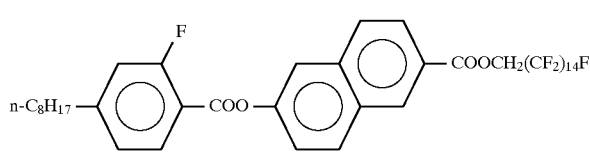
Exemplified compound 201
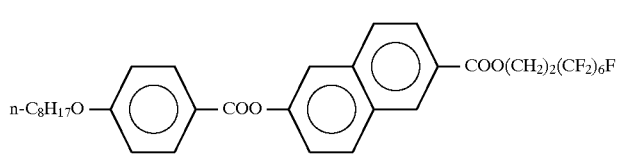
Exemplified compound 202
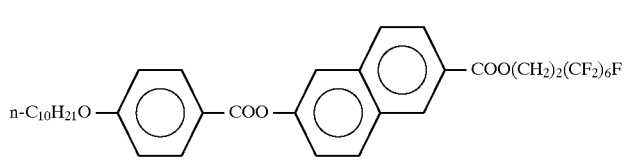
Exemplified compound 203

-continued
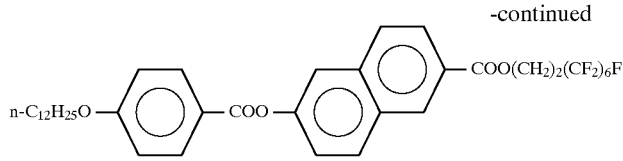
Exemplified compound 204
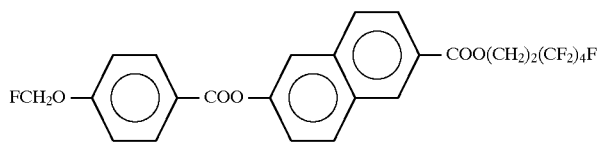
Exemplified compound 205
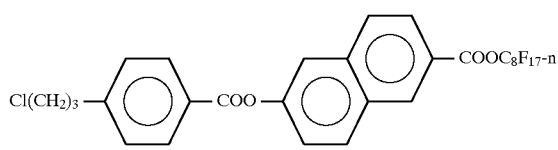
Exemplified compound 206
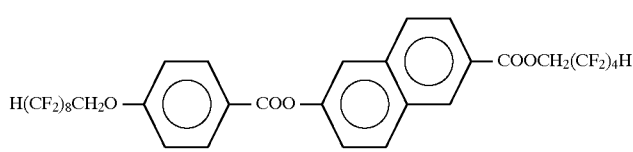
Exemplified compound 207
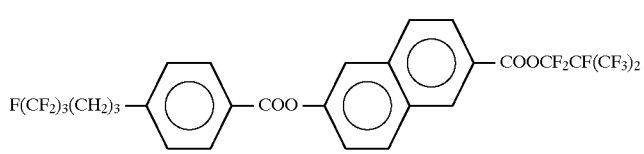
Exemplified compound 208
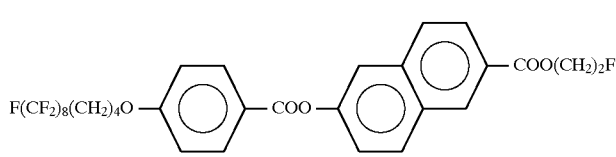
Exemplified compound 209
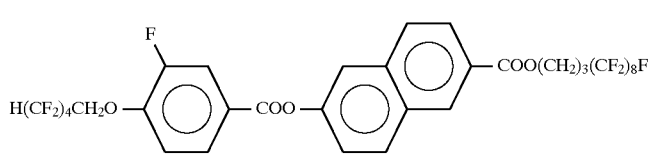
Exemplified compound 210
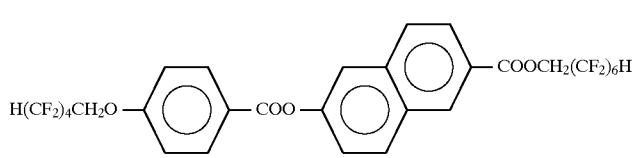
Exemplified compound 211
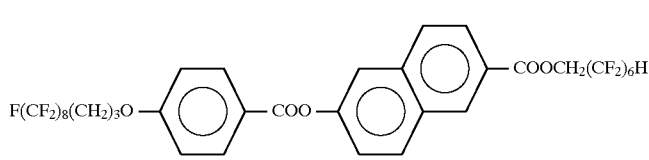
Exemplified compound 212
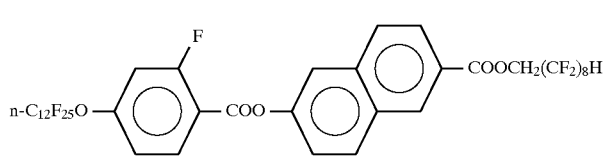
Exemplified compound 213
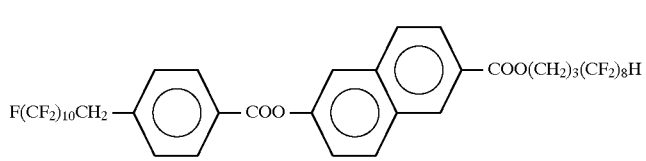
Exemplified compound 214

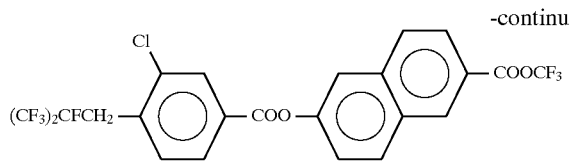
Exemplified compound 215
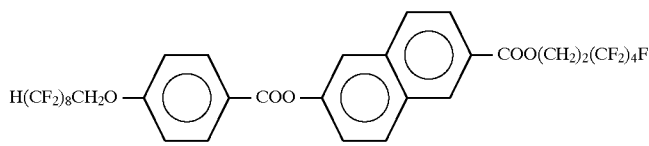
Exemplified compound 216
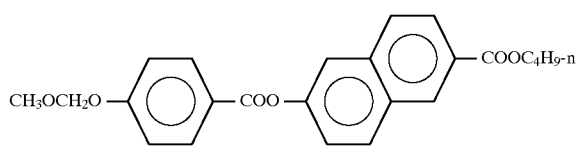
Exemplified compound 217
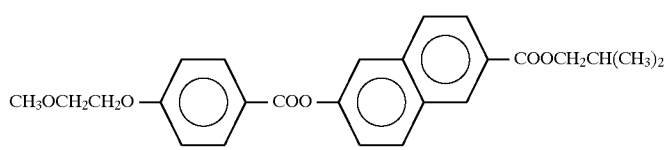
Exemplified compound 218
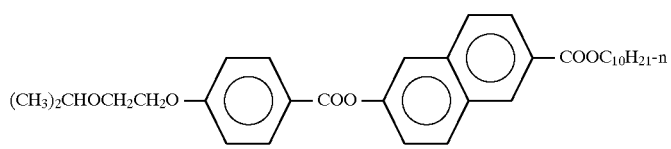
Exemplified compound 219
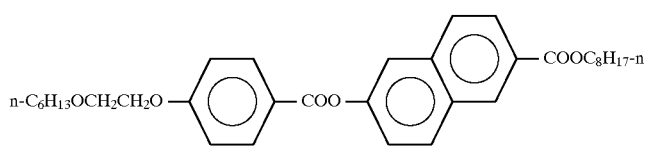
Exemplified compound 220
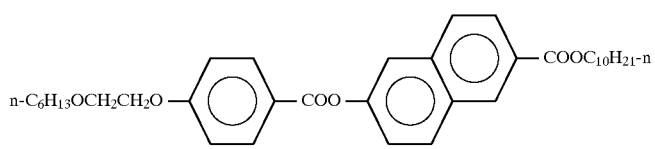
Exemplified compound 221
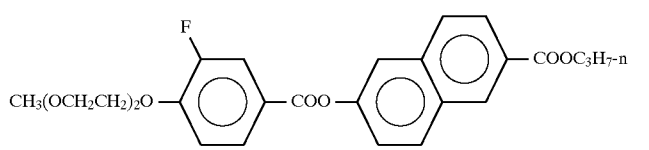
Exemplified compound 222
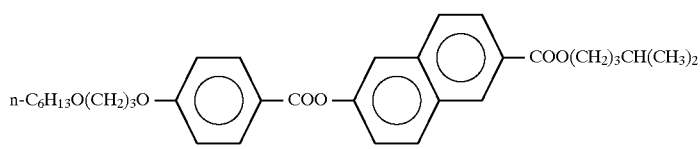
Exemplified compound 223
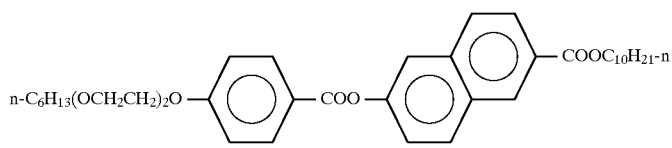
Exemplified compound 224
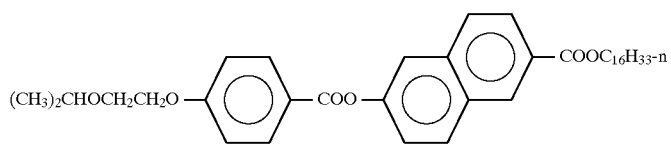
Exemplified compound 225

-continued
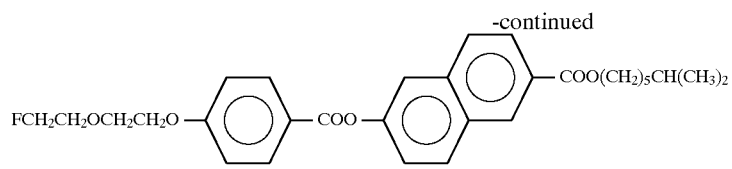 Exemplified compound 226
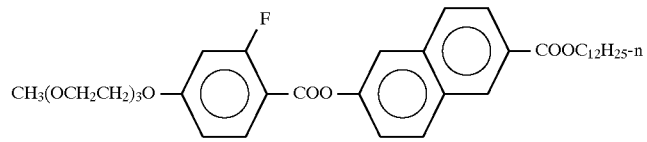 Exemplified compound 227
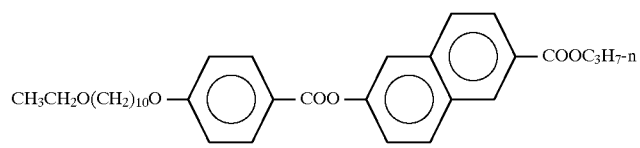 Exemplified compound 228
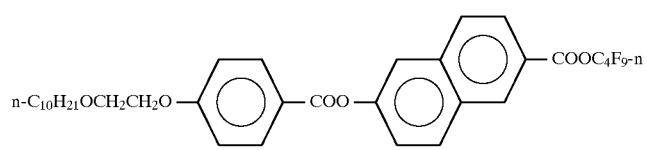 Exemplified compound 229
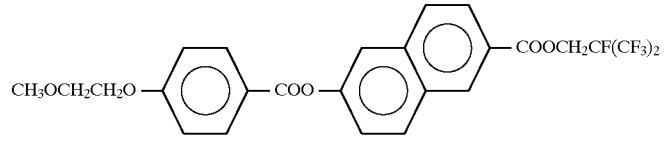 Exemplified compound 230
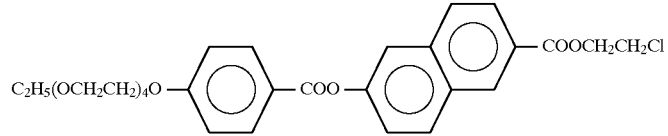 Exemplified compound 231
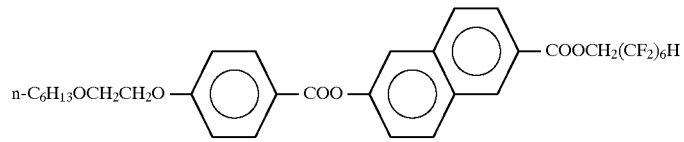 Exemplified compound 232
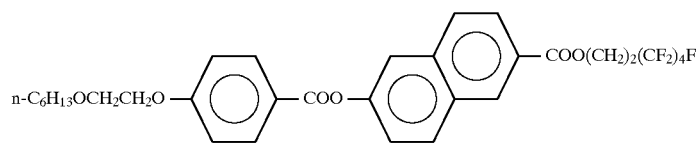 Exemplified compound 233
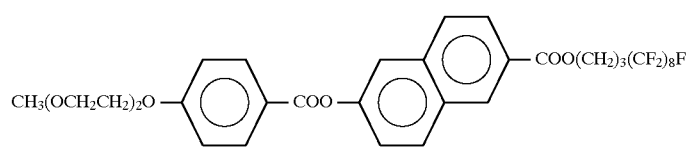 Exemplified compound 234
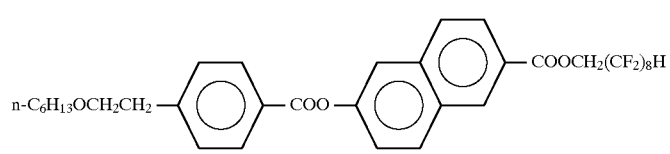 Exemplified compound 235
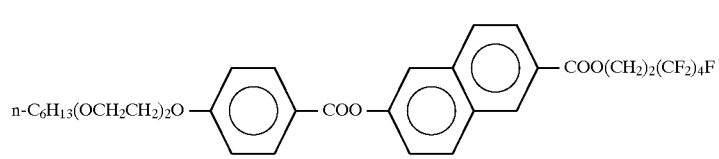 Exemplified compound 236

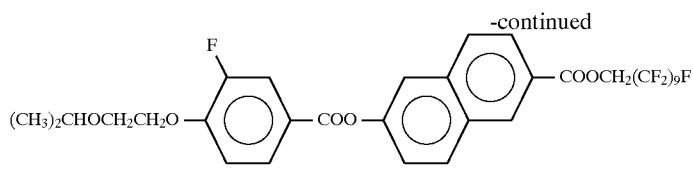
-continued
Exemplified compound 237
Exemplified compound 238
Exemplified compound 239
Exemplified compound 240
Exemplified compound 241
Exemplified compound 242
Exemplified compound 243
Exemplified compound 244
Exemplified compound 245
Exemplified compound 246
Exemplified compound 247

-continued
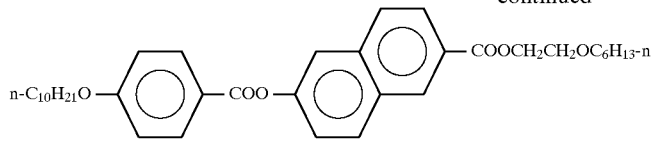
Exemplified compound 248
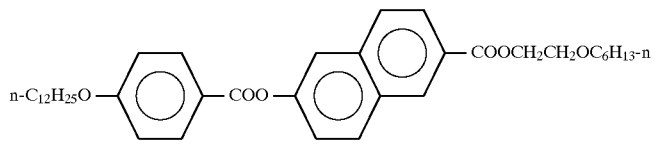
Exemplified compound 249
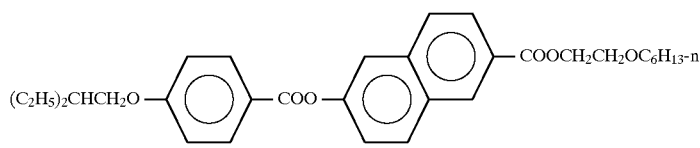
Exemplified compound 250
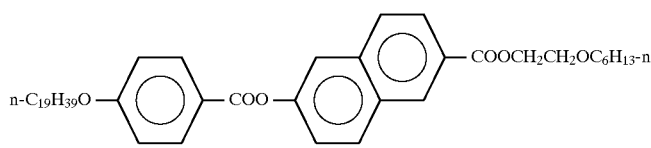
Exemplified compound 251
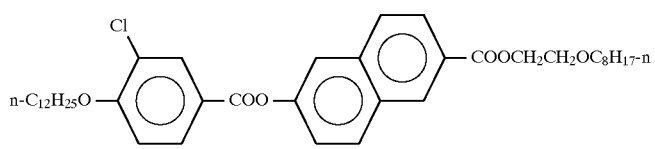
Exemplified compound 252
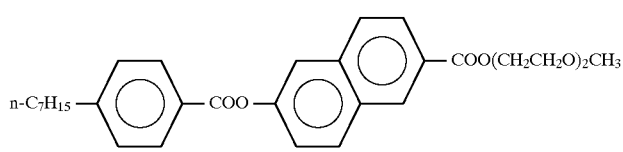
Exemplified compound 253
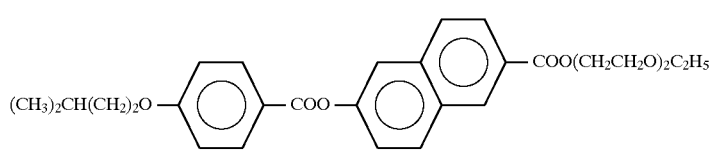
Exemplified compound 254
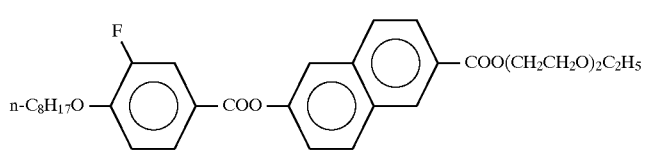
Exemplified compound 255
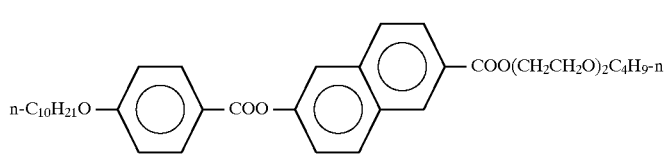
Exemplified compound 256
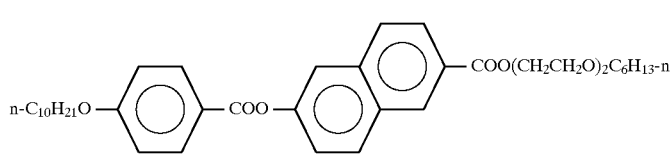
Exemplified compound 257
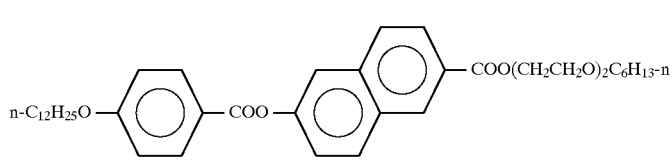
Exemplified compound 258

-continued
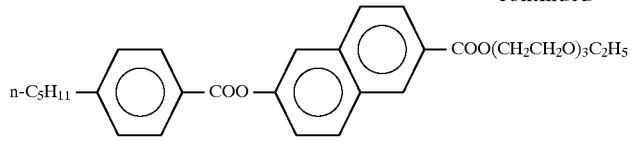
Exemplified compound 259
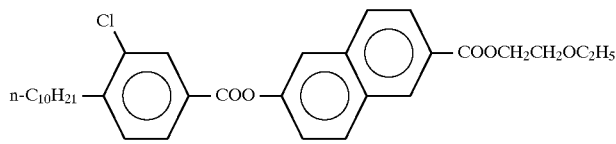
Exemplified compound 260
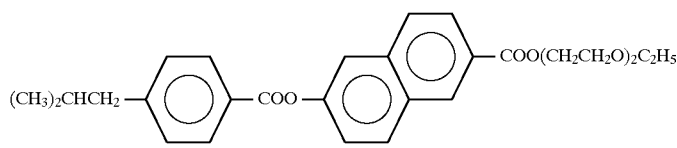
Exemplified compound 261
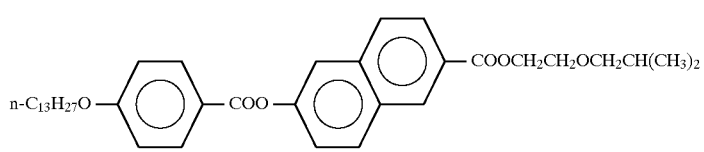
Exemplified compound 262
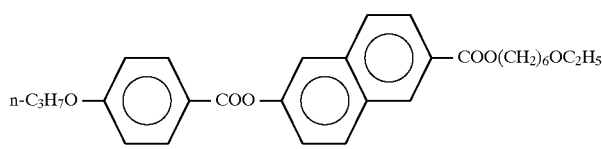
Exemplified compound 263
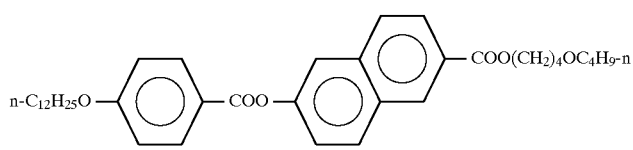
Exemplified compound 264
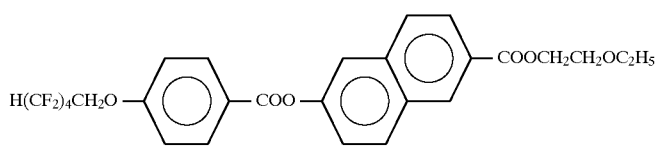
Exemplified compound 265
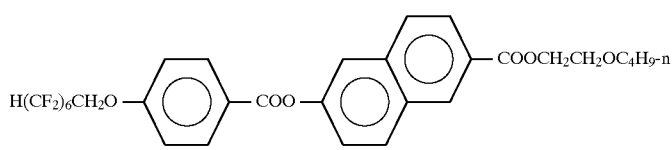
Exemplified compound 266
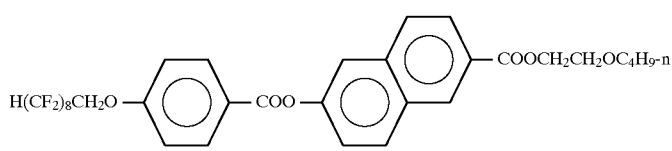
Exemplified compound 267
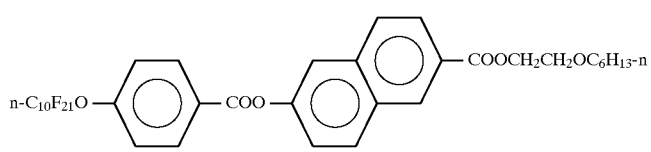
Exemplified compound 268
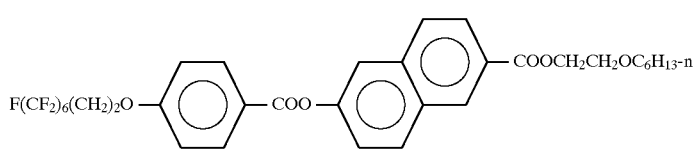
Exemplified compound 269

-continued
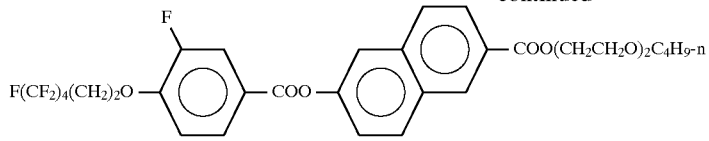 Exemplified compound 270
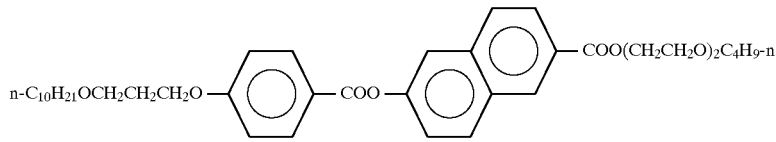 Exemplified compound 271
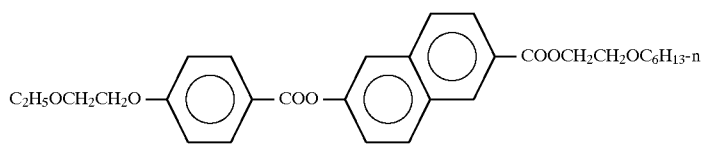 Exemplified compound 272
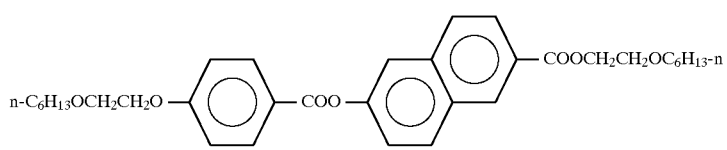 Exemplified compound 273
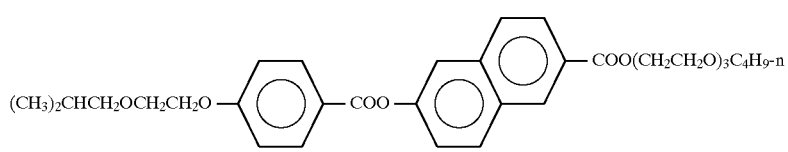 Exemplified compound 274
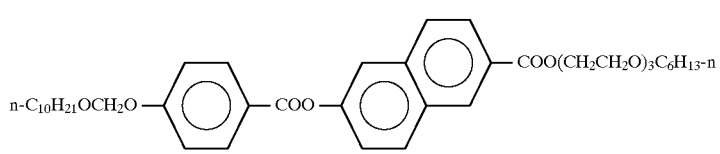 Exemplified compound 275
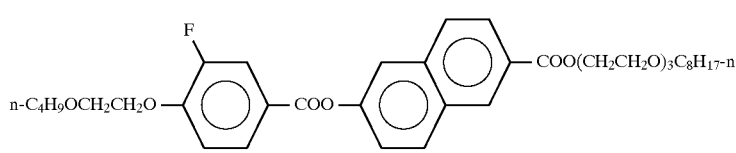 Exemplified compound 276
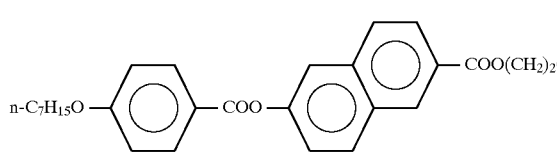 Exemplified compound 277
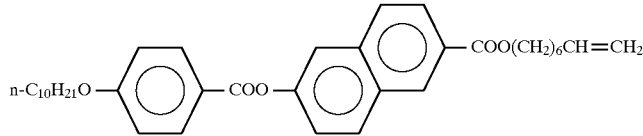 Exemplified compound 278
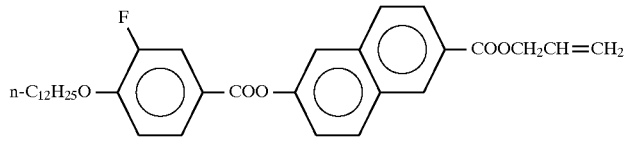 Exemplified compound 279
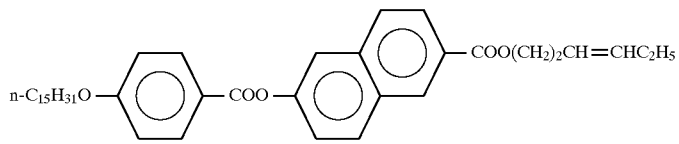 Exemplified compound 280

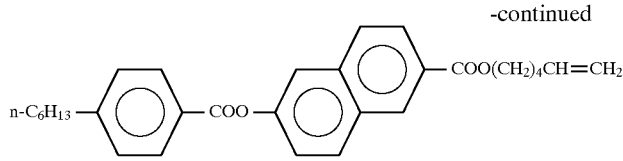
Exemplified compound 281
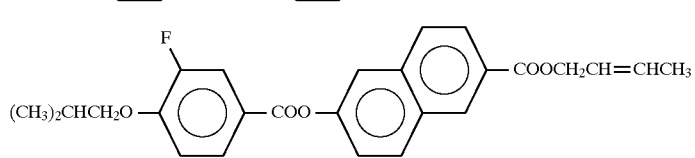
Exemplified compound 282
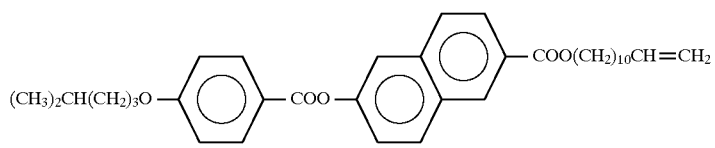
Exemplified compound 283
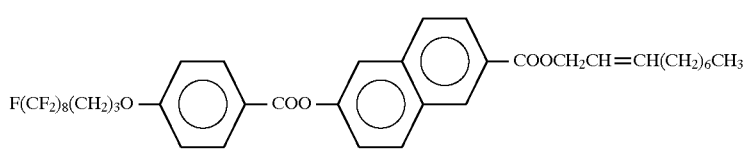
Exemplified compound 284
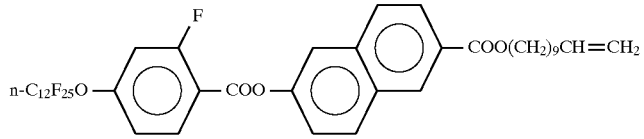
Exemplified compound 285
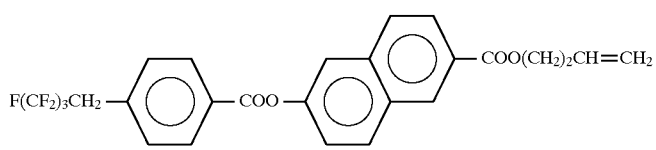
Exemplified compound 286
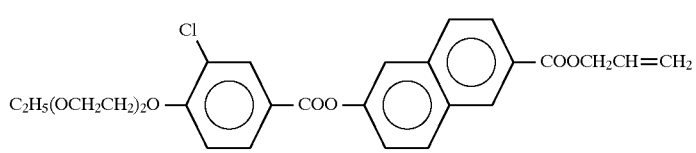
Exemplified compound 287
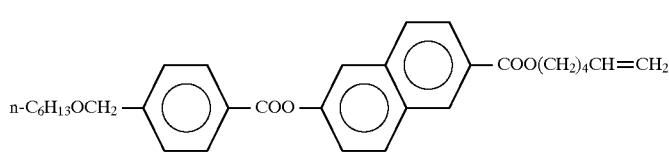
Exemplified compound 288
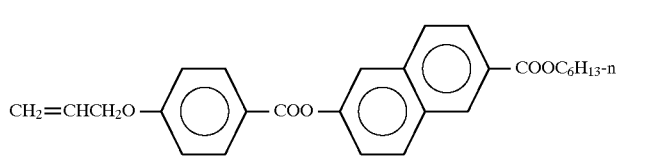
Exemplified compound 289
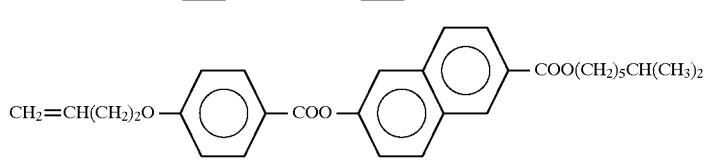
Exemplified compound 290
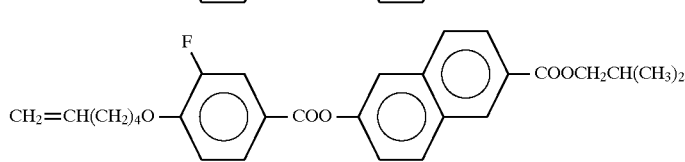
Exemplified compound 291

-continued
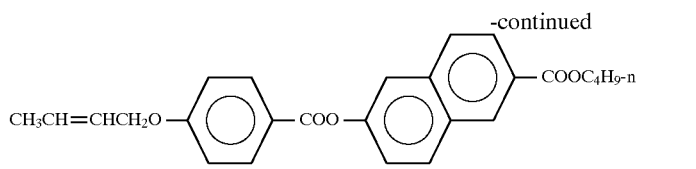
Exemplified compound 292
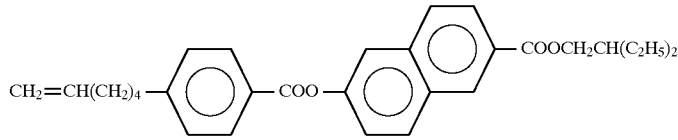
Exemplified compound 293
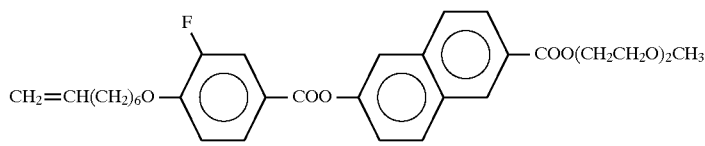
Exemplified compound 294
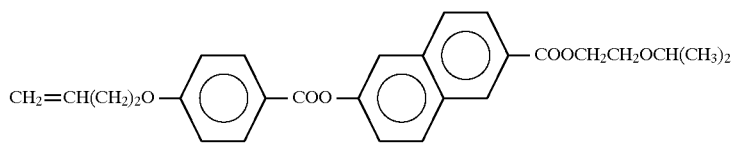
Exemplified compound 295
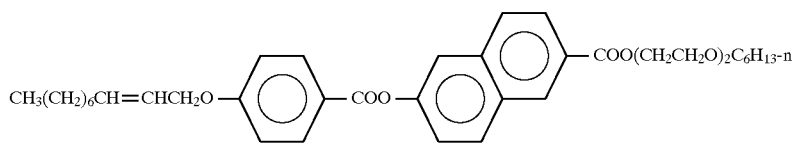
Exemplified compound 296
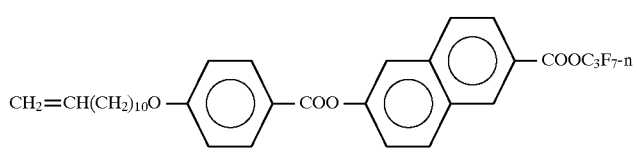
Exemplified compound 297
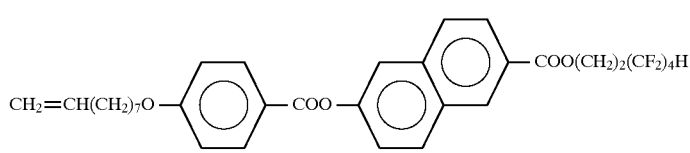
Exemplified compound 298
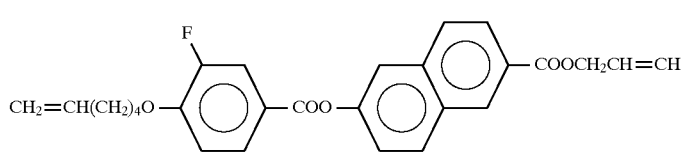
Exemplified compound 299
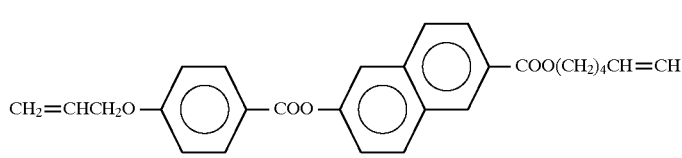
Exemplified compound 300
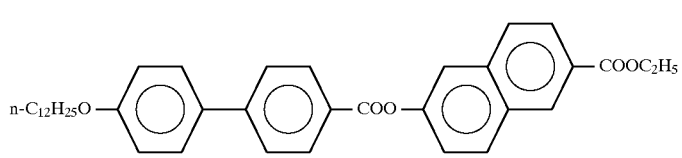
Exemplified compound 301
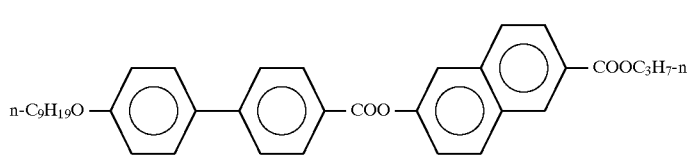
Exemplified compound 302

-continued
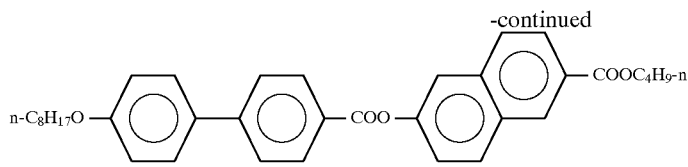
Exemplified compound 303
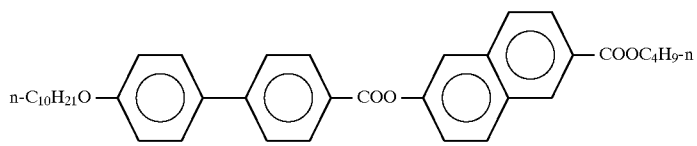
Exemplified compound 304
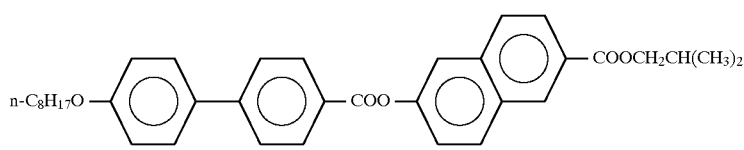
Exemplified compound 305
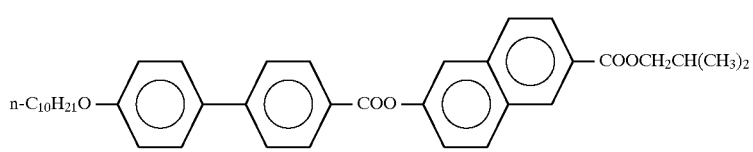
Exemplified compound 306
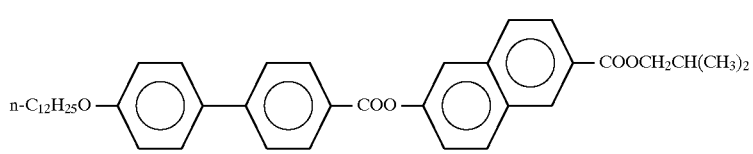
Exemplified compound 307
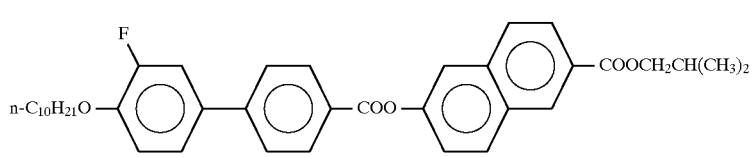
Exemplified compound 308
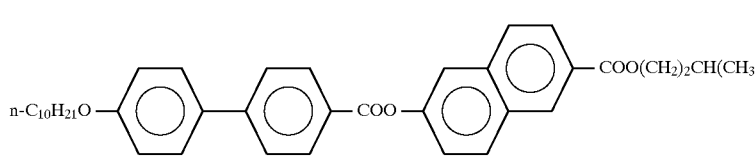
Exemplified compound 309
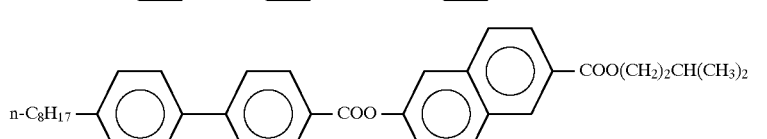
Exemplified compound 310
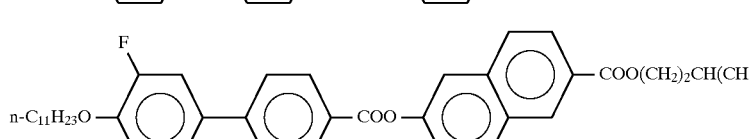
Exemplified compound 311
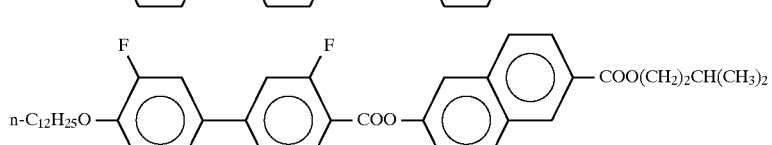
Exemplified compound 312
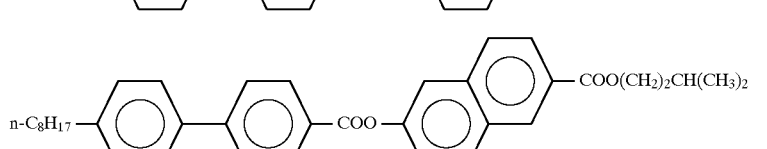
Exemplified compound 313

-continued
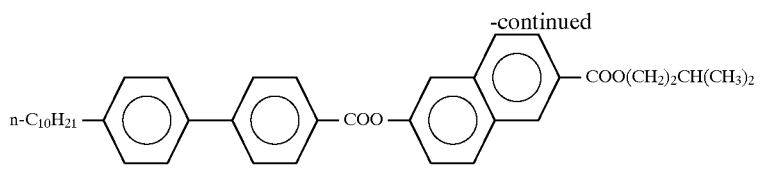 Exemplified compound 314
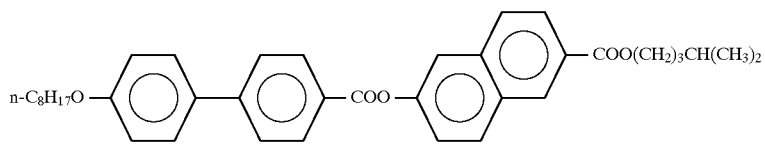 Exemplified compound 315
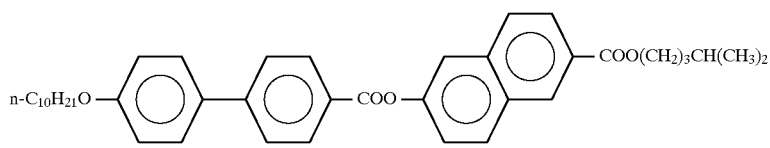 Exemplified compound 316
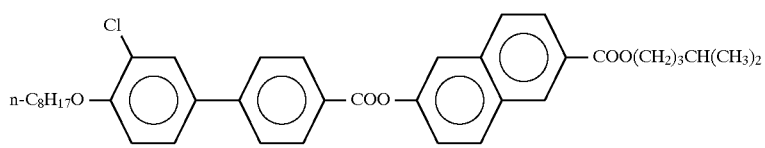 Exemplified compound 317
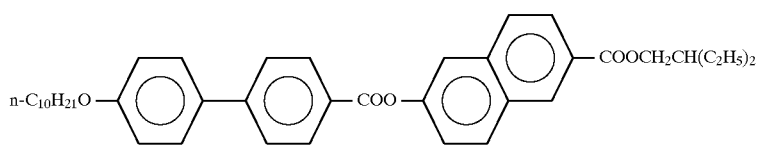 Exemplified compound 318
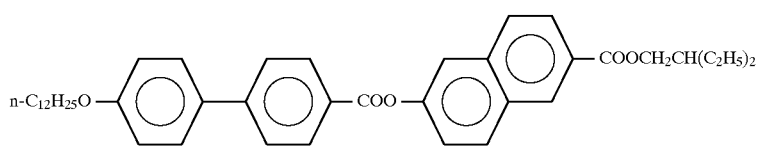 Exemplified compound 319
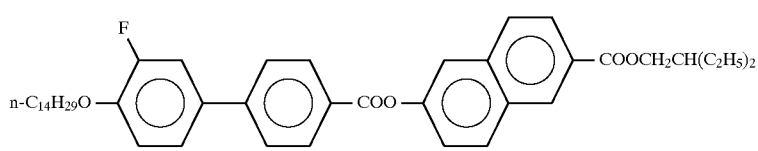 Exemplified compound 320
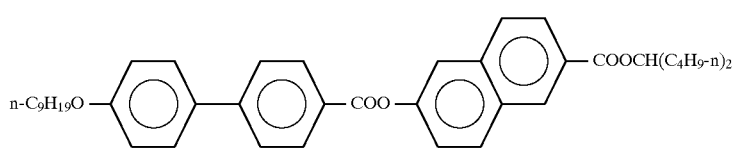 Exemplified compound 321
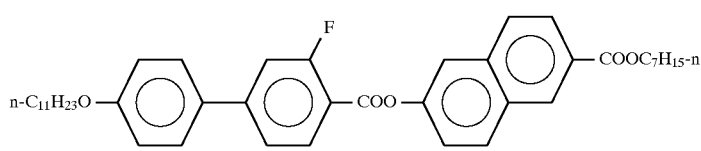 Exemplified compound 322
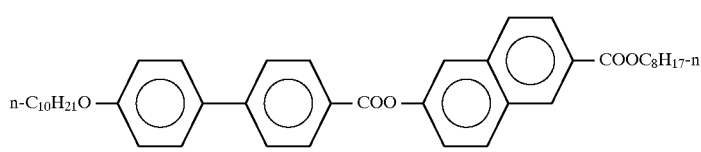 Exemplified compound 323
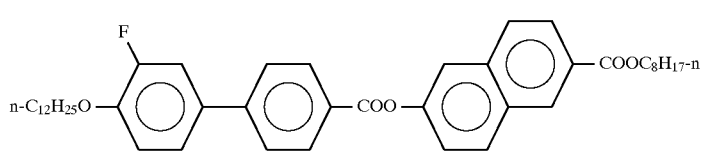 Exemplified compound 324

-continued
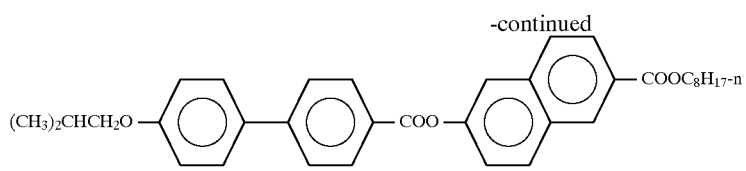
Exemplified compound 325
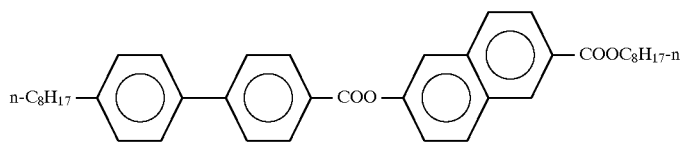
Exemplified compound 326
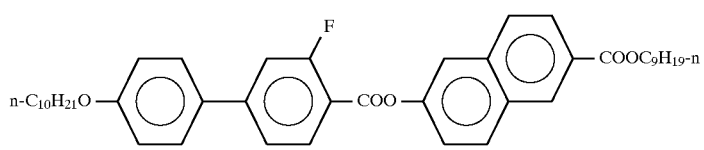
Exemplified compound 327
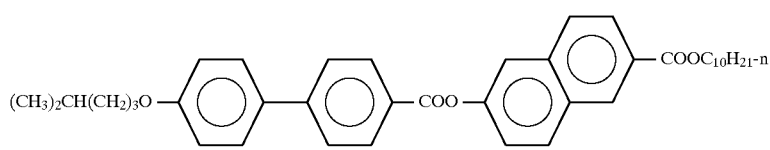
Exemplified compound 328
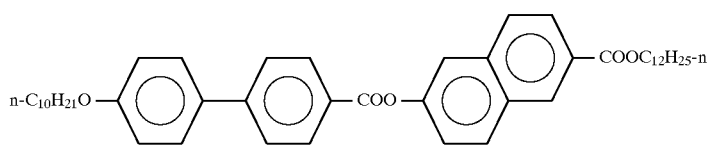
Exemplified compound 329
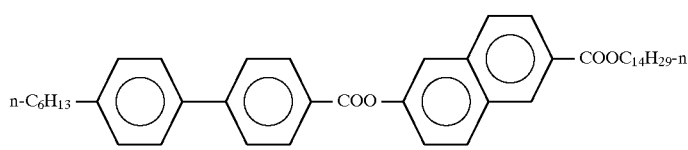
Exemplified compound 330
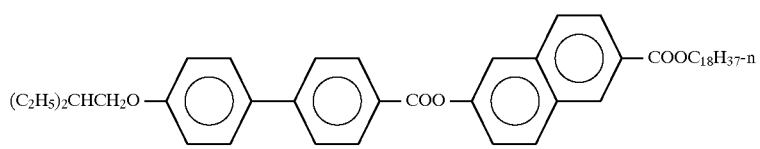
Exemplified compound 331
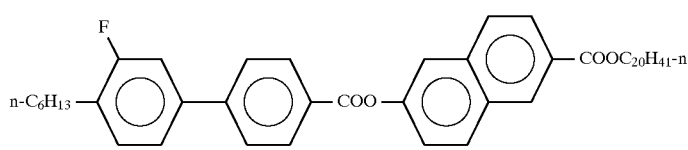
Exemplified compound 332
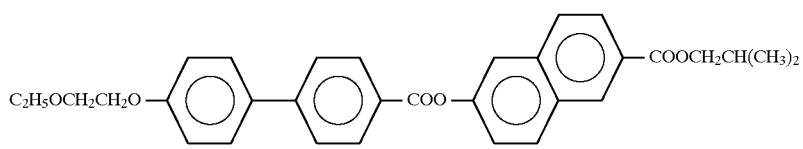
Exemplified compound 333
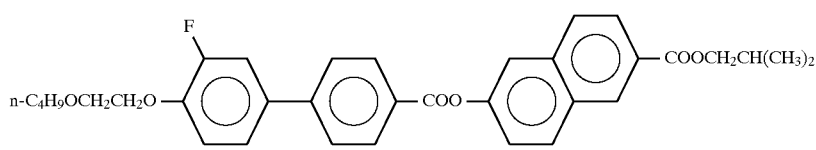
Exemplified compound 334
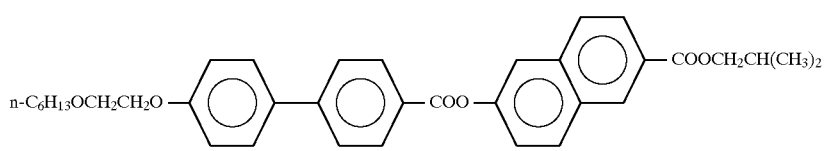
Exemplified compound 335

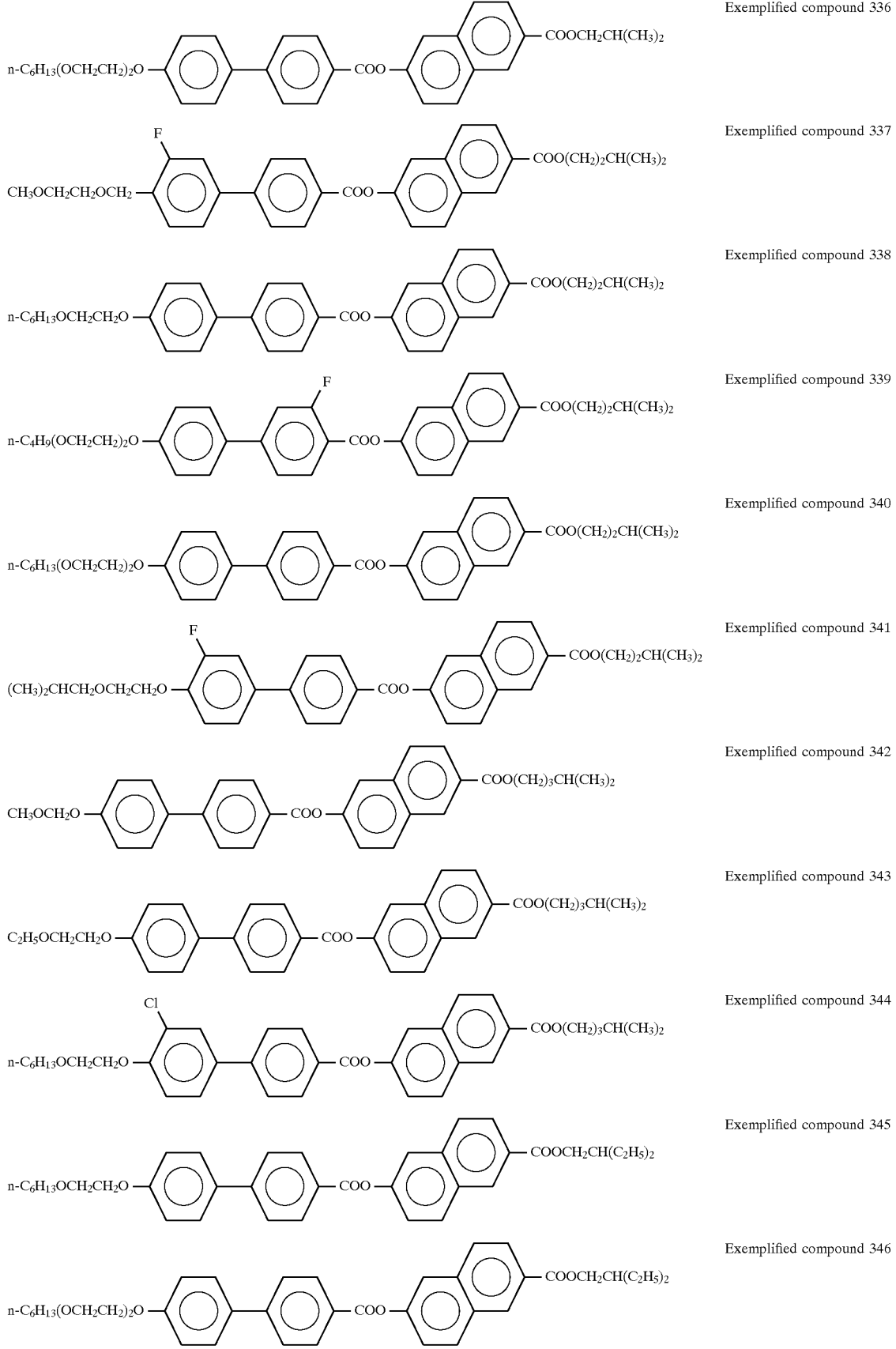

-continued
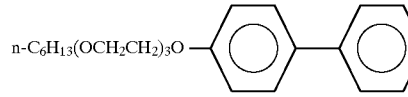
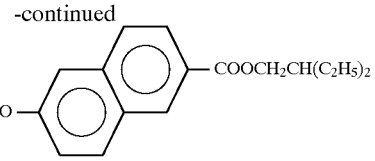
Exemplified compound 347
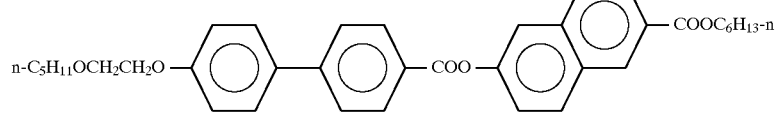
Exemplified compound 348
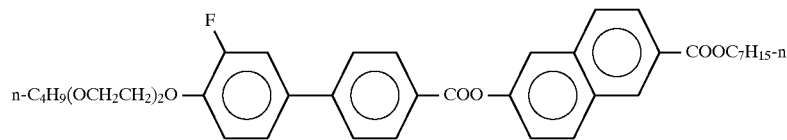
Exemplified compound 349
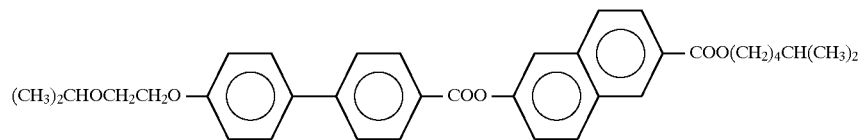
Exemplified compound 350
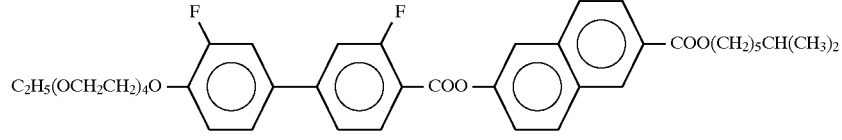
Exemplified compound 351
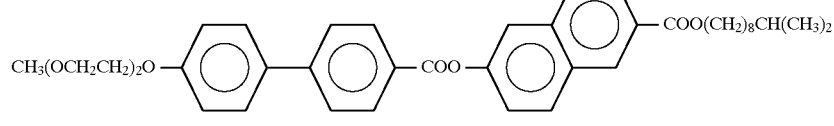
Exemplified compound 352
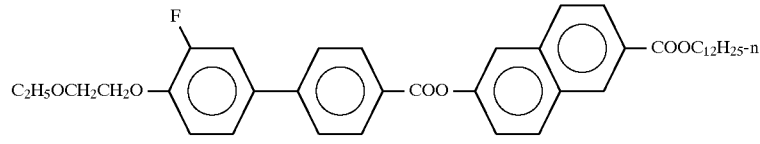
Exemplified compound 353
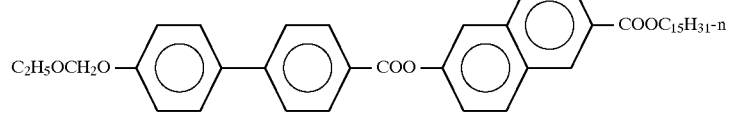
Exemplified compound 354
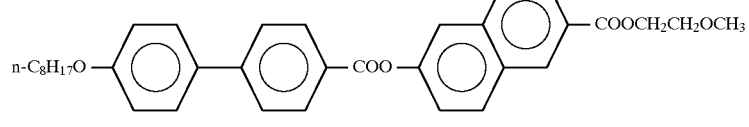
Exemplified compound 355
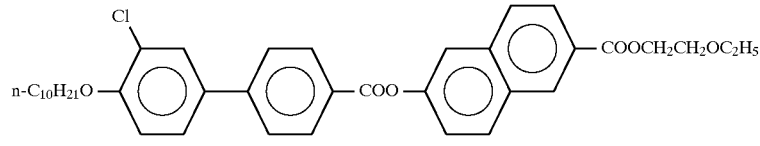
Exemplified compound 356
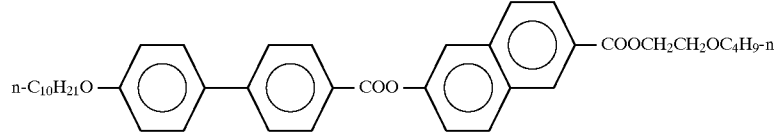
Exemplified compound 357

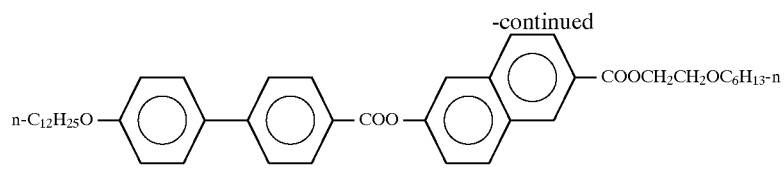
Exemplified compound 358
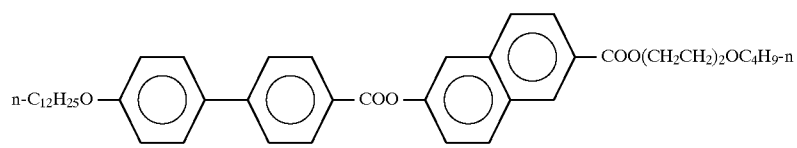
Exemplified compound 359
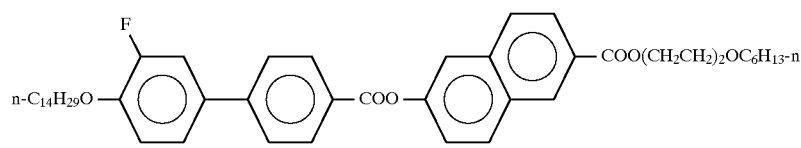
Exemplified compound 360
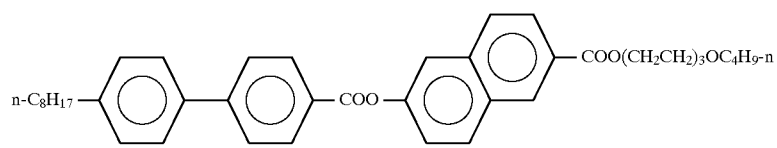
Exemplified compound 361
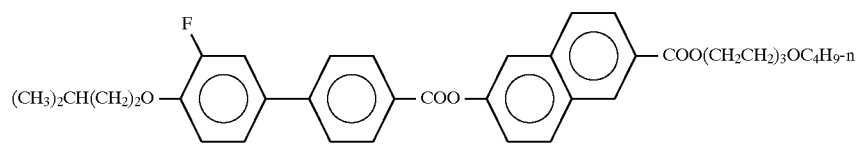
Exemplified compound 362
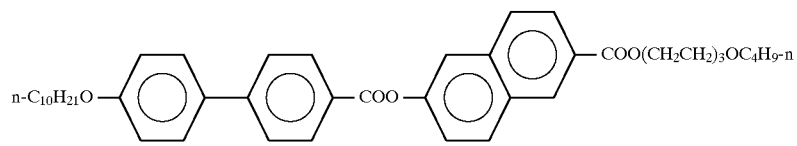
Exemplified compound 363
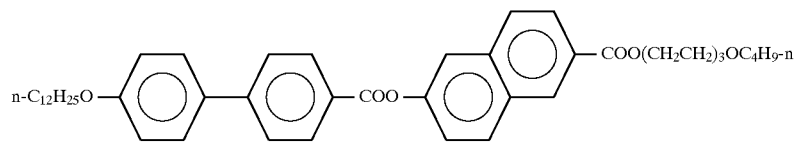
Exemplified compound 364
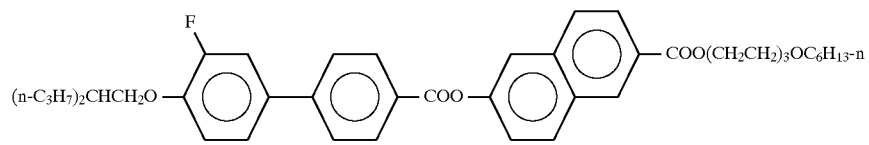
Exemplified compound 365
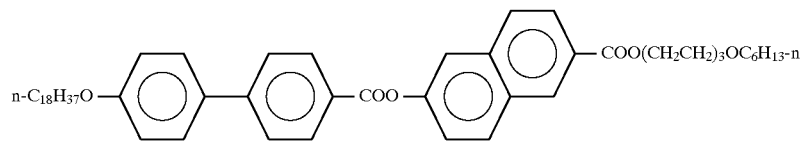
Exemplified compound 366
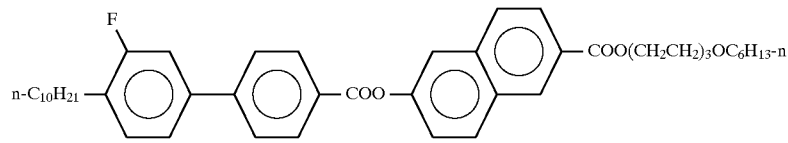
Exemplified compound 367
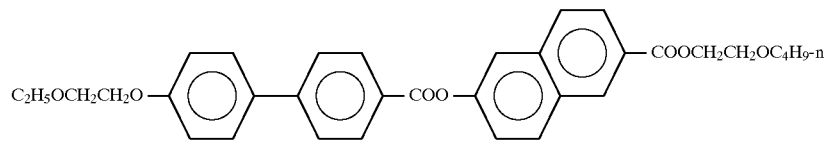
Exemplified compound 368

-continued
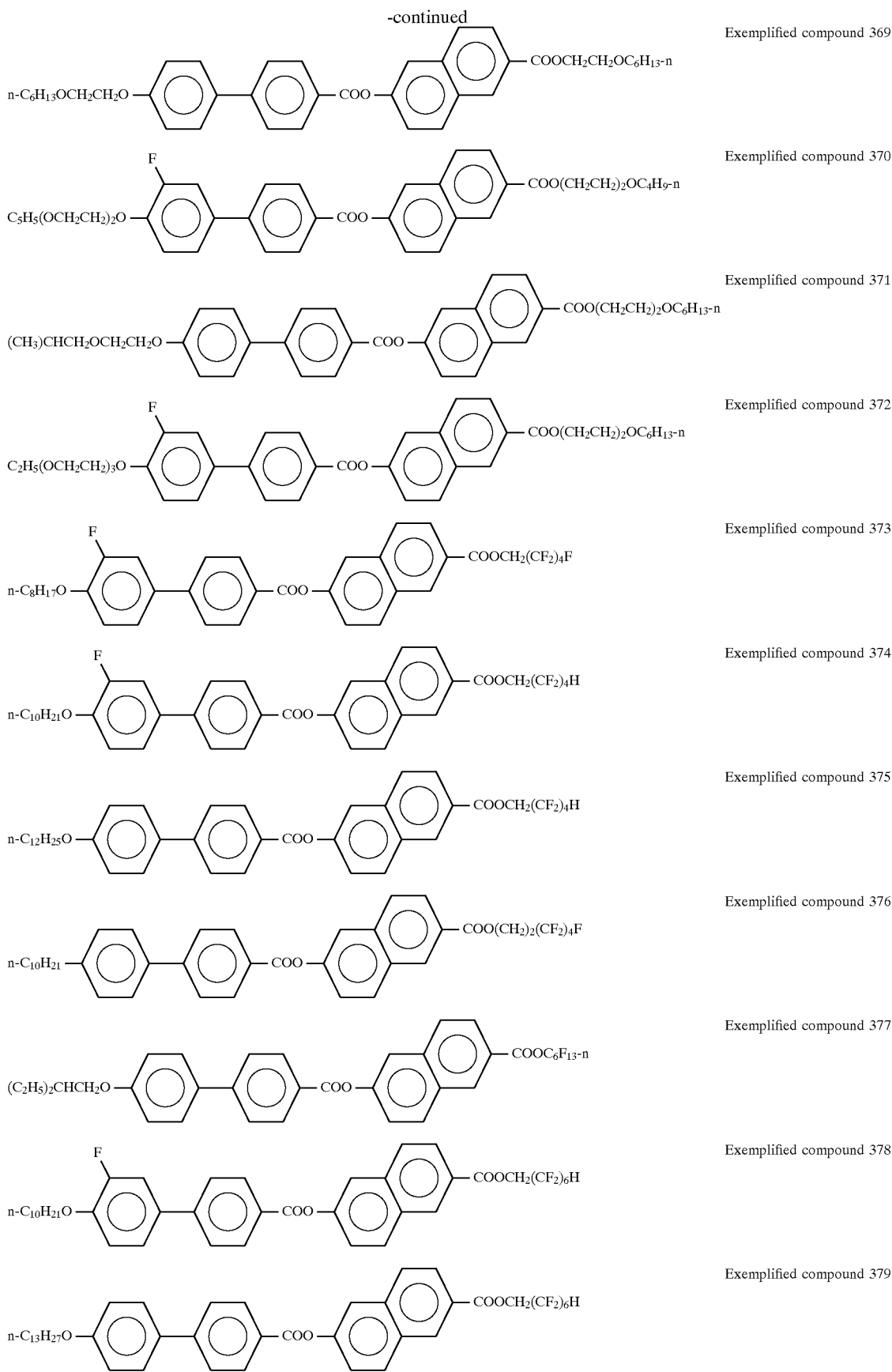

-continued
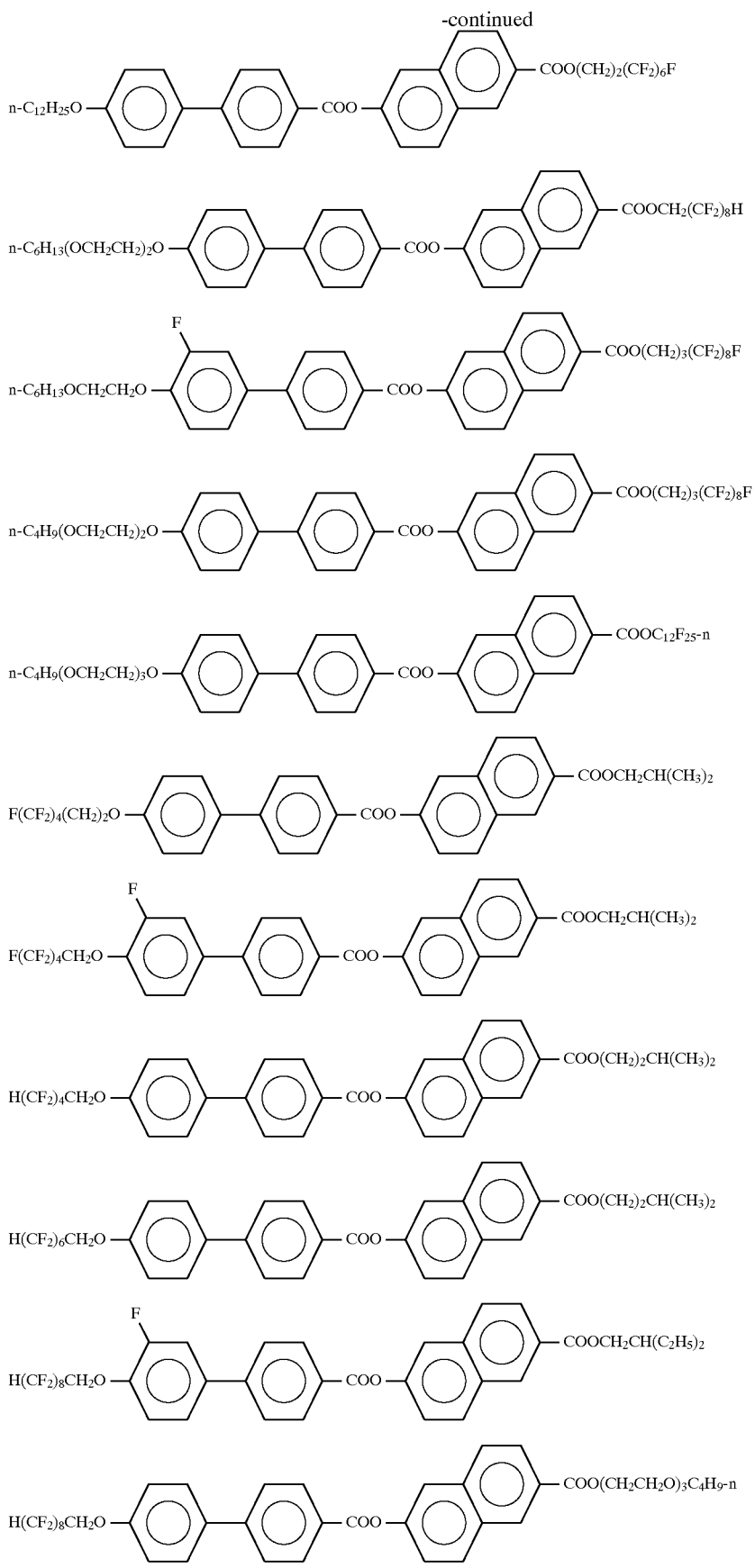
Exemplified compound 380
Exemplified compound 381
Exemplified compound 382
Exemplified compound 383
Exemplified compound 384
Exemplified compound 385
Exemplified compound 386
Exemplified compound 387
Exemplified compound 388
Exemplified compound 389
Exemplified compound 390

-continued
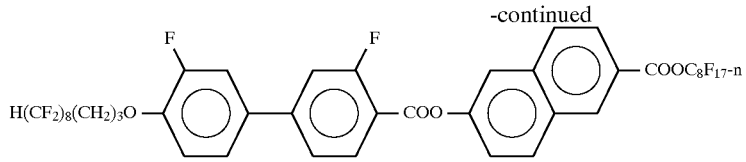 Exemplified compound 391
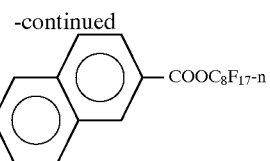 Exemplified compound 392
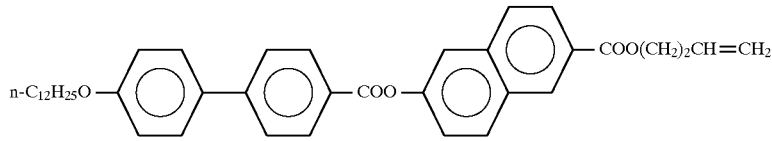 Exemplified compound 393
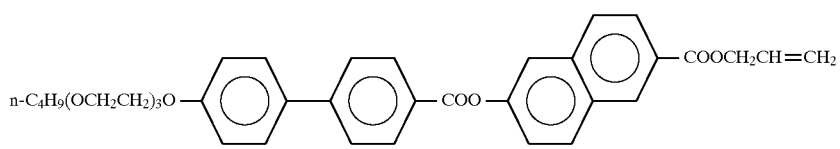 Exemplified compound 394
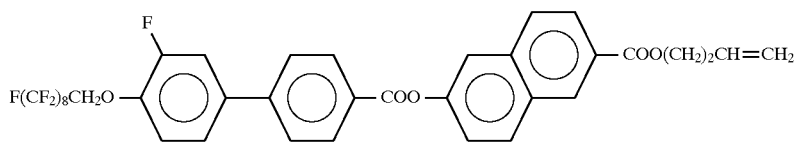 Exemplified compound 395
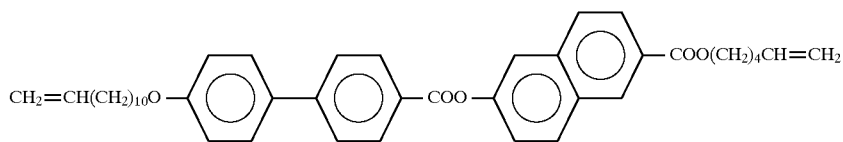 Exemplified compound 396
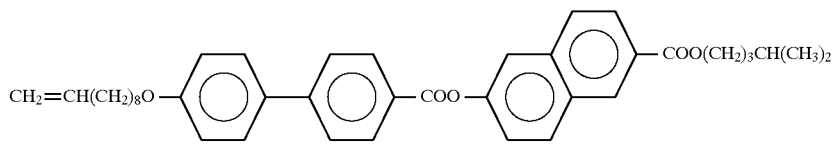 Exemplified compound 397
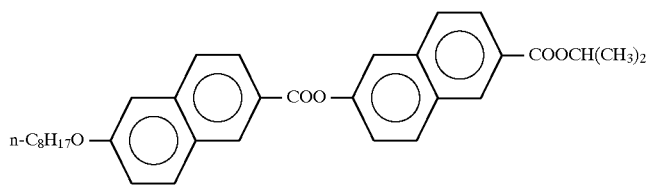 Exemplified compound 398
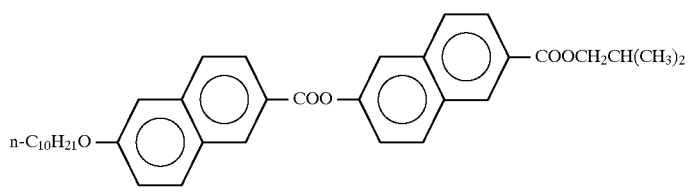 Exemplified compound 399
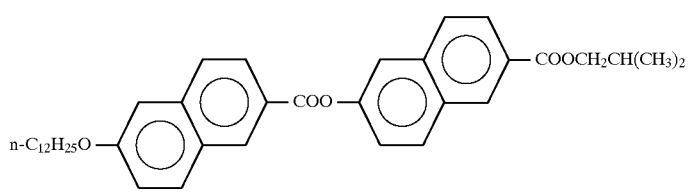 Exemplified compound 400
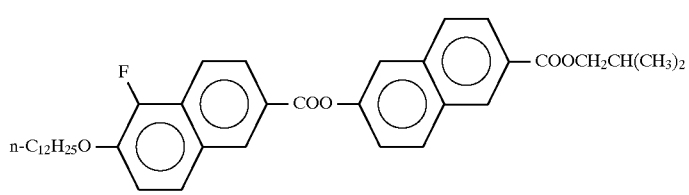

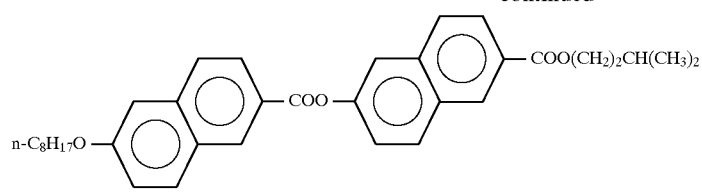
Exemplified compound 401
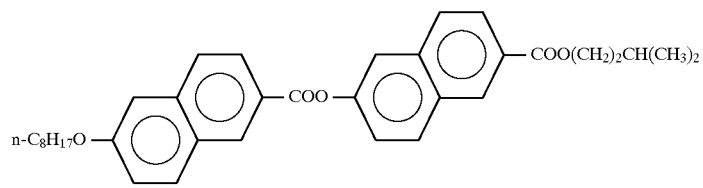
Exemplified compound 402
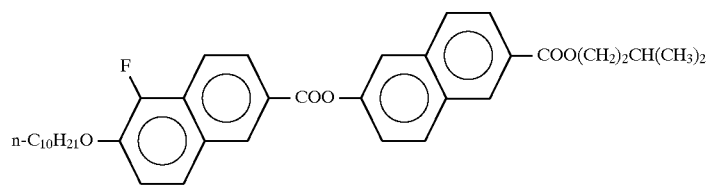
Exemplified compound 403
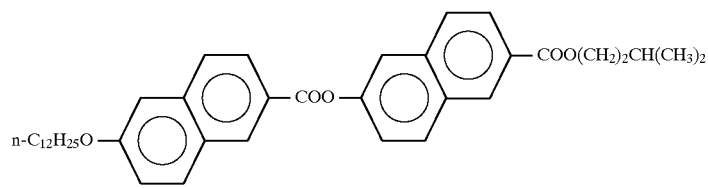
Exemplified compound 404
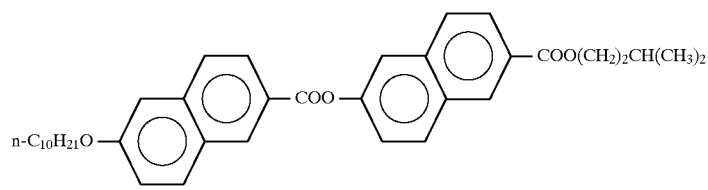
Exemplified compound 405
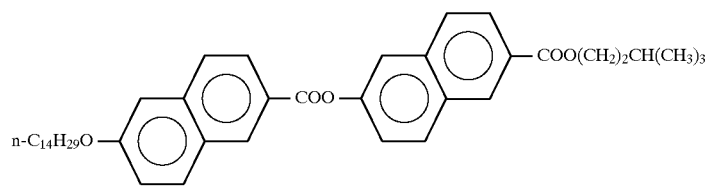
Exemplified compound 406
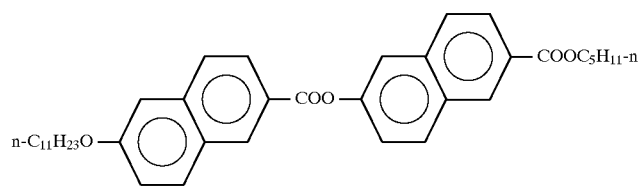
Exemplified compound 407
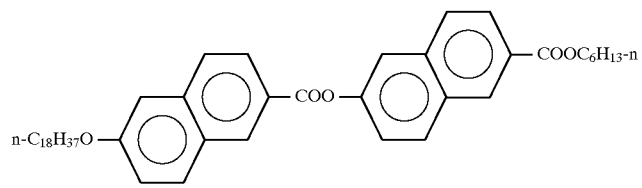
Exemplified compound 408
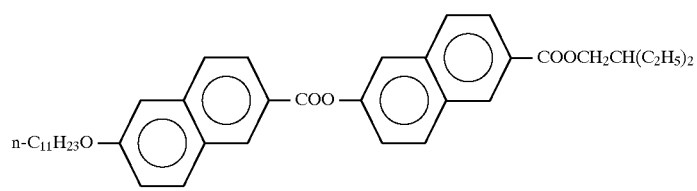

-continued
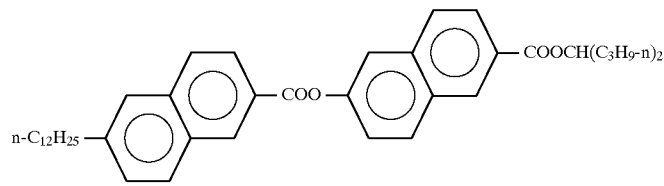
Exemplified compound 409
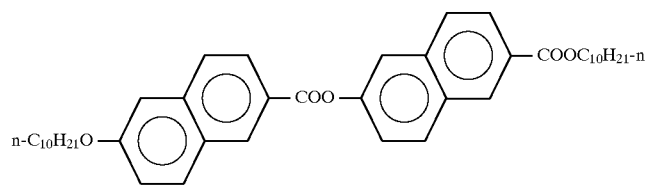
Exemplified compound 410
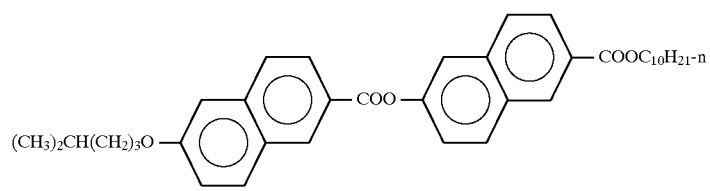
Exemplified compound 411
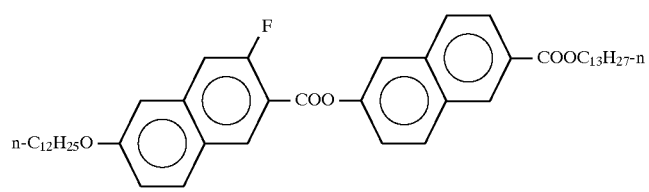
Exemplified compound 412
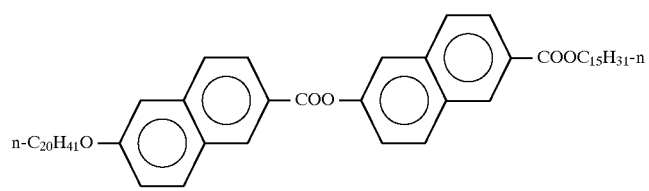
Exemplified compound 413
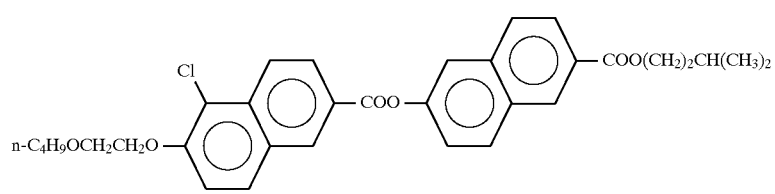
Exemplified compound 414
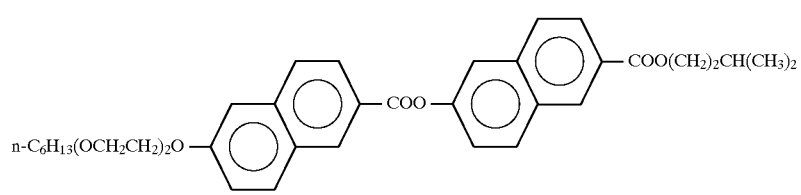
Exemplified compound 415
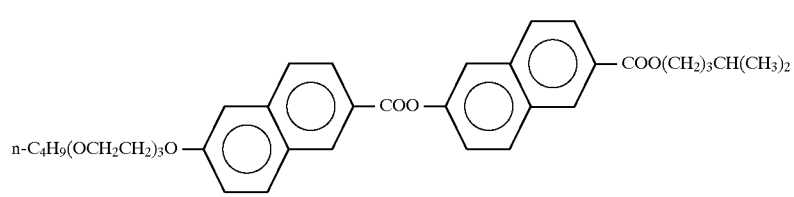
Exemplified compound 416

-continued
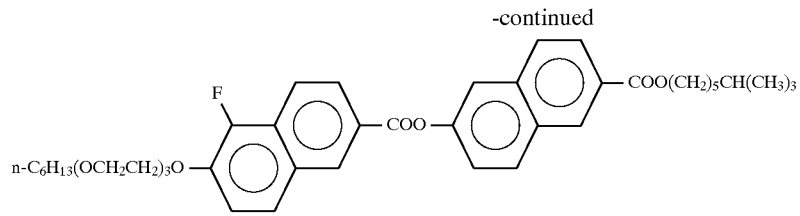
Exemplified compound 417
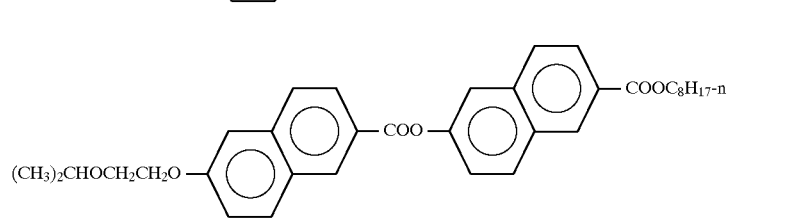
Exemplified compound 418
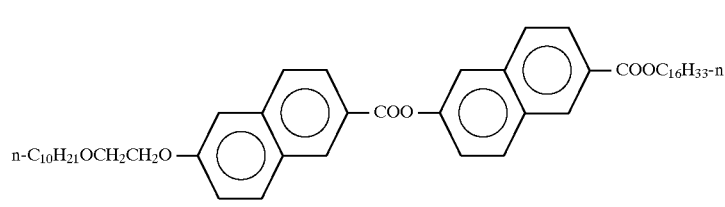
Exemplified compound 419
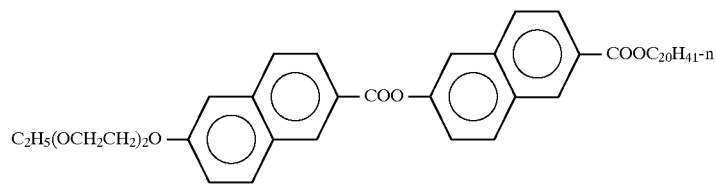
Exemplified compound 420
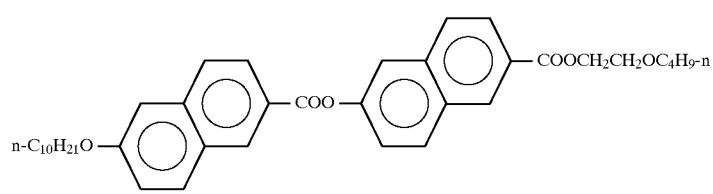
Exemplified compound 421
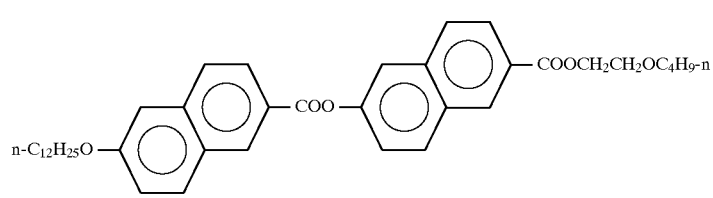
Exemplified compound 422
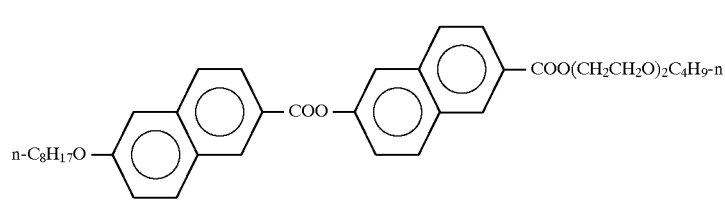
Exemplified compound 423
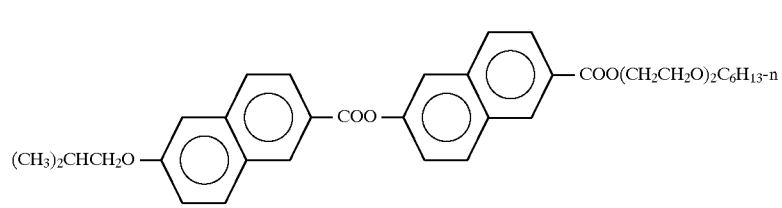
Exemplified compound 424

-continued
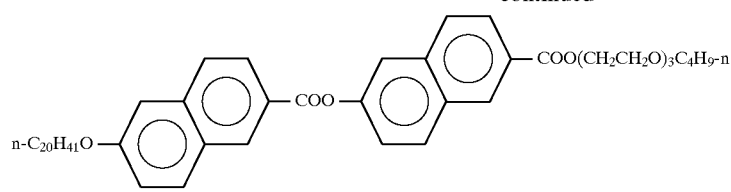
Exemplified compound 425
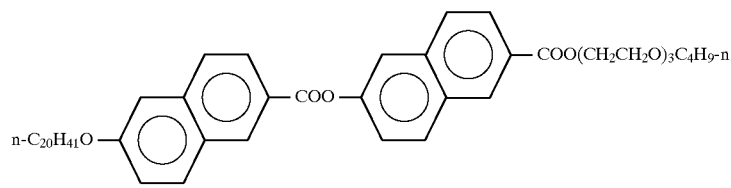
Exemplified compound 426
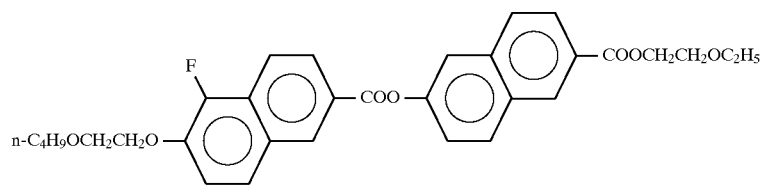
Exemplified compound 427
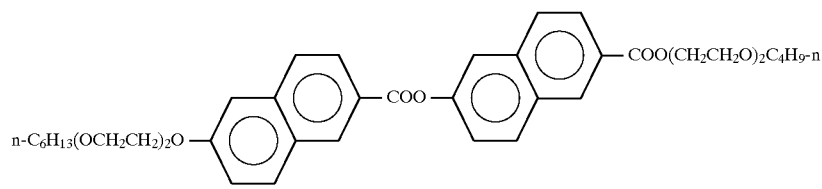
Exemplified compound 428
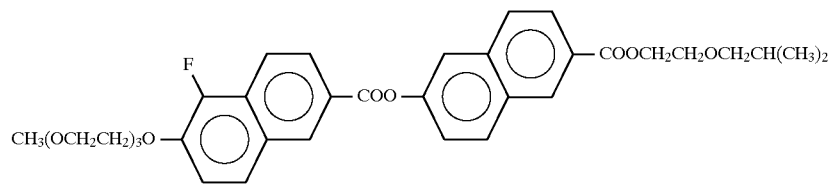
Exemplified compound 429
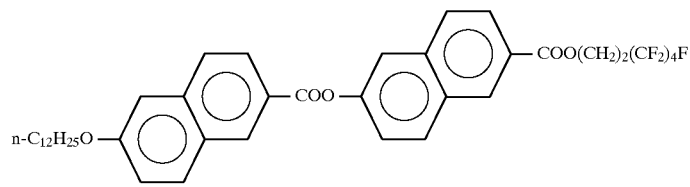
Exemplified compound 430
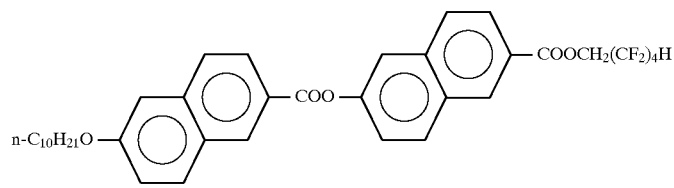
Exemplified compound 431
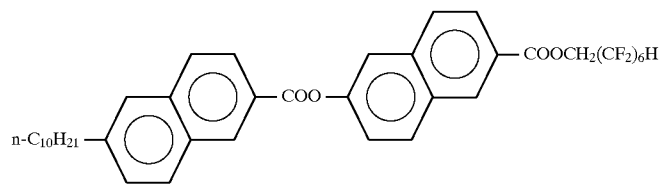
Exemplified compound 432
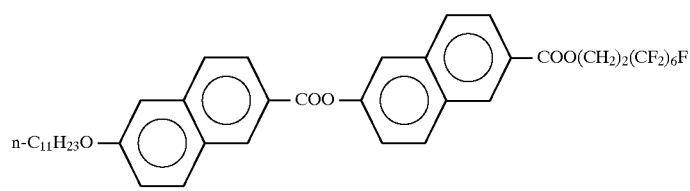

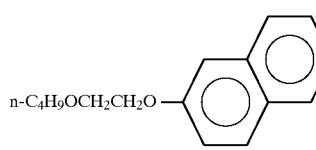
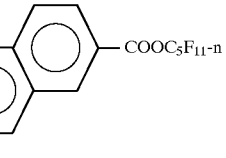
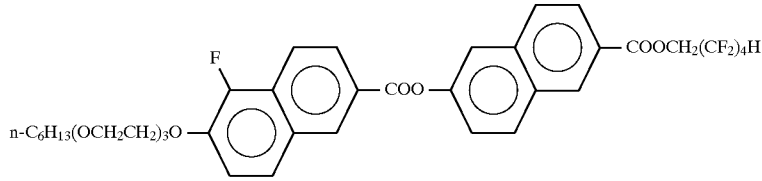
Exemplified compound 433
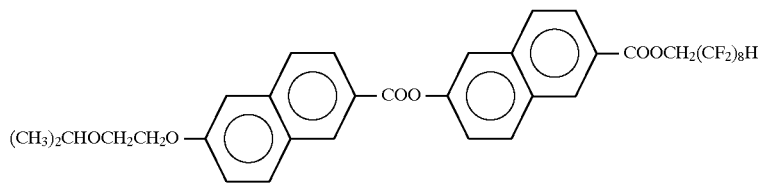
Exemplified compound 434
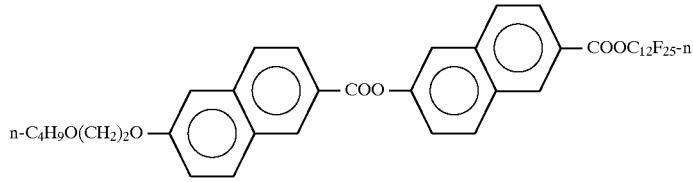
Exemplified compound 435
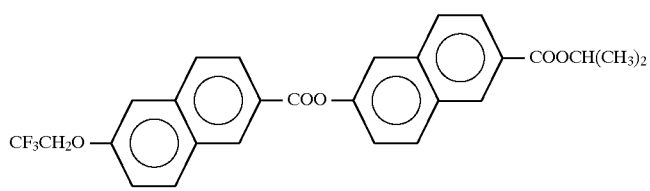
Exemplified compound 436
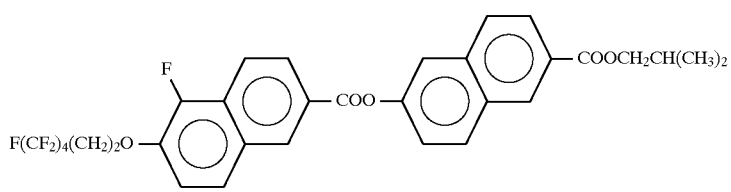
Exemplified compound 437
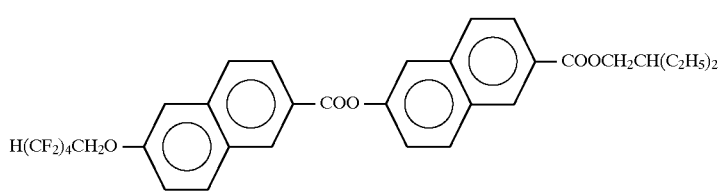
Exemplified compound 438
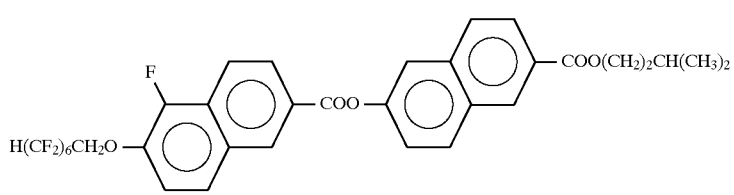
Exemplified compound 439
Exemplified compound 440

-continued
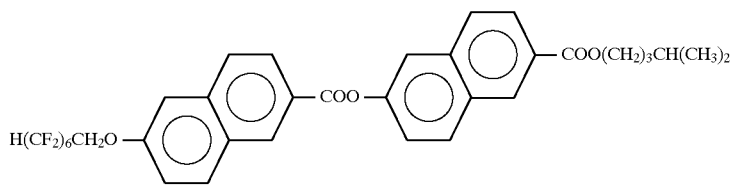
Exemplified compound 441
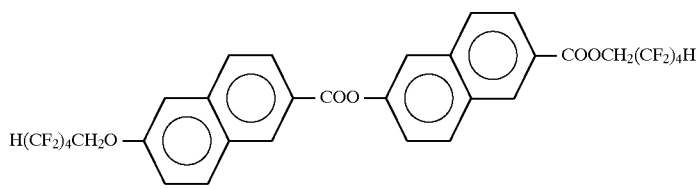
Exemplified compound 442
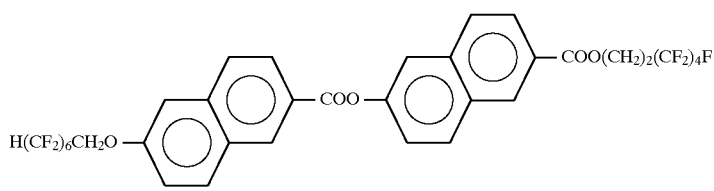
Exemplified compound 443
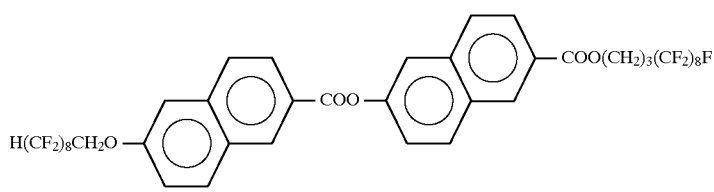
Exemplified compound 444
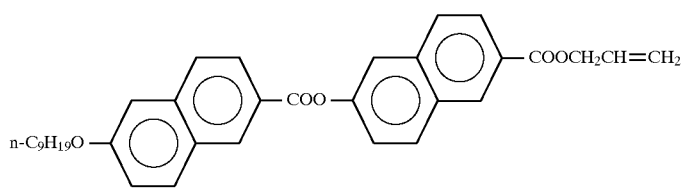
Exemplified compound 445
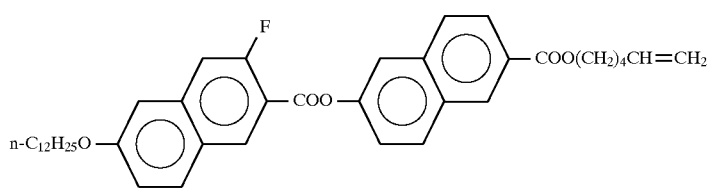
Exemplified compound 446
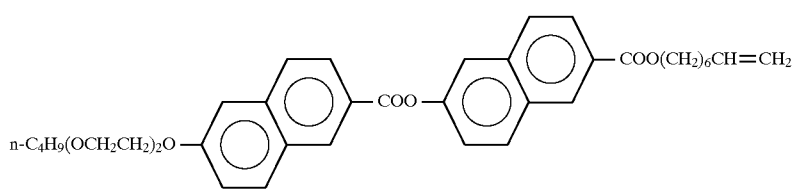
Exemplified compound 447
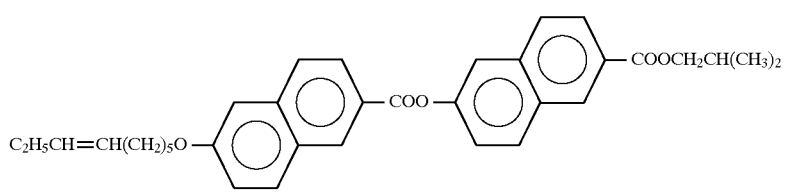
Exemplified compound 448

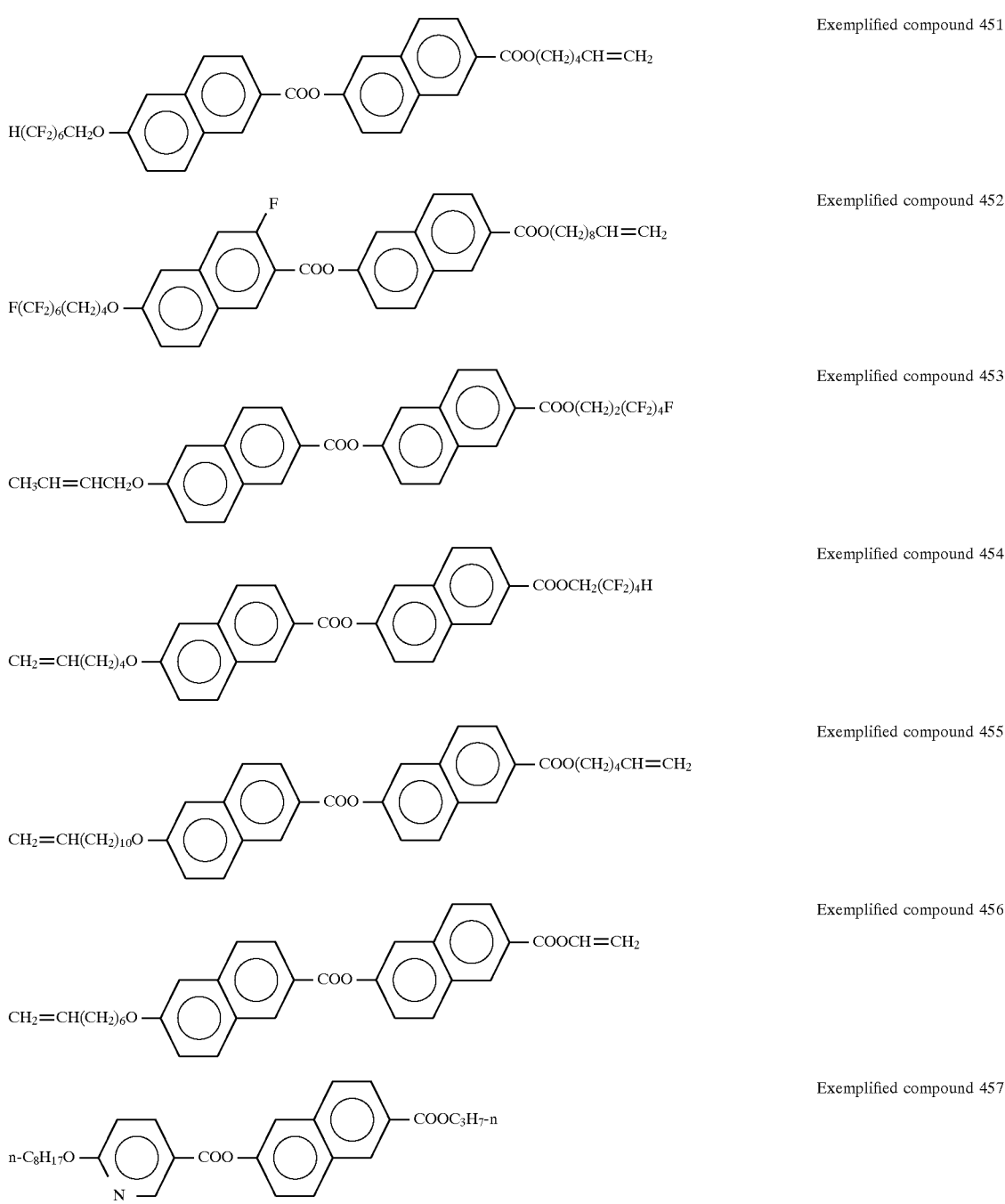

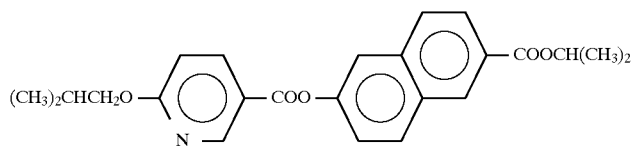
Exemplified compound 458
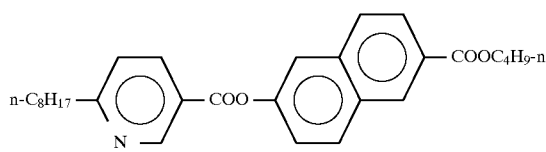
Exemplified compound 459
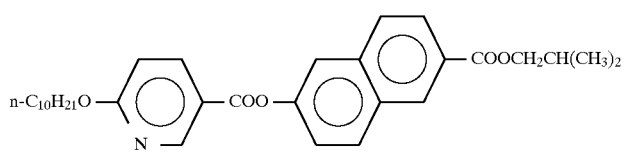
Exemplified compound 460
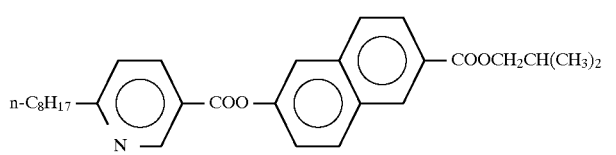
Exemplified compound 461
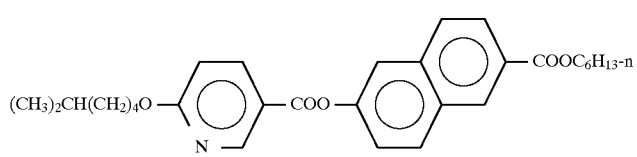
Exemplified compound 462
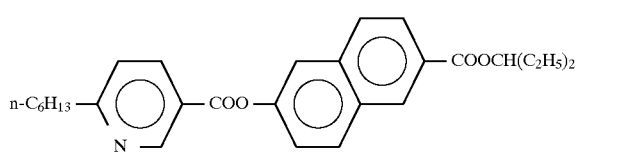
Exemplified compound 463
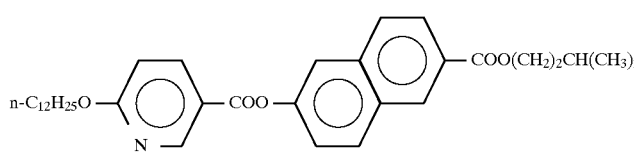
Exemplified compound 464
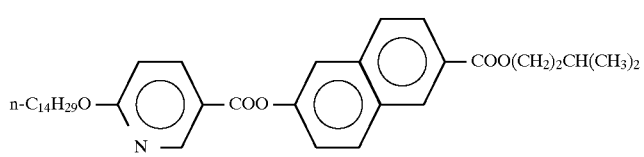
Exemplified compound 465
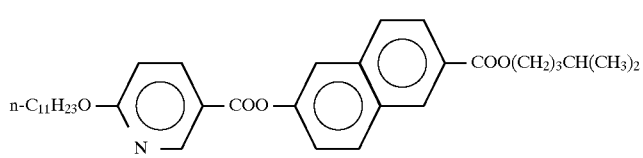
Exemplified compound 466
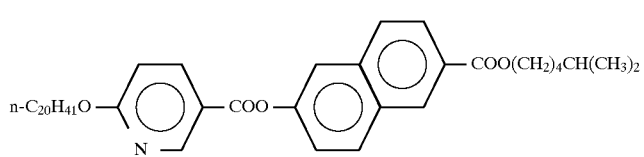
Exemplified compound 467

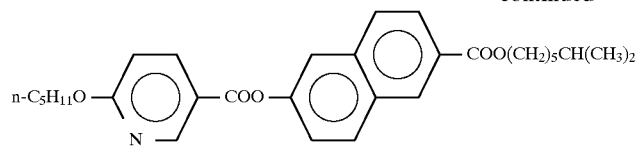
Exemplified compound 468
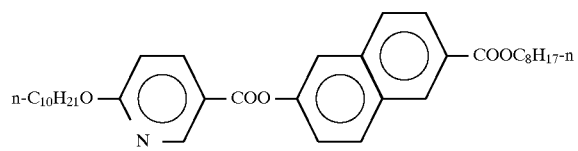
Exemplified compound 469
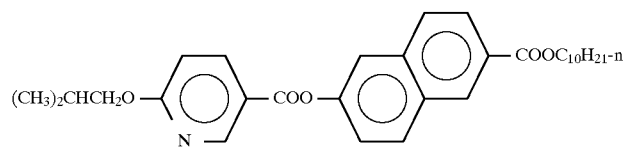
Exemplified compound 470
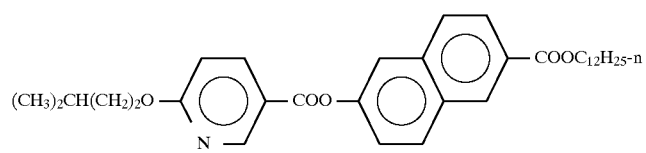
Exemplified compound 471
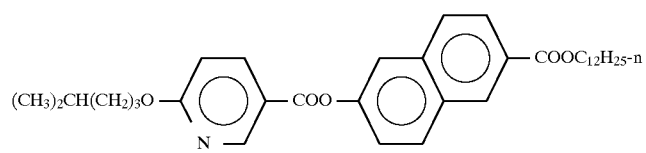
Exemplified compound 472
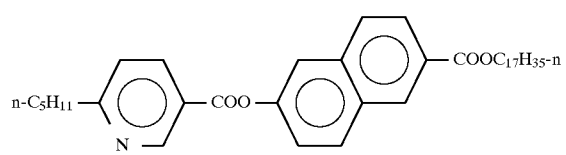
Exemplified compound 473
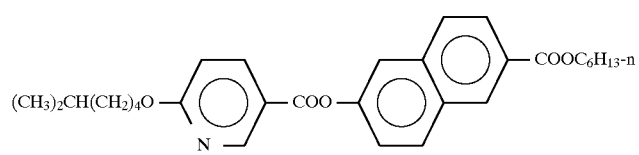
Exemplified compound 474
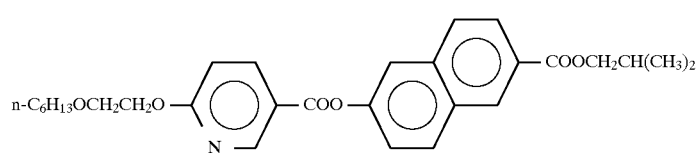
Exemplified compound 475
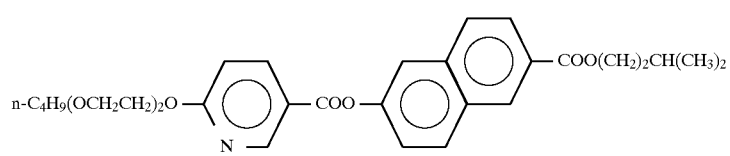
Exemplified compound 476
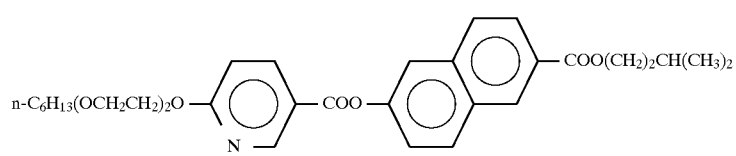
Exemplified compound 477

-continued
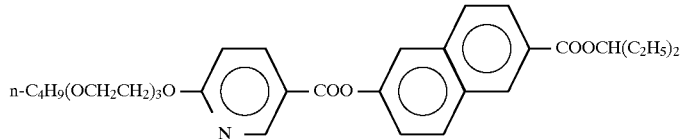
Exemplified compound 478
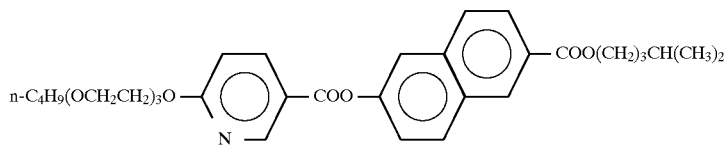
Exemplified compound 479
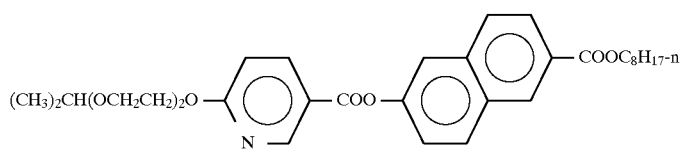
Exemplified compound 480
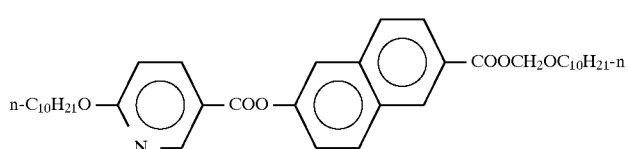
Exemplified compound 481
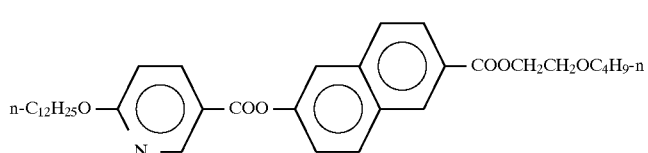
Exemplified compound 482
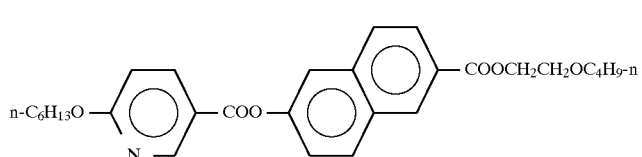
Exemplified compound 483
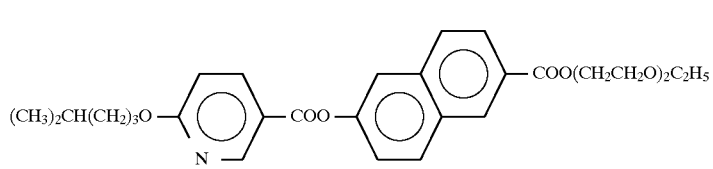
Exemplified compound 484
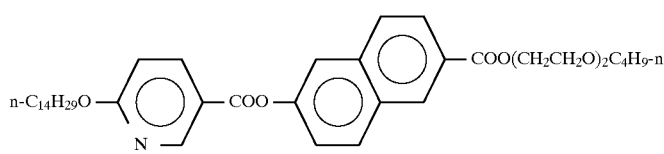
Exemplified compound 485
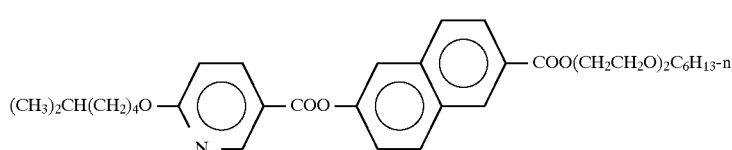
Exemplified compound 486
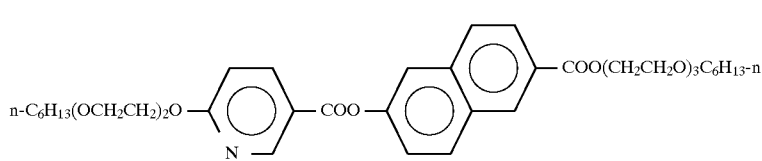
Exemplified compound 487

-continued
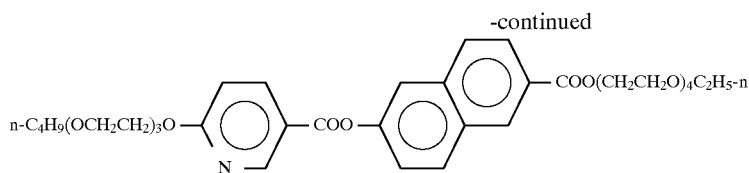
Exemplified compound 488
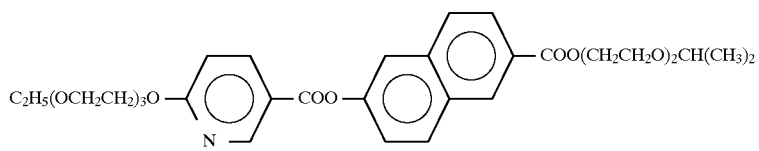
Exemplified compound 489
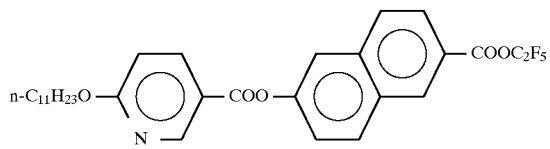
Exemplified compound 490
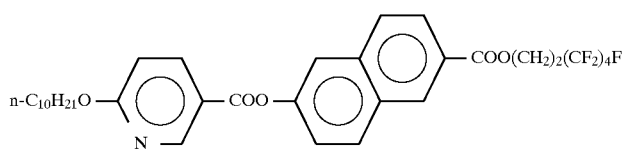
Exemplified compound 491
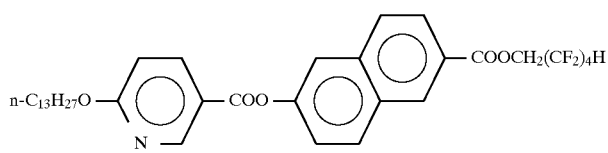
Exemplified compound 492
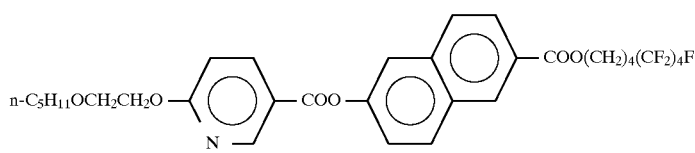
Exemplified compound 493
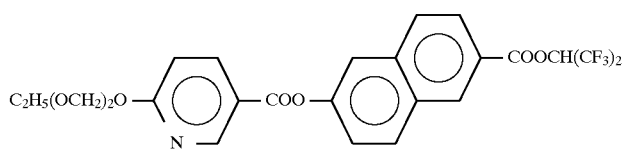
Exemplified compound 494
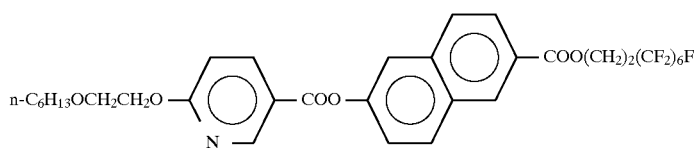
Exemplified compound 495
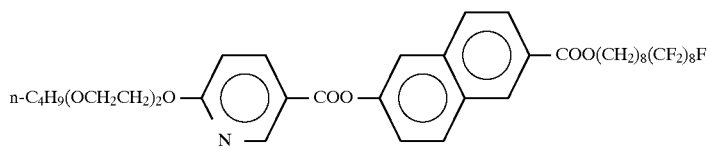
Exemplified compound 496
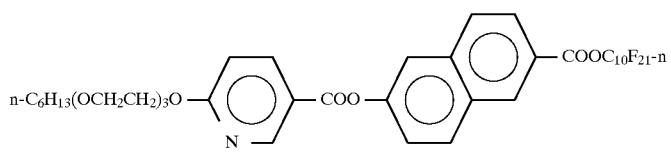
Exemplified compound 497

-continued
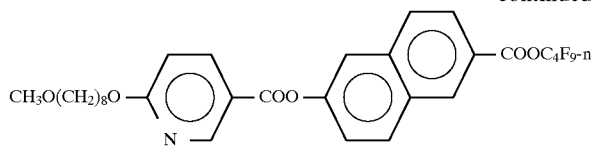
Exemplified compound 498
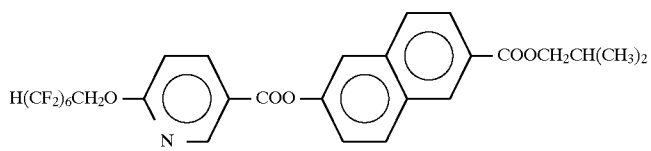
Exemplified compound 499
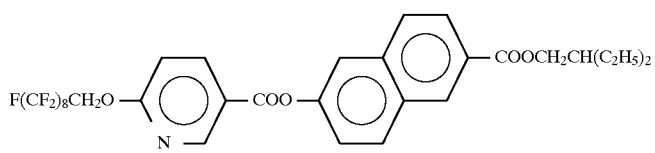
Exemplified compound 500
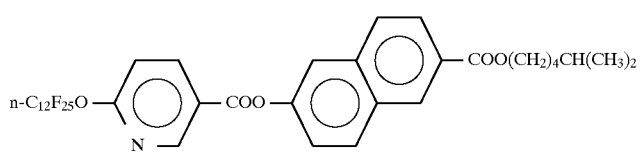
Exemplified compound 501
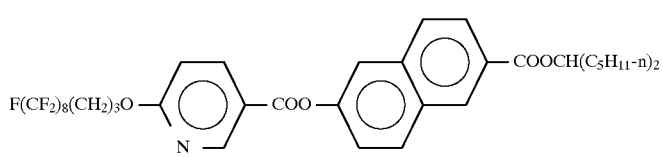
Exemplified compound 502
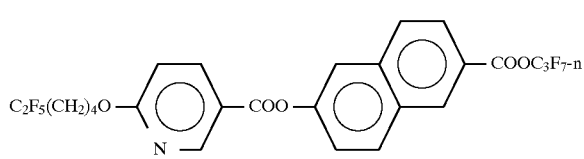
Exemplified compound 503
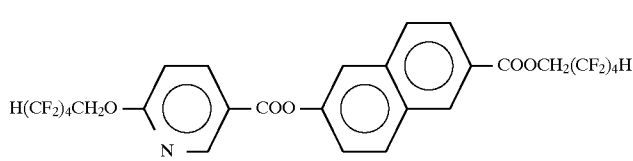
Exemplified compound 504
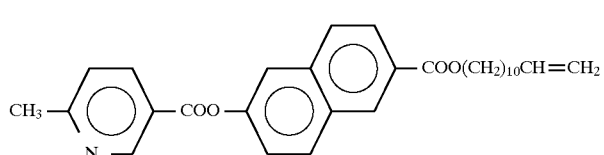
Exemplified compound 505
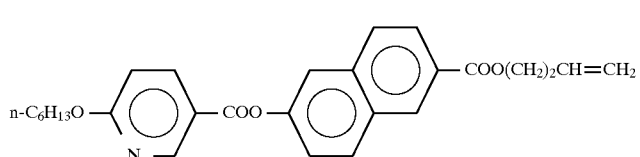
Exemplified compound 506
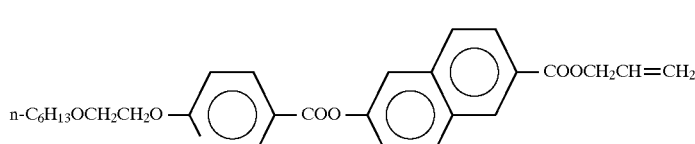
Exemplified compound 507

-continued
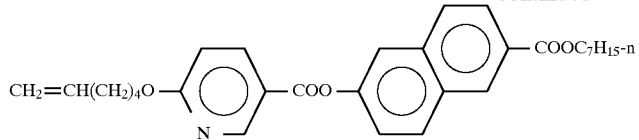
Exemplified compound 508
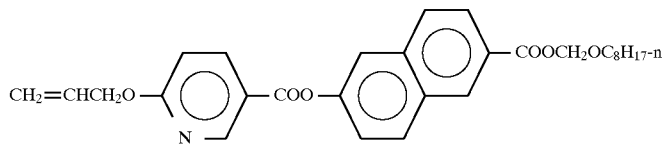
Exemplified compound 509
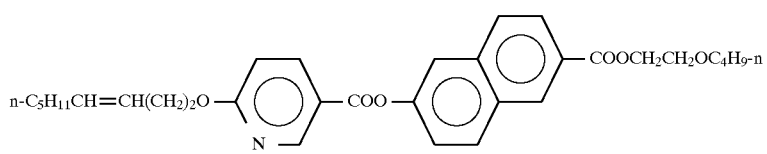
Exemplified compound 510
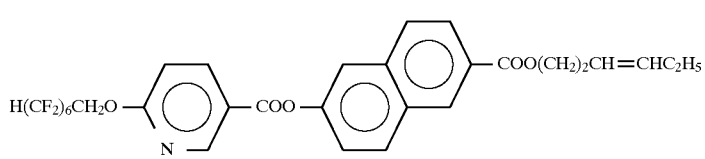
Exemplified compound 511
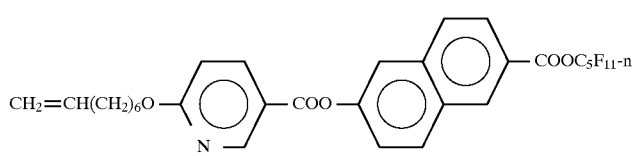
Exemplified compound 512
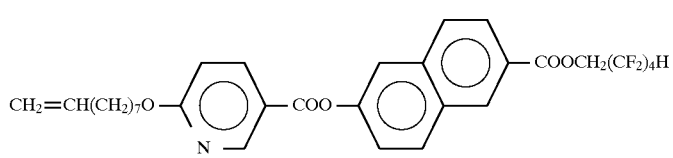
Exemplified compound 513
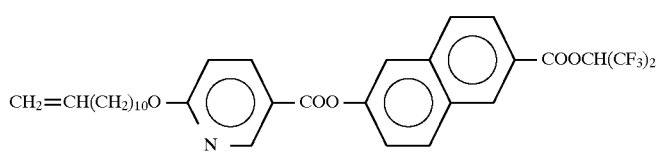
Exemplified compound 514
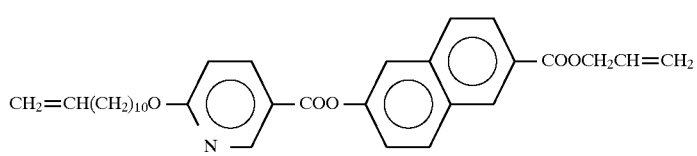
Exemplified compound 515
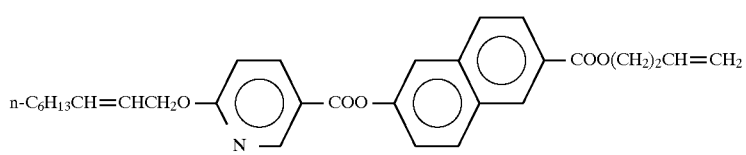
Exemplified compound 516
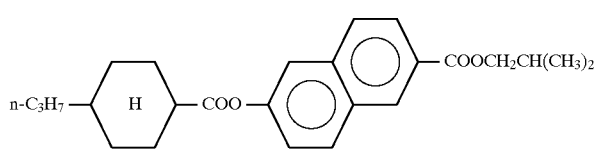
Exemplified compound 517
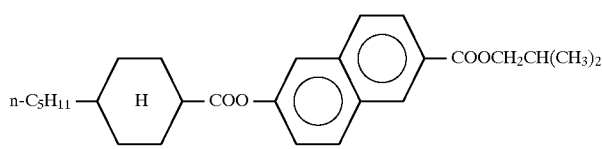
Exemplified compound 518

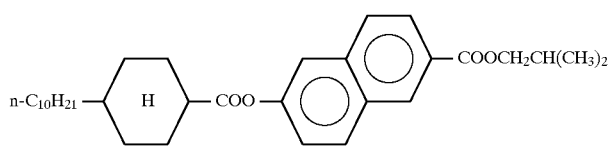
Exemplified compound 519
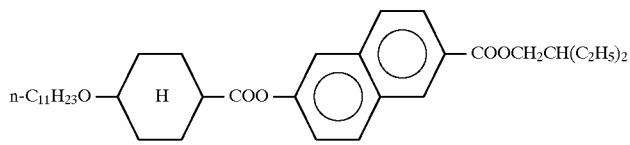
Exemplified compound 520
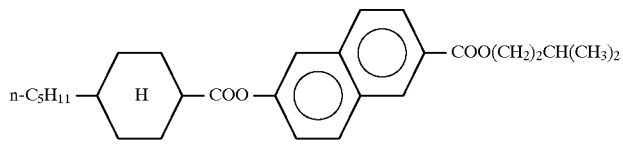
Exemplified compound 521
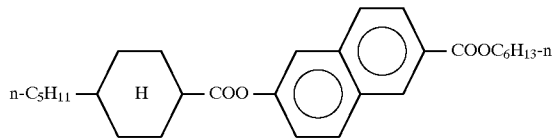
Exemplified compound 522
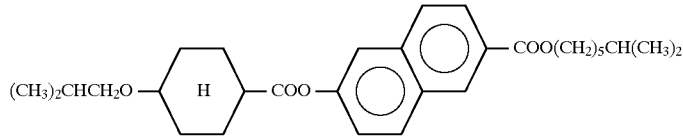
Exemplified compound 523
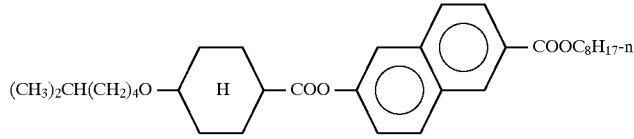
Exemplified compound 524
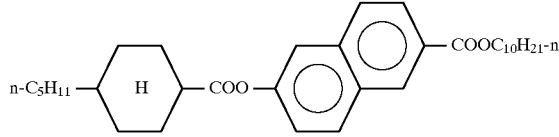
Exemplified compound 525
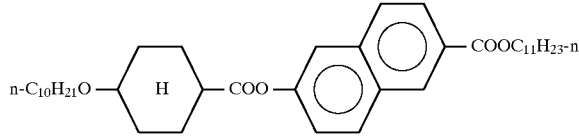
Exemplified compound 526
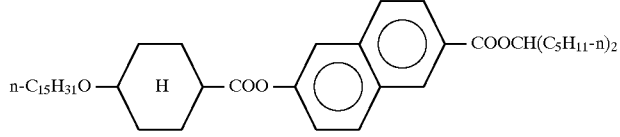
Exemplified compound 527
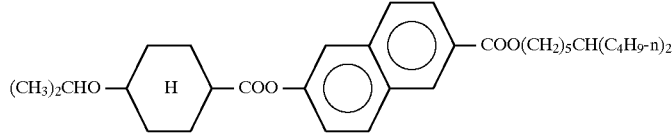
Exemplified compound 528
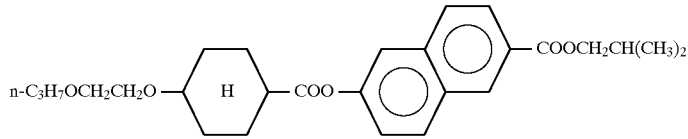
Exemplified compound 529

-continued
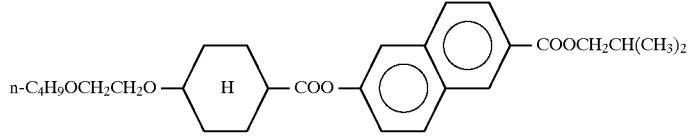
Exemplified compound 530
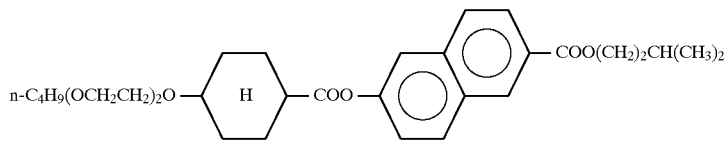
Exemplified compound 531
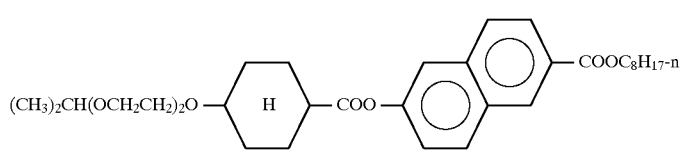
Exemplified compound 532
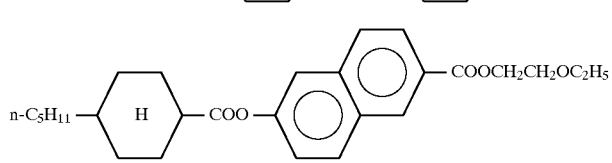
Exemplified compound 533
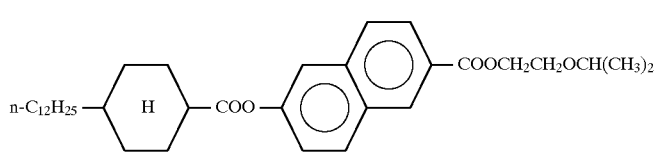
Exemplified compound 534
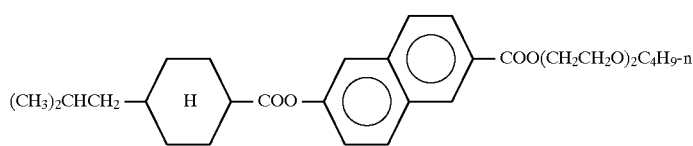
Exemplified compound 535
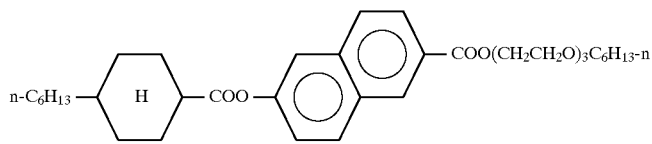
Exemplified compound 536
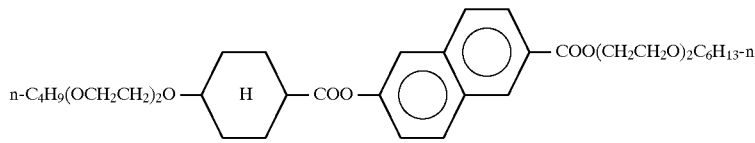
Exemplified compound 537
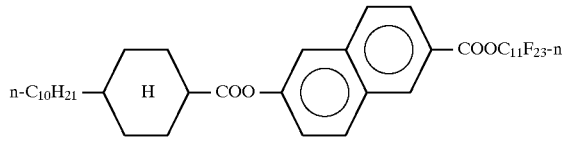
Exemplified compound 538
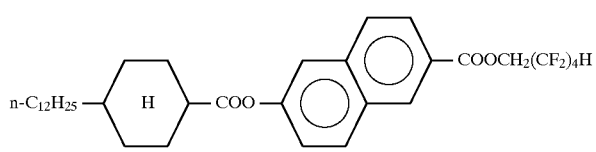
Exemplified compound 539
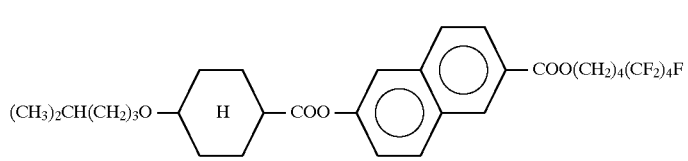
Exemplified compound 540

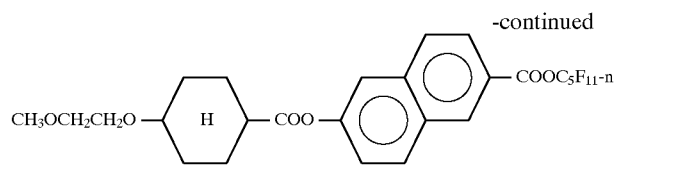
Exemplified compound 541
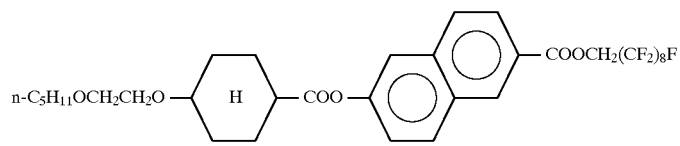
Exemplified compound 542
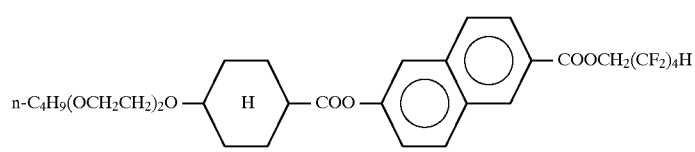
Exemplified compound 543
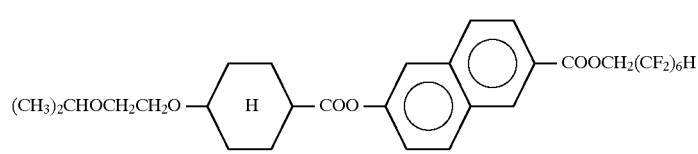
Exemplified compound 544
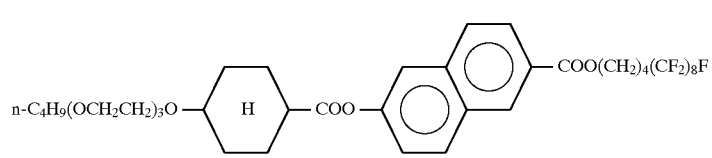
Exemplified compound 545
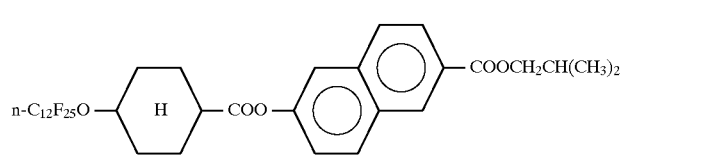
Exemplified compound 546
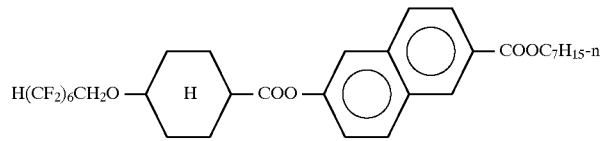
Exemplified compound 547
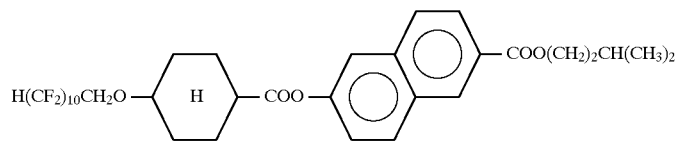
Exemplified compound 548
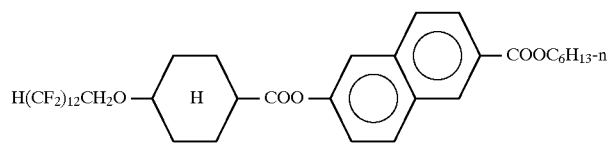
Exemplified compound 549
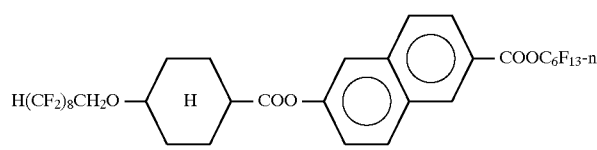
Exemplified compound 550
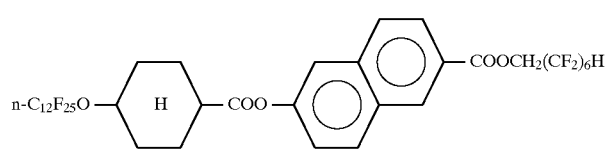
Exemplified compound 551

-continued
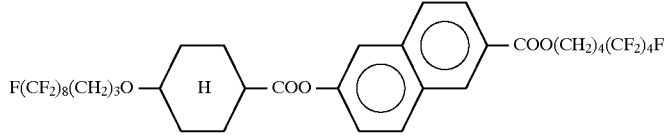
Exemplified compound 552
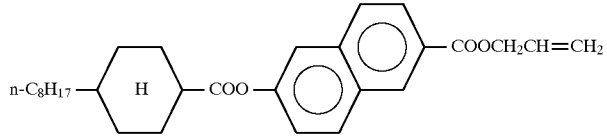
Exemplified compound 553
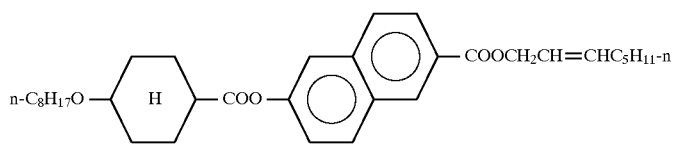
Exemplified compound 554
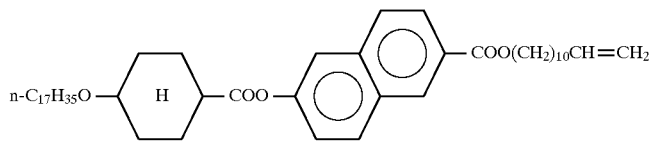
Exemplified compound 555
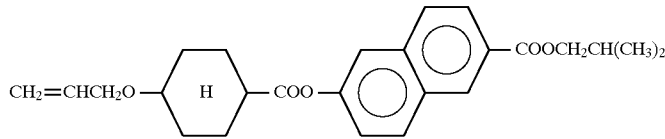
Exemplified compound 556
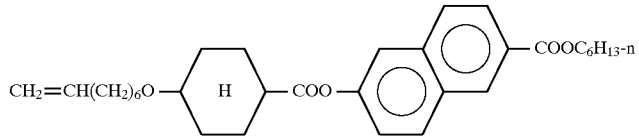
Exemplified compound 557
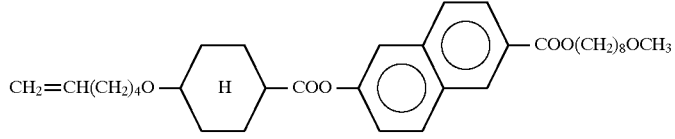
Exemplified compound 558
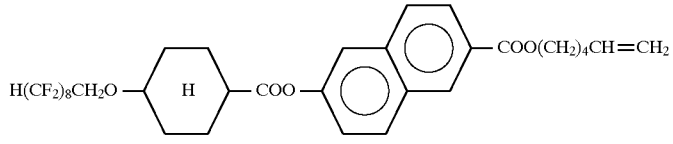
Exemplified compound 559
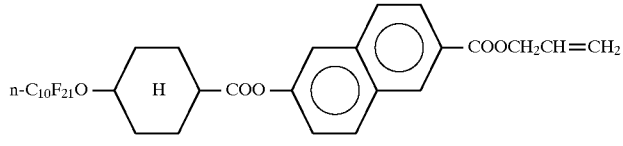
Exemplified compound 560
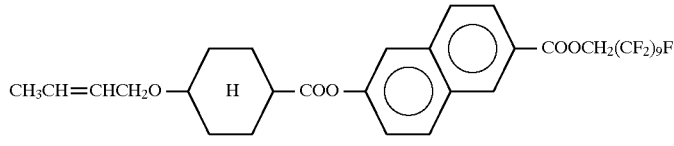
Exemplified compound 561
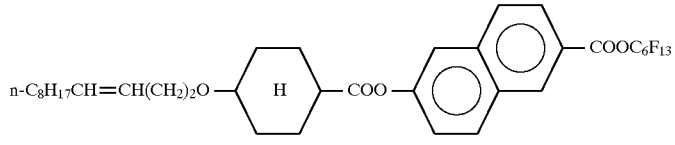
Exemplified compound 562

-continued

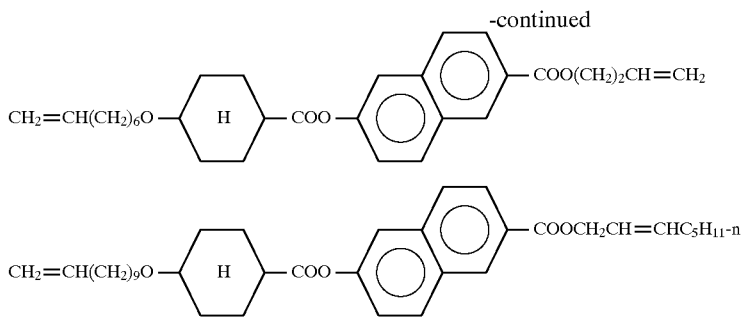

Exemplified compound 563

Exemplified compound 564

The compound represented by Formula (1) can be produced typically by the following method.

That is, the above compound can be produced by carrying out esterification using a compound represented by Formula (3a) and a compound represented by Formula (4):

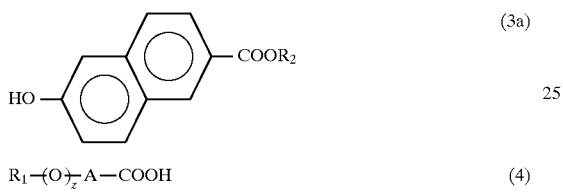

wherein $R_1$, $R_2$, A and z are synonymous with those described above.

There can be applied as a method for carrying out the esterification, known methods, for example, (1) a method in which the compound represented by Formula (3a) is reacted with the compound represented by Formula (4) by the action of a condensing agent such as N,N'-dicyclohexylcarbodiimide (DCC) in the presence of a catalyst such as, for example, 4-pyrrolidinopyridine and 4-N,N-dimethylaminopyridine, or (2) a method in which the compound represented by Formula (4) is reacted with thionyl chloride or oxalyl chloride to prepare the halide, and then the compound represented by Formula (3a) is reacted therewith.

Some of the compounds represented by Formula (4) are commercially available. Further, they can be produced by known methods [for example, J. Chem. Soc., 1874 (1935), J. Chem. Soc., 2556 (1954), J. Chem. Soc., 1412 (1955), J. Chem. Soc., 393 (1957) and J. Chem. Soc., 1545 (1959)].

That is, a 4-alkoxybenzoic acid derivative can be produced by reacting, for example, a 4-hydroxybenzoic acid derivative with an alkylating agent such as an alkyl halide and an alkyl tosylate in the presence of a base.

Further, a 4-alkoxybiphenyl-4'-carboxylic acid derivative can be produced by reacting a 4-hydroxybiphenyl-4'-carboxylic acid derivative with an alkylating agent such as an alkyl halide and an alkyl tosylate in the presence of a base.

The compounds represented by Formulas (3a) or (3b) can be produced typically through the following steps:

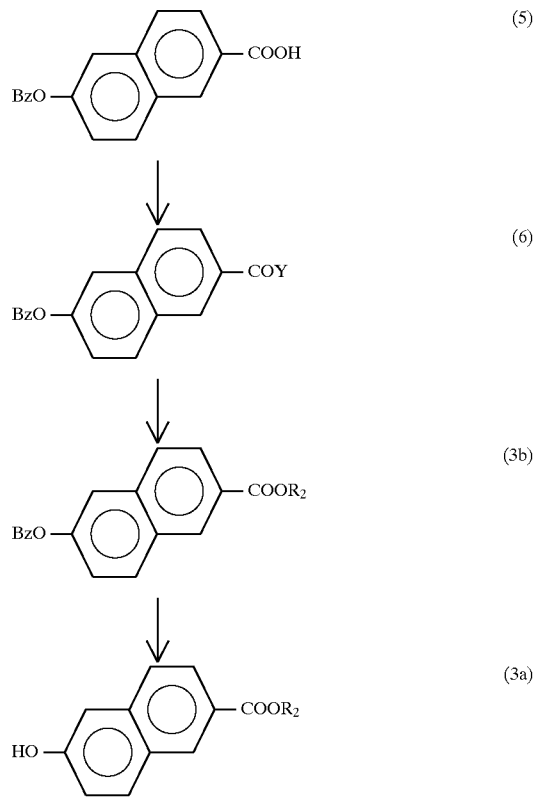

wherein $R_2$ is synonymous with that described above; Y represents a halogen atom; and Bz represents a benzyl group.

That is, 2-benzyloxy-6-naphthoic acid represented by Formula (5) produced by benzylation of 2-hydroxy-6-naphthoic acid with a benzyl halide is reacted with thionyl chloride or oxalyl chloride to produce an acid halide represented by Formula (6). Then, the acid halide represented by Formula (6) is reacted with an alcoholic compound represented by Formula (7):

wherein $R_2$ is synonymous with that described above, whereby the compound represented by Formula (3b) can be produced.

Further, the compound represented by Formula (3b) can be produced as well by reacting 2-benzyloxy-6-naphthoic acid represented by Formula (5) with the alcoholic compound represented by Formula (7) by the action of a condensing agent such as N,N'-dicyclohexylcarbodiimide (DCC) in the presence of a catalyst such as, for example, 4-pyrrolidinopyridine and 4-N,N-dimethylaminopyridine.

Further, the compound represented by Formula (3b) can be produced as well by reacting 2-benzyloxy-6-naphthoic acid represented by Formula (5) with an alkylating agent represented by Formula (8) in the presence of an aprotic polar solvent and an alkaline metal salt:

$R_2$—W     (8)

wherein $R_2$ is synonymous with that described above, and W represents a halogen atom or an leaving group such as an arylsulfonyloxy group.

Then, the compound represented by Formula (3a) can be produced by hydrogenation (debenzylation) of the compound represented by Formula (3b).

The hydrogenation can be carried out by known methods. That is, the hydrogenation can be done by carrying out hydrogenation in an organic solvent (for example, alcoholic solvents and ester solvents) at a pressure of atmospheric pressure to about 50 kg/cm$^2$ in the presence of a catalyst prepared by carrying metals such as, for example, Pd, Pt, Rh, Co and Ni on activated carbon, alumina, barium sulfate, or the like. In general, the hydrogenation is carried out at 0° to 200° C., preferably 10° to 150° C.

Further, the compound represented by Formula (3a) can be produced as well by reacting 2-hydroxy-6-naphthoic acid with an alkylating agent represented by Formula (8) in the presence of an aprotic polar solvent and an alkaline metal salt.

2-Hydroxy-6-naphthoic acid can be produced by known methods [for example, a method described in J. Chem. Soc., 678 (1954)].

Among the naphthalene compounds represented by (3a) and (3b), the naphthalene compounds represented by Formula (2), that is, the compounds represented by Formula (2a) and (2b) are novel compounds, and the present invention provides these compounds.

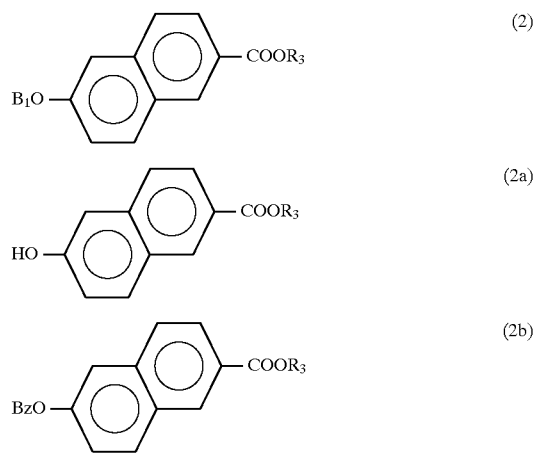

In Formula (2), $B_1$ represents a hydrogen atom or a benzyl group, and in formula (2b), Bz represents a benzyl group.

In Formulas (2a) and (2b), $R_3$ represents a branched alkyl group having no asymmetric carbon atoms and having 3 to 20 carbon atoms which have no asymmetric carbon atoms, or a linear or branched halogenated alkyl group having 1 to 20 carbon atoms, or an alkoxyalkyl group having 2 to 20 carbon atoms or an alkenyl group having 2 to 20 carbon atoms which may be substituted with halogen atoms and have no asymmetric carbon atoms, preferably the branched alkyl group represented by Formula (II), the alkoxyalkyl group represented by Formula (III), or the halogenated alkyl group represented by Formula (IV), (V) or (VI), each described above.

There can be given as the concrete examples of $R_3$, the branched alkyl groups, halogenated alkyl groups, alkoxyalkyl groups, halogenated alkoxyalkyl groups, and alkenyl groups, each given as the concrete examples of $R_1$ and $R_2$ in Formula (1).

Many of the compounds thus prepared and represented by Formula (1) has intrinsically liquid crystallinity and is useful for constituting a liquid crystal composition and a liquid crystal element using said liquid crystal composition.

The naphthalene compounds of the present invention include compounds showing liquid crystallinity in itself and compounds showing no liquid crystallinity in itself. Further, the naphthalene compounds showing liquid crystallinity include compounds showing a smectic C phase and compounds showing liquid crystallinity but no smectic C phase. These compounds each can effectively be used as components for liquid crystal compositions.

Next, the liquid crystal composition of the present invention will be explained.

In general, a liquid crystal composition comprises two or more kinds of components. The liquid crystal composition of the present invention contains at least one naphthalene compound of the present invention as an essential component.

The naphthalene compound of the present invention used for the liquid crystal composition of the present invention includes naphthalene compounds showing no liquid crystallinity, compounds showing a smectic C phase, and naphthalene compounds showing liquid crystallinity but no smectic C phase.

The liquid crystal composition of the present invention shall not specifically be restricted and includes, for example, liquid crystal compositions showing a smectic phase and liquid crystal compositions showing a chiral smectic phase, preferably liquid crystal compositions showing smectic C, F, G, H and I phases, and liquid crystal compositions showing chiral smectic C, F, G, H and I phases, more preferably liquid crystal compositions showing a chiral smectic C phase.

The liquid crystal composition showing a smectic C phase contains at least one compound represented by Formula (1) and can contain, as an optional component, compounds showing a smectic C phase other than the compound represented by Formula (1), for example, liquid crystal compounds such as phenylbenzoate series liquid crystal compounds, biphenylbenzoate series liquid crystal compounds, naphthalene series liquid crystal compounds, phenylnaphthalene series liquid crystal compounds, phenylpyrimidine series liquid crystal compounds, naphthylpyrimidine series liquid crystal compounds and tolan series liquid crystal compounds. Further, a compound showing no smectic C phase in itself may be contained, if desired.

The content of at least one compound represented by Formula (1) in the compositions showing smectic C phases shall not specifically be restricted and is usually 1 to 100 weight %, preferably 2 to 80 weight %, and more preferably 2 to 50 weight %.

The liquid crystal composition of the present invention showing a chiral smectic C phase comprises at least one compound represented by Formula (1) and further contains as an optically active compound, at least one of known optically active liquid crystal compounds such as optically active phenylbenzoate series liquid crystal compounds, optically active biphenylbenzoate series liquid crystal compounds, optically active naphthalene series liquid crystal compounds, optically active phenylnaphthalene series liquid crystal compounds, optically active phenylpyrimidine series liquid crystal compounds, optically active naphthylpyrimidine series liquid crystal compounds and optically active tolan series liquid crystal compounds.

The content of at least one compound represented by Formula (1) in the compositions showing chiral smectic C phases shall not specifically be restricted and is usually 1 to 99 weight %, preferably 2 to 80 weight %, and more preferably 2 to 50 weight %.

Further, in addition to the essential components described above, the liquid crystal composition of the present invention may contain, as an optional component, a compound showing no liquid crystallinity other than the naphthalene compound of the present invention (for example, dichromatic pigments such as anthraquinone pigments and azo pigments, electroconductivity-providing agents, and life improving agents).

The use of the liquid crystal composition of the present invention can provide a liquid crystal element improved in characteristics such as high speed response, temperature dependency of a response time, orientation, a memory property, and contrast ratio.

The liquid crystal element of the present invention means a liquid crystal element using a liquid crystal composition containing at least one naphthalene compound represented by Formula (1). The liquid crystal element shall not specifically be restricted and relates preferably to a smectic liquid crystal element, more preferably to a ferroelectric liquid crystal element.

The liquid crystal compositions showing ferroelectricity cause a switching phenomenon by applying voltage, and liquid crystal elements having a shorter response time can be prepared by making use of the phenomenon [for example, Japanese Patent Application Laid-Open No. 56-107216 (1981), Japanese Patent Application Laid-Open No. 59-118744 (1984), and Appl. Phys. Lett., 36 899 (1980)].

Next, the liquid crystal element of the present invention shall be explained.

The liquid crystal element of the present invention comprises the liquid crystal composition of the present invention disposed between a pair of electrode substrates to form a liquid crystal layer. In general, the liquid crystal layer can be formed by heating the liquid crystal composition under vacuum until it becomes an isotropic solution, injecting it into a liquid crystal cell, then cooling it to form a liquid crystal layer, and restoring pressure in the system to atmospheric pressure.

Shown in FIG. 1 is a schematic, cross-sectional view showing one example of the liquid crystal elements having a chiral smectic phase for explaining the structure of the liquid crystal element making use of ferroelectricity.

The liquid crystal element shown in FIG. 1 is a transmitting type liquid crystal element. As a matter of course, the form of the liquid crystal element of the present invention shall not specifically be restricted and includes not only a transmitting type liquid crystal element but also, for example, a reflecting type liquid crystal element.

In FIG. 1, 1 represents a liquid crystal (chiral smectic) layer; 2 represents a substrate; 3 represents a transparent electrode; 4 represents an insulating orientation controlling layer; 5 represents a spacer; 6 represents a lead wire; 7 represents a power source; 8 represents a polarizing plate; 9 represents a light source; $I_o$ represents incident light; and I represents transmitted light.

The liquid crystal element comprises a liquid crystal layer 1 showing a chiral smectic phase disposed between a pair of substrates 2 each of which is provided with a transparent electrode 3 and an insulating orientation controlling layer 4, wherein the layer thickness thereof is controlled by spacers 5, and a power source 7 is connected to a pair of the transparent electrodes 3 via lead wires 6 so that voltage can be applied between the transparent electrodes 3.

Further, a pair of the substrates 2 are interposed between a pair of polarizing plates 8 disposed in a cross-nicol state, and a light source 9 is disposed on one outside thereof.

In general, a glass substrate or a plastic substrate is used for the substrate 2.

The transparent electrodes 3 disposed on two sheets of the substrates 2 include, for example, transparent electrodes comprising thin films of $In_2O_3$, $SnO_2$ and ITO (indium tin oxide).

The insulating orientation controlling layers 4, which are prepared by rubbing a thin films of polymers such as polyimide with gauze or acetate cloth, are for orienting liquid crystal. The materials for the insulating orientation controlling layer 4 include, for example, inorganic materials such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide and magnesium fluoride, and organic materials such as, for example, polyvinyl alcohol, polyimide, polyamideimide, polyesterimide, polyparaxylene, polyester, polycarbonate, polyvinylacetal, polyvinyl chloride, polyvinyl acetate, polyamide, polystyrene, cellulose resins, melamine resins, urea resins, acrylic resins and photoresist resins. Further, the insulating orientation controlling layer 4 may be of a dual layer structure in which an organic insulating layer is formed on an inorganic insulating layer, or a structure comprising only the inorganic insulating layer or the organic insulating layer.

When the insulating orientation controlling layer comprises an inorganic insulating layer, it can be formed by deposition. When it comprises an organic insulating layer, it can be formed by applying a solution dissolving a precursor thereof by spinner coating, dip coating, screen printing, spray coating or roll coating and then curing a resulting film on prescribed curing conditions (for example, heating).

The layer thickness of the insulating orientation controlling layer 4 shall not specifically be restricted and is usually about 1 nm to 10 $\mu$m, preferably 1 to 300 nm, more preferably 1 to 100 nm.

Two sheets of the substrates 2 are maintained at an optional space with the spacer 5. The substrates can be maintained at an optional space by interposing, for example, silica beads or alumina beads each having a prescribed diameter as the spacer between the substrates 2 and sealing the circumference thereof with sealant (for example, epoxy adhesives). Further, polymer films and glass fibers may be used as the spacers.

Liquid crystal showing a chiral smectic phase is charged between two sheets of the substrates. The liquid crystal layer 1 is controlled usually to a thickness of 0.5 to 20 $\mu$m, preferably 1 to 5 $\mu$m.

A display system of the liquid crystal element using the liquid crystal composition of the present invention shall not specifically be restricted, and there can be used, for example, display systems of (a) helical distortion type, (b) SSFLC (surface stabilized ferroelectric liquid crystal) type, (c) TSM (transient scattering mode) type and (d) G-H (guest-host) type.

The naphthalene compound of the present invention and the liquid crystal composition containing said compound are applicable as well to fields other than liquid crystal elements for display (for example, (1) non-linear photofunctional element, (2) electronics materials such as a condenser material, (3) electronics elements such as a limiter, a memory, an amplifier and a modulator, (4) voltage sensing elements and sensors for heat, light, pressure and mechanical deformation, and (5) power generating elements such as thermoelectric generating element).

EXAMPLES

The present invention shall be explained in further detail with reference to examples, but the present invention shall not be restricted to them. The determination of the phase transition temperatures and the identification of the liquid crystal phases in the examples were carried out by observation under a polarizing microscope equipped with a temperature controller.

Symbols shown in the examples and tables mean the following:

I: isotropic liquid
N: nematic phase
SA: smectic A phase
Sc: smectic C phase
Sc*: chiral smectic C phase
C: crystal phase In Table 2, the mark "·" means the presence of the liquid crystal phase, and the mark "−" means the absence of the liquid crystal phase. Numerals in parentheses in Table 2 mean temperatures in a step of lowering temperature.

Production Example 1
Production of n-butyl 2-hydroxy-6-naphthoate

The mixture of 2-hydroxy-6-naphthoic acid of 18.8 g, N,N-dimethylformamide of 150 g and anhydrous sodium carbonate of 13.3 g was heated to 70° C., and n-butyl bromide of 16.4 g was dropwise added thereto in one hour. After finishing dropwise adding, the suspension was further stirred at 70° to 80° C. for 6 hours. The reaction mixture was cooled down to room temperature and filtrated off the inorganic salt. Then the filtrate was discharged into water of 1000 g. The deposited solid was separated, and sludging was carried out in n-hexane, whereby n-butyl 2-hydroxy-6-naphthoate of 22.0 g was obtained in the form of brown crystal.

Melting point: 107.0° to 112.0° C.

Production Example 2
Production of n-pentyl 2-hydroxy-6-naphthoate

The same procedure as described in Production Example 1 was repeated, except that n-pentyl bromide of 18.1 g was substituted for n-butyl bromide in Production Example 1, whereby n-pentyl 2-hydroxy-6-naphthoate of 23.7 g was obtained in the form of brown crystal.

Melting point: 89.0° to 93.0° C.

Production Example 3
Production of n-hexyl 2-hydroxy-6-naphthoate

The same procedure as described in Production Example 1 was repeated, except that n-hexyl bromide of 19.8 g was substituted for n-butyl bromide in Production Example 1, whereby n-hexyl 2-hydroxy-6-naphthoate of 23.9 g was obtained in the form of brown crystal.

Melting point: 93.0° to 98.0° C.

Production Example 4
Production of n-octyl 2-hydroxy-6-naphthoate

The same procedure as described in Production Example 1 was repeated, except that n-octyl bromide 23.2 g was substituted for n-butyl bromide in Production Example 1, whereby n-octyl 2-hydroxy-6-naphthoate of 27.0 g was obtained in the form of brown crystal.

Melting point: 82.0° to 86.0° C.

Production Example 5
Production of n-decyl 2-hydroxy-6-naphthoate

The same procedure as described in Production Example 1 was repeated, except that n-decyl bromide 26.5 g was substituted for n-butyl bromide in Production Example 1, whereby n-decyl 2-hydroxy-6-naphthoate of 30.2 g was obtained in the form of brown crystal.

Melting point: 92.0° to 96.0° C.

Example 1
Production of 1'-methylethyl 2-benzyloxy-6-naphthoate

Heated for refluxing were 2-benzyloxy-6-naphthoic acid of 27.8 g and oxalyl chloride of 15.2 g in toluene of 200 g for 3 hours, and then excess oxalyl chloride and toluene were distilled off under reduced pressure to obtain 2-benzyloxy-6-naphthoyl chloride. This acid chloride was dissolved in toluene of 120 g, and pyridine of 9.5 g and 2-propanol of 6.6 g were added thereto, followed by stirring the solution at 80° C. for 3 hours. Then, after filtering off deposited pyridine hydrochloride, an organic layer was washed with 1N-hydrochloric acid and further washed with water to neutral. The organic layer was separated, and toluene was distilled off under reduced pressure to obtain a crude product. The product was recrystallized from ethanol, whereby 1'-methylethyl 2-benzyloxy-6-naphthoate of 27.2 g was obtained in the form of colorless crystal.

Melting point: 89.0 to 96.0 g.

Example 2
Production of 2'-methylpropyl 2-benzyloxy-6-naphthoate

The same procedure as described in Example 1 was repeated, except that 2-methyl1-propanol of 8.1 g was substituted for 2-propanol in Example 1, whereby 2'-methylpropyl 2-benzyloxy-6-naphthoate of 30.1 g was obtained in the form of colorless crystal.

Melting point: 114.0° to 115.5° C.

Example 3
Production of 3'-methylbutyl 2-benzyloxy-6-naphthoate

The same procedure as described in Example 1 was repeated, except that 3-methyl-1-butanol of 9.7 g was substituted for 2-propanol in Example 1, whereby 3'-methylbutyl 2-benzyloxy-6-naphthoate of 31.0 g was obtained in the form of colorless crystal.

Melting point: 89.5° to 91.0° C.

Example 4
Production of 4'-methylpentyl 2-benzyloxy-6-naphthoate

The same procedure as described in Example 1 was repeated, except that 4-methyl-1-pentanol of 11.2 g was substituted for 2-propanol in Example 1, whereby 4'-methylpentyl 2-benzyloxy-6-naphthoate of 29.0 g was obtained in the form of colorless crystal.

Melting point: 64.0° to 67.0° C.

Example 5
Production of 1'-ethylpropyl 2-benzyloxy-6-naphthoate

The same procedure as described in Example 1 was repeated, except that 3-pentanol of 9.7 g was substituted for 2-propanol in Example 1, whereby 1'-ethylpropyl 2-benzyloxy-6-naphthoate of 26.1 g was obtained in the form of colorless crystal.

Melting point: 65.0° to 70.0° C.

Example 6
Production of 2'-ethylbutyl 2-benzyloxy-6-naphthoate

The same procedure as described in Example 1 was repeated, except that 2-ethyl-1-butanol of 11.2 g was substituted for 2-propanol in Example 1, whereby 2'-ethylbutyl 2-benzyloxy-6-naphthoate of 31.7 g was obtained in the form of colorless crystal.

Melting point: 84.0° to 86.0° C.

Example 7

Production of 1',1',5'-trihydroperfluoro-n-pentyl 2-benzyloxy-6-naphthoate

The same procedure as described in Example 1 was repeated, except that 1,1,5-trihydroperfluoro-n-pentyl alcohol of 25.5 g was substituted for 2-propanol in Example 1, whereby 1',1',5'-trihydroperfluoro-n-pentyl 2-benzyloxy-6-naphthoate of 38.4 g was obtained in the form of colorless crystal.

Melting point: 98.0° to 100.0° C.

Example 8

Production of 1',1',7'-trihydroperfluoro-n-heptyl 2-benzyloxy-6-naphthoate

The same procedure as described in Example 1 was repeated, except that 1,1,7-trihydroperfluoro-n-heptyl alcohol of 36.5 g was substituted for 2-propanol in Example 1, whereby 1',1',7'-trihydroperfluoro-n-heptyl 2-benzyloxy-6-naphthoate of 39.4 g was obtained in the form of colorless crystal.

Melting point: 108.0° to 112.0° C.

Example 9

Production of 2'-(perfluoro-n-butyl)ethyl 2-benzyloxy-6-naphthoate

The same procedure as described in Example 1 was repeated, except that 2-(perfluoro-n-butyl)ethanol of 51.6 g was substituted for 2-propanol in Example 1, whereby 2'-(perfluoro-n-butyl)ethyl 2-benzyloxy-6-naphthoate of 63.4 g was obtained in the form of colorless crystal.

Melting point: 108.0° to 109.0° C.

Example 10

Production of 2'-(perfluoro-n-hexyl)ethyl 2-benzyloxy-6-naphthoate

The same procedure as described in Example 1 was repeated, except that 2-(perfluoro-n-hexyl)ethanol of 40.0 g was substituted for 2-propanol in Example 1, whereby 2'-(perfluoro-n-hexyl)ethyl 2-benzyloxy-6-naphthoate of 52.4 g was obtained in the form of colorless crystal.

Melting point: 115.0° to 117.0° C.

Example 11

Production of 2'-n-butoxyethyl 2-benzyloxy-6-naphthoate

The mixture of 2-benzyloxy-6-naphthoic acid of 27.8 g, N,N-dimethylformamide of 150 g and anhydrous potassium carbonate of 13.8 g was heated to 80° C., and 2-n-butoxyethyl p-toluenesulfonate of 40.8 g was dropwise added thereto in one hour. After finishing dropwise adding, the suspension was further stirred at 70°–80° C. for 8 hours. After the reaction mixture was cooled down to room temperature, and the inorganic salt was filtered off. Then the filtrate was neutralized with hydrochloric acid and extracted with toluene. A toluene layer was washed with water, and then toluene was distilled off under reduced pressure, whereby 2-n-butoxyethyl 2-benzyloxy-6-naphthoate of 24.6 g was obtained in the form of colorless crystal.

Melting point: 57.0° to 58.0° C.

Example 12

Production of 2'-n-hexyloxyethyl 2-benzyloxy-6-naphthoate

The same procedure as described in Example 11 was repeated, except that 2-n-hexyloxyethyl p-toluenesulfonate of 45.0 g was substituted for 2-n-butoxyethyl p-toluenesulfonate in Example 11, whereby 2'-n-hexyloxyethyl 2-benzyloxy-6-naphthoate of 28.4 g was obtained in the form of colorless oily substance.

Example 13

Production of 2'-(2"-n-hexyloxyethoxy)ethyl 2-benzyloxy-6-naphthoate

The same procedure as described in Example 11 was repeated, except that 2-(2'-n-hexyloxyethoxy)ethyl p-toluenesulfonate of 51.6 g was substituted for 2-n-butoxyethyl p-toluenesulfonate in Example 11, whereby 2'-(2"-n-hexyloxyethoxy)ethyl 2-benzyloxy-6-naphthoate of 29.3 g was obtained in the form of colorless oily substance.

Example 14

Production of 2'-[2"-(2"'-n-butoxyethoxy)-ethoxy]ethyl 2-benzyloxy-6-naphthoate

The same procedure as described in Example 11 was repeated, except that 2-[2'-(2"-n-butoxyethoxy)ethoxy]ethyl p-toluenesulfonate of 54.0 g was substituted for 2-n-butoxyethyl p-toluenesulfonate in Example 11, whereby 2'-[2"-(2"'-n-butoxyethoxy)ethoxy]ethyl 2-benzyloxy-6-naphthoate of 35.6 g was obtained in the form of colorless oily substance.

Example 15

Production of 1'-methylethyl 2-hydroxy-6-naphthoate

1'-methylethyl 2-benzyloxy-6-naphthoate of 16.0 g was dissolved in 2-propanol of 100 g and hydrogenated at 40° C. in a hydrogen atmosphere at atmospheric pressure in the presence of 5 weight % Pd/C of 1 g. Pd/C was filtered off, and then 2-propanol was distilled off under reduced pressure, whereby 1'-methylethyl 2-hydroxy-6-naphthoate of 10.2 g was obtained in the form of colorless crystal.

Melting point: 110.0° to 114.0° C.

Example 16

Production of 2'-methylpropyl 2-hydroxy-6-naphthoate

The same procedure as described in Example 15 was repeated, except that 2'-methylpropyl 2-benzyloxy-6-naphthoate of 16.7 g was substituted for 1'-methylethyl 2-benzyloxy-6-naphthoate in Example 15, whereby 2'-methylpropyl 2-hydroxy-6-naphthoate of 10.7 g was obtained in the form of colorless crystal.

Melting point: 112.5° to 123.5° C.

Example 17

Production of 3'-methylbutyl 2-hydroxy-6-naphthoate

The same procedure as described in Example 15 was repeated, except that 3'-methylbutyl 2-benzyloxy-6-naphthoate of 17.4 g was substituted for 1'-methylethyl 2-benzyloxy-6-naphthoate in Example 15, whereby 3'-methylbutyl 2-hydroxy-6-naphthoate of 12.3 g was obtained in the form of colorless crystal.

Melting point: 119.5° to 121.5° C.

Example 18

Production of 4'-methylpentyl 2-hydroxy-6-naphthoate

The same procedure as described in Example 15 was repeated, except that 4'-methylpentyl 2-benzyloxy-6-naphthoate of 18.1 g was substituted for 1'-methylethyl 2-benzyloxy-6-naphthoate in Example 15, whereby 4'-methylpentyl 2-hydroxy-6-naphthoate of 11.6 g was obtained in the form of colorless crystal.

Melting point: 73.0° to 74.5° C.

Example 19
Production of 1'-ethylpropyl 2-hydroxy-6-naphthoate

The same procedure as described in Example 15 was repeated, except that 1'-ethylpropyl 2-benzyloxy-6-naphthoate of 17.4 g was substituted for 1'-methylethyl 2-benzyloxy-6-naphthoate in Example 15, whereby 1'-ethylpropyl 2-hydroxy-6-naphthoate of 11.6 g was obtained in the form of colorless crystal.

Melting point: 89.0° to 92.0° C.

Example 20
Production of 2'-ethylbutyl 2-hydroxy-6-naphthoate

The same procedure as described in Example 15 was repeated, except that 2'-ethylbutyl 2-benzyloxy-6-naphthoate of 18.1 g was substituted for 1'-methylethyl 2-benzyloxy-6-naphthoate in Example 15, whereby 2'-ethylbutyl 2-hydroxy-6-naphthoate of 12.8 g was obtained in the form of colorless crystal.

Melting point: 96.5° to 97.5° C.

Example 21
Production of 1',1',5'-trihydroperfluoro-n-pentyl 2-hydroxy-6-naphthoate The same procedure as described in Example 15 was repeated, except that 1',1',5'-trihydroperfluoro-n-pentyl 2-benzyloxy-6-naphthoate of 24.6 g was substituted for 1'-methylethyl 2-benzyloxy-6-naphthoate in Example 15, whereby 1',1',5'-trihydroperfluoro-n-pentyl 2-hydroxy-6-naphthoate of 17.5 g was obtained in the form of colorless crystal.

Melting point: 105.0° to 113.0° C.

Example 22
Production of 1',1',7'-trihydroperfluoro-n-heptyl 2-hydroxy-6-naphthoate The same procedure as described in Example 15 was repeated, except that 1',1',7'-trihydroperfluoro-n-heptyl 2-benzyloxy-6-naphthoate of 29.6 g was substituted for 1'-methylethyl 2-benzyloxy-6-naphthoate in Example 15, whereby 1',1',7'-trihydroperfluoro-n-heptyl 2-hydroxy-6-naphthoate of 20.1 g was obtained in the form of colorless crystal.

Melting point: 123.0° to 132.0° C.

Example 23
Production of 2'-(perfluoro-n-butyl)ethyl 2-hydroxy-6-naphthoate

The same procedure as described in Example 15 was repeated, except that 2'-(perfluoro-n-butyl)ethyl 2-benzyloxy-6-naphthoate of 26.2 g was substituted for 1'-methylethyl 2-benzyloxy-6-naphthoate in Example 15, whereby 2'-(perfluoro-n-butyl)ethyl 2-hydroxy-6-naphthoate of 18.6 g was obtained in the form of colorless crystal.

Melting point: 101.0° to 103.0° C.

Example 24
Production of 2'-(perfluoro-n-hexyl)ethyl 2-hydroxy-6-naphthoate

The same procedure as described in Example 15 was repeated, except that 2'-(perfluoro-n-hexyl)ethyl 2-benzyloxy-6-naphthoate of 31.2 g was substituted for 1'-methylethyl 2-benzyloxy-6-naphthoate in Example 15, whereby 2'-(perfluoro-n-hexyl)ethyl 2-hydroxy-6-naphthoate of 21.4 g was obtained in the form of colorless crystal.

Melting point: 124.0° to 127.0° C.

Example 25
Production of 2'-n-butoxyethyl 2-hydroxy-6-naphthoate

The same procedure as described in Example 15 was repeated, except that 2'-n-butoxyethyl 2-benzyloxy-6-naphthoate of 18.9 g was substituted for 1'-methylethyl 2-benzyloxy-6-naphthoate in Example 15, whereby 2'-n-butoxyethyl 2-hydroxy-6-naphthoate of 13.7 g was obtained in the form of colorless crystal.

Melting point: 54.0° to 56.0° C.

Example 26
Production of 2'-n-hexyloxyethyl 2-hydroxy-6-naphthoate

The same procedure as described in Example 15 was repeated, except that 2'-n-hexyloxyethyl 2-benzyloxy-6-naphthoate of 20.3 g was substituted for 1'-methylethyl 2-benzyloxy-6-naphthoate in Example 15, whereby 2'-nhexyloxyethyl 2-hydroxy-6-naphthoate of 15.0 g was obtained in the form of colorless crystal.

Melting point: 67.0° to 68.0° C.

Example 27
Production of 2'-(2"-n-hexyloxyethoxy)ethyl 2-hydroxy-6-naphthoate The same procedure as described in Example 15 was repeated, except that 2'-(2"-n-hexyloxyethoxy)ethyl 2-benzyloxy-6-naphthoate of 22.5 g was substituted for 1'-methylethyl 2-benzyloxy-6-naphthoate in Example 15, whereby 2'-(2"-n-hexyloxyethoxy)ethyl 2-hydroxy-6-naphthoate of 15.3 g was obtained in the form of colorless crystal.

Melting point: 59.0° to 62.0° C.

Example 28
Production of 2'-[2"-(2"'-n-butoxyethoxy)ethoxy]ethyl 2-hydroxy-6-naphthoate The same procedure as described in Example 15 was repeated, except that 2'-[2"-(2"'-n-butoxyethoxy)ethoxy]ethyl 2-benzyloxy-6-naphthoate of 23.3 g was substituted for 1'-methylethyl 2-benzyloxy-6-naphthoate in Example 15, whereby 2'-[2"-(2"'-n-butoxyethoxy)ethoxy]ethyl 2-hydroxy-6-naphthoate of 14.2 g was obtained in the form of colorless oily substance.

Example 29
Production of Exemplified Compound 15

Dissolved in chloroform of 5 g were 1'-methylethyl 2-hydroxy-6-naphthoate of 230 mg, 4-n-decyloxybenzoic acid of 278 mg, N,N'-dicyclohexylcarbodiimide of 247 mg and 4-pyrrolidinopyridine of 7 mg, and the solution was stirred at room temperature for 24 hours. By-produced N,N'-dicyclohexylurea was filtered off, and then chloroform was distilled off under reduced pressure to obtain a crude product. The crude product was refined with silica gel column chromatography (eluent: toluene) and further recrystallized twice from ethanol/ethyl acetate, whereby the intended product of 392 mg was obtained in the form of colorless crystal.

The phase transition temperatures of this compound are shown in Table 2.

Examples 30 to 114

The naphthalene compounds were produced in the same manner as described in Example 29, except that 2-hydroxy-6-naphthoic acid esters represented by Formula (3a) and various carboxylic acids represented by Formula (4), each shown in Table 1, were used.

The phase transition temperatures of these compounds are shown in Table 2.

TABLE 1

| Example No. | Compound (4)<br>R₁-(O)_z-A-COOH | Compound (3a)<br>[6-hydroxy-2-naphthoate ester: HO-naphthalene-COOR₂] |
|---|---|---|
| 29 | n-C$_{10}$H$_{21}$O—C$_6$H$_4$—COOH | HO—naphthalene—COOCH(CH$_3$)$_2$ |
| 30 | n-C$_{12}$H$_{25}$O—C$_6$H$_4$—COOH | HO—naphthalene—COOCH(CH$_3$)$_2$ |
| 31 | n-C$_{10}$H$_{21}$O—C$_6$H$_4$—COOH | HO—naphthalene—COOC$_4$H$_9$-n |
| 32 | n-C$_8$H$_{17}$O—C$_6$H$_4$—COOH | HO—naphthalene—COOCH$_2$CH(CH$_3$)$_2$ |
| 33 | n-C$_9$H$_{19}$O—C$_6$H$_4$—COOH | HO—naphthalene—COOCH$_2$CH(CH$_3$)$_2$ |
| 34 | n-C$_{10}$H$_{21}$O—C$_6$H$_4$—COOH | HO—naphthalene—COOCH$_2$CH(CH$_3$)$_2$ |
| 35 | n-C$_{11}$H$_{23}$O—C$_6$H$_4$—COOH | HO—naphthalene—COOCH$_2$CH(CH$_3$)$_2$ |
| 36 | n-C$_{12}$H$_{25}$O—C$_6$H$_4$—COOH | HO—naphthalene—COOCH$_2$CH(CH$_3$)$_2$ |
| 37 | n-C$_6$H$_{13}$—C$_6$H$_4$—COOH | HO—naphthalene—COOCH$_2$CH(CH$_3$)$_2$ |

TABLE 1-continued

| Example No. | Compound (4)<br>$R_1\text{-}(O)_z\text{-}A\text{-}COOH$ | Compound (3a)<br>(6-hydroxy-2-naphthyl ester with $COOR_2$) |
|---|---|---|
| 38 | 3-F, 4-n-$C_{10}H_{21}O$-benzoic acid | $COOCH_2CH(CH_3)_2$ |
| 39 | 4-n-$C_6H_{13}$-benzoic acid | $COOC_5H_{11}$-n |
| 40 | 4-n-$C_8H_{17}O$-benzoic acid | $COO(CH_2)_2CH(CH_3)_2$ |
| 41 | 4-n-$C_9H_{19}O$-benzoic acid | $COO(CH_2)_2CH(CH_3)_2$ |
| 42 | 4-n-$C_{10}H_{21}O$-benzoic acid | $COO(CH_2)_2CH(CH_3)_2$ |
| 43 | 4-n-$C_{11}H_{23}O$-benzoic acid | $COO(CH_2)_2CH(CH_3)_2$ |
| 44 | 4-n-$C_{12}H_{25}O$-benzoic acid | $COO(CH_2)_2CH(CH_3)_2$ |
| 45 | 3-F, 4-n-$C_{10}H_{21}O$-benzoic acid | $COO(CH_2)_2CH(CH_3)_2$ |
| 46 | 4-n-$C_6H_{13}$-benzoic acid | $COO(CH_2)_2CH(CH_3)_2$ |

TABLE 1-continued

| Example No. | Compound (4)<br>$R_1\text{-}(O)_z\text{-}A\text{-}COOH$ | Compound (3a)<br>(6-hydroxy-2-naphthoate ester: $HO$—[naphthalene]—$COOR_2$) |
|---|---|---|
| 47 | n-$C_{10}H_{21}O$—⟨C₆H₄⟩—COOH | HO—[naphthalene]—$COOCH(C_2H_5)_2$ |
| 48 | n-$C_{12}H_{25}O$—⟨C₆H₄⟩—COOH | HO—[naphthalene]—$COOCH(C_2H_5)_2$ |
| 49 | n-$C_8H_{17}O$—⟨C₆H₄⟩—COOH | HO—[naphthalene]—$COOC_6H_{13}$-n |
| 50 | n-$C_{10}H_{21}O$—⟨C₆H₄⟩—COOH | HO—[naphthalene]—$COOC_6H_{13}$-n |
| 51 | n-$C_{12}H_{25}O$—⟨C₆H₄⟩—COOH | HO—[naphthalene]—$COOC_6H_{13}$-n |
| 52 | n-$C_{11}H_{23}O$—⟨C₆H₃(F)⟩—COOH | HO—[naphthalene]—$COOC_6H_{13}$-n |
| 53 | n-$C_{10}H_{21}O$—⟨C₆H₄⟩—COOH | HO—[naphthalene]—$COO(CH_2)_3CH(CH_3)_2$ |
| 54 | n-$C_{12}H_{25}O$—⟨C₆H₄⟩—COOH | HO—[naphthalene]—$COO(CH_2)_3CH(CH_3)_2$ |
| 55 | n-$C_6H_{13}$—⟨C₆H₄⟩—COOH | HO—[naphthalene]—$COO(CH_2)_3CH(CH_3)_2$ |

TABLE 1-continued

| Example No. | Compound (4) R₁-(O)ᵤ-A-COOH | Compound (3a) [6-hydroxy-2-naphthoate with HO at 6-position and COOR₂ at 2-position] |
|---|---|---|
| 56 | n-C₁₀H₂₁O—[C₆H₃(F)]—COOH (F ortho to OR₁) | HO—[naphthalene]—COO(CH₂)₃CH(CH₃)₂ |
| 57 | n-C₁₀H₂₁O—[C₆H₄]—COOH | HO—[naphthalene]—COOCH₂CH(C₂H₅)₂ |
| 58 | n-C₁₂H₂₅O—[C₆H₄]—COOH | HO—[naphthalene]—COOCH₂CH(C₂H₅)₂ |
| 59 | n-C₁₀H₂₁O—[C₆H₃(F)]—COOH (F ortho to OR₁) | HO—[naphthalene]—COOCH₂CH(C₂H₅)₂ |
| 60 | n-C₈H₁₇O—[C₆H₄]—COOH | HO—[naphthalene]—COOC₈H₁₇-n |
| 61 | n-C₈H₁₇O—[C₆H₄]—COOH | HO—[naphthalene]—COOC₁₀H₂₁-n |
| 62 | n-C₁₀H₂₁O—[C₆H₄]—COOH | HO—[naphthalene]—COOC₁₀H₂₁-n |
| 63 | H(CF₂)₄CH₂O—[C₆H₄]—COOH | HO—[naphthalene]—COOCH₂CH(CH₃)₂ |
| 64 | H(CF₂)₆CH₂O—[C₆H₄]—COOH | HO—[naphthalene]—COOCH₂CH(CH₃)₂ |

TABLE 1-continued

| Example No. | Compound (4)<br>$R_1-(O)_z-A-COOH$ | Compound (3a)<br>(6-hydroxy-2-naphthoate $COOR_2$) |
|---|---|---|
| 65 | $H(CF_2)_8CH_2O-C_6H_4-COOH$ | $COOCH_2CH(CH_3)_2$ |
| 66 | $F(CF_2)_8(CH_2)_3O-C_6H_4-COOH$ | $COOCH_2CH(CH_3)_2$ |
| 67 | $H(CF_2)_4CH_2O-C_6H_4-COOH$ | $COO(CH_2)_2CH(CH_3)_2$ |
| 68 | $H(CF_2)_6CH_2O-C_6H_4-COOH$ | $COO(CH_2)_2CH(CH_3)_2$ |
| 69 | $H(CF_2)_8CH_2O-C_6H_4-COOH$ | $COO(CH_2)_2CH(CH_3)_2$ |
| 70 | $F(CF_2)_8(CH_2)_3O-C_6H_4-COOH$ | $COO(CH_2)_2CH(CH_3)_2$ |
| 71 | $n-C_8H_{17}O-C_6H_4-COOH$ | $COOCH_2(CF_2)_4H$ |
| 72 | $n-C_{10}H_{21}O-C_6H_4-COOH$ | $COOCH_2(CF_2)_4H$ |
| 73 | $n-C_{12}H_{25}O-C_6H_4-COOH$ | $COOCH_2(CF_2)_4H$ |

TABLE 1-continued

| Example No. | Compound (4)<br>R$_1$-(O)$_z$-A-COOH | Compound (3a)<br>(6-hydroxynaphthalene-2-COOR$_2$) R$_2$ |
|---|---|---|
| 74 | n-C$_8$H$_{17}$O—C$_6$H$_4$—COOH | CH$_2$(CF$_2$)$_6$H |
| 75 | n-C$_{10}$H$_{21}$O—C$_6$H$_4$—COOH | CH$_2$(CF$_2$)$_6$H |
| 76 | n-C$_{12}$H$_{25}$O—C$_6$H$_4$—COOH | CH$_2$(CF$_2$)$_6$H |
| 77 | n-C$_8$H$_{17}$O—C$_6$H$_4$—COOH | (CH$_2$)$_2$(CF$_2$)$_4$F |
| 78 | n-C$_9$H$_{19}$O—C$_6$H$_4$—COOH | (CH$_2$)$_2$(CF$_2$)$_4$F |
| 79 | n-C$_{10}$H$_{21}$O—C$_6$H$_4$—COOH | (CH$_2$)$_2$(CF$_2$)$_4$F |
| 80 | n-C$_{11}$H$_{23}$O—C$_6$H$_4$—COOH | (CH$_2$)$_2$(CF$_2$)$_4$F |
| 81 | n-C$_{12}$H$_{25}$O—C$_6$H$_4$—COOH | (CH$_2$)$_2$(CF$_2$)$_4$F |
| 82 | n-C$_8$H$_{17}$O—C$_6$H$_4$—COOH | (CH$_2$)$_2$(CF$_2$)$_6$F |

TABLE 1-continued

| Example No. | Compound (4)<br>$R_1\text{-}(O)_z\text{-}A\text{-}COOH$ | Compound (3a)<br>naphthalene with HO- and -COOR$_2$ |
|---|---|---|
| 83 | n-C$_{10}$H$_{21}$O—⟨⟩—COOH | HO—[naphthalene]—COO(CH$_2$)$_2$(CF$_2$)$_6$F |
| 84 | n-C$_{12}$H$_{25}$O—⟨⟩—COOH | HO—[naphthalene]—COO(CH$_2$)$_2$(CF$_2$)$_6$F |
| 85 | H(CF$_2$)$_8$CH$_2$O—⟨⟩—COOH | HO—[naphthalene]—COOCH$_2$(CF$_2$)$_4$F |
| 86 | H(CF$_2$)$_8$CH$_2$O—⟨⟩—COOH | HO—[naphthalene]—COO(CH$_2$)$_2$(CF$_2$)$_6$F |
| 87 | n-C$_6$H$_{13}$OCH$_2$CH$_2$O—⟨⟩—COOH | HO—[naphthalene]—COOC$_8$H$_{17}$-n |
| 88 | n-C$_6$H$_{13}$OCH$_2$CH$_2$O—⟨⟩—COOH | HO—[naphthalene]—COOC$_{10}$H$_{21}$-n |
| 89 | n-C$_6$H$_{13}$(OCH$_2$CH$_2$)$_2$O—⟨⟩—COOH | HO—[naphthalene]—COOC$_{10}$H$_{21}$-n |
| 90 | n-C$_6$H$_{13}$OCH$_2$CH$_2$O—⟨⟩—COOH | HO—[naphthalene]—COOCH$_2$(CF$_2$)$_6$H |
| 91 | n-C$_6$H$_{13}$OCH$_2$CH$_2$O—⟨⟩—COOH | HO—[naphthalene]—COO(CH$_2$)$_2$(CF$_2$)$_4$F |

TABLE 1-continued

| Example No. | Compound (4) $R_1-(O)_z-A-COOH$ | Compound (3a) |
|---|---|---|
| 92 | n-C$_6$H$_13$(OCH$_2$CH$_2$)$_2$O—⌬—COOH | HO—⌬⌬—COO(CH$_2$)$_2$(CF$_2$)$_4$F |
| 93 | n-C$_{10}$H$_{21}$O—⌬—COOH | HO—⌬⌬—COOCH$_2$CH$_2$OC$_4$H$_9$-n |
| 94 | n-C$_{12}$H$_{25}$O—⌬—COOH | HO—⌬⌬—COOCH$_2$CH$_2$OC$_4$H$_9$-n |
| 95 | n-C$_{10}$H$_{21}$O—⌬—COOH | HO—⌬⌬—COOCH$_2$CH$_2$OC$_6$H$_{13}$-n |
| 96 | n-C$_{12}$H$_{25}$O—⌬—COOH | HO—⌬⌬—COOCH$_2$CH$_2$OC$_6$H$_{13}$-n |
| 97 | n-C$_{10}$H$_{21}$O—⌬—COOH | HO—⌬⌬—COO(CH$_2$CH$_2$O)$_2$C$_6$H$_{13}$-n |
| 98 | n-C$_{12}$H$_{25}$O—⌬—COOH | HO—⌬⌬—COO(CH$_2$CH$_2$O)$_2$C$_6$H$_{13}$-n |
| 99 | n-C$_{10}$H$_{21}$O—⌬—⌬—COOH | HO—⌬⌬—COOCH$_2$CH(CH$_3$)$_2$ |
| 100 | n-C$_{10}$H$_{21}$—⌬(F)—⌬—COOH | HO—⌬⌬—COOCH$_2$CH(CH$_3$)$_2$ |

Compound (3a) general structure: HO—⌬⌬—COOR$_2$ (naphthalene)

TABLE 1-continued

| Example No. | Compound (4)<br>$R_1\text{-}(O)_z\text{-}A\text{-}COOH$ | Compound (3a) |
|---|---|---|
| 101 | n-C$_{10}$H$_{21}$O—⟨biphenyl⟩—COOH | HO—⟨naphthyl⟩—COO(CH$_2$)$_2$CH(CH$_3$)$_2$ |
| 102 | n-C$_8$H$_{17}$—⟨biphenyl⟩—COOH | HO—⟨naphthyl⟩—COO(CH$_2$)$_2$CH(CH$_3$)$_2$ |
| 103 | n-C$_{10}$H$_{21}$O—⟨biphenyl⟩—COOH | HO—⟨naphthyl⟩—COO(CH$_2$)$_3$CH(CH$_3$)$_2$ |
| 104 | n-C$_{10}$H$_{21}$O—⟨biphenyl⟩—COOH | HO—⟨naphthyl⟩—COOCH$_2$CH(C$_2$H$_5$)$_2$ |
| 105 | n-C$_{10}$H$_{21}$O—⟨biphenyl⟩—COOH | HO—⟨naphthyl⟩—COOC$_8$H$_{17}$-n |
| 106 | n-C$_6$H$_{13}$OCH$_2$CH$_2$O—⟨biphenyl⟩—COOH | HO—⟨naphthyl⟩—COO(CH$_2$)$_2$CH(CH$_3$)$_2$ |
| 107 | n-C$_6$H$_{13}$(OCH$_2$CH$_2$)$_2$O—⟨biphenyl⟩—COOH | HO—⟨naphthyl⟩—COO(CH$_2$)$_2$CH(CH$_3$)$_2$ |
| 108 | n-C$_6$H$_{13}$OCH$_2$CH$_2$O—⟨biphenyl⟩—COOH | HO—⟨naphthyl⟩—COOCH$_2$CH(C$_2$H$_5$)$_2$ |
| 109 | n-C$_6$H$_{13}$(OCH$_2$CH$_2$)$_2$O—⟨biphenyl⟩—COOH | HO—⟨naphthyl⟩—COOCH$_2$CH(C$_2$H$_5$)$_2$ |

TABLE 1-continued

| Example No. | Compound (4) R₁-(O)ᵤ-A-COOH | Compound (3a) |
|---|---|---|
| 110 | n-C₁₀H₂₁O—⟨phenyl⟩—⟨phenyl⟩—COOH | HO—⟨naphthyl⟩—COOR₂ |
| | | HO—⟨naphthyl⟩—COO(CH₂CH₂O)₃C₄H₉-n |
| 111 | n-C₁₂H₂₅O—⟨phenyl⟩—⟨phenyl⟩—COOH | HO—⟨naphthyl⟩—COO(CH₂CH₂O)₃C₄H₉-n |
| 112 | n-C₁₂H₂₅O—⟨naphthyl⟩—COOH | HO—⟨naphthyl⟩—COO(CH₂)₂CH(CH₃)₂ |
| 113 | n-C₁₀H₂₁O—⟨pyridyl-N⟩—COOH | HO—⟨naphthyl⟩—COOCH₂CH(CH₃)₂ |
| 114 | n-C₅H₁₁—⟨cyclohexyl-H⟩—COOH | HO—⟨naphthyl⟩—COO(CH₂)₂CH(CH₃)₂ |

TABLE 2

| Example No. | Exemplified compound No. | Structure | Phase transition temperature (°C.) | | | | | |
|---|---|---|---|---|---|---|---|---|
| | | | C | $S_C$ | $S_A$ | N | I |
| 29 | 15 | n-C$_{10}$H$_{21}$O—⌬—COO—⌬⌬—COOCH(CH$_3$)$_2$ | · 65 | · (60) | · 98 | — | · |
| 30 | 16 | n-C$_{12}$H$_{25}$O—⌬—COO—⌬⌬—COOCH(CH$_3$)$_2$ | · 73 | · (62) | · 97 | — | · |
| 31 | 19 | n-C$_{10}$H$_{21}$O—⌬—COO—⌬⌬—COOC$_4$H$_9$-n | · 57 | · (43) | · 113 | — | · |
| 32 | 27 | n-C$_8$H$_{17}$O—⌬—COO—⌬⌬—COOCH$_2$CH(CH$_3$)$_2$ | · 61 | · (48) | · 113 | · 118 | · |
| 33 | 28 | n-C$_9$H$_{19}$O—⌬—COO—⌬⌬—COOCH$_2$CH(CH$_3$)$_2$ | · 66 | · (62) | · 114 | · 116 | · |
| 34 | 29 | n-C$_{10}$H$_{21}$O—⌬—COO—⌬⌬—COOCH$_2$CH(CH$_3$)$_2$ | · 67 | · (64) | · 116 | — | · |

TABLE 2-continued

| Example No. | Exemplified compound No. | Phase transition temperature (°C.) | | | | |
|---|---|---|---|---|---|---|
| | | C | S_C | S_A | N | I |
| 35 | 30 n-C₁₁H₂₃O–⟨Ph⟩–COO–⟨Naph⟩–COOCH₂CH(CH₃)₂ | · 79 | · (68) | · 115 | — | · |
| 36 | 31 n-C₁₂H₂₅O–⟨Ph⟩–COO–⟨Naph⟩–COOCH₂CH(CH₃)₂ | · 57 | · (51) | · 115 | — | · |
| 37 | 33 n-C₆H₁₃–⟨Ph⟩–COO–⟨Naph⟩–COOCH₂CH(CH₃)₂ | · 64 | · (54) | · 77 | — | · |
| 38 | 35 n-C₁₀H₂₁O–⟨Ph(F)⟩–COO–⟨Naph⟩–COOCH₂CH(CH₃)₂ | · 83 | · (71) | · 106 | — | · |
| 39 | 41 n-C₆H₁₃–⟨Ph⟩–COO–⟨Naph⟩–COOC₅H₁₁-n | · 64 | — | · (57) | · 65 | · |
| 40 | 44 n-C₈H₁₇O–⟨Ph⟩–COO–⟨Naph⟩–COO(CH₂)₂CH(CH₃)₂ | · 76 | — | · 107 | — | · |

TABLE 2-continued

| Example No. | Exemplified compound No. | | Phase transition temperature (°C.) | | | | |
|---|---|---|---|---|---|---|---|
| | | C | S$_C$ | S$_A$ | N | I |
| 41 | 45 | structure with COO(CH$_2$)$_2$CH(CH$_3$)$_2$ and n-C$_9$H$_{19}$O | · 68 | · (52) | · 103 | — | · |
| 42 | 46 | structure with COO(CH$_2$)$_2$CH(CH$_3$)$_2$ and n-C$_{10}$H$_{21}$O | · 79 | · (66) | · 105 | — | · |
| 43 | 47 | structure with COO(CH$_2$)$_2$CH(CH$_3$)$_2$ and n-C$_{11}$H$_{23}$O | · 77 | · (74) | · 104 | — | · |
| 44 | 48 | structure with COO(CH$_2$)$_2$CH(CH$_3$)$_2$ and n-C$_{12}$H$_{25}$O | · 75 | · (74) | · 104 | — | · |
| 45 | 49 | structure with COO(CH$_2$)$_2$CH(CH$_3$)$_2$, F, and n-C$_{10}$H$_{21}$O | · 83 | · (58) | · 96 | — | · |
| 46 | 50 | structure with COO(CH$_2$)$_2$CH(CH$_3$)$_2$ and n-C$_6$H$_{13}$ | · 65 | · (38) | · (52) | — | · |

TABLE 2-continued

| Example No. | Exemplified compound No. | Phase transition temperature (°C.) | | | | | | | | |
|---|---|---|---|---|---|---|---|---|---|---|
| | | C | | $S_C$ | | $S_A$ | | N | | I |
| 47 | 51 n-C$_{10}$H$_{21}$O–⬡–COO–⬡⬡–COOCH(C$_2$H$_5$)$_2$ | · | 60 | · | (41) | · | (58) | — | | · |
| 48 | 52 n-C$_{12}$H$_{25}$O–⬡–COO–⬡⬡–COOCH(C$_2$H$_5$)$_2$ | · | 64 | · | (38) | · | (58) | — | | · |
| 49 | 55 n-C$_8$H$_{17}$O–⬡–COO–⬡⬡–COOC$_6$H$_{13}$-n | · | 73 | · | 74 | · | 109 | — | | · |
| 50 | 56 n-C$_{10}$H$_{21}$O–⬡–COO–⬡⬡–COOC$_6$H$_{13}$-n | · | 76 | · | 77 | · | 110 | — | | · |
| 51 | 57 n-C$_{12}$H$_{25}$O–⬡–COO–⬡⬡–COOC$_6$H$_{13}$-n | · | 67 | · | (64) | · | 110 | — | | · |
| 52 | 60 n-C$_{11}$H$_{23}$O–⬡(F)–COO–⬡⬡–COOC$_6$H$_{13}$-n | · | 87 | · | (66) | · | 99 | — | | · |

TABLE 2-continued
| Example No. | Exemplified compound No. | | Phase transition temperature (°C.) | | | | | | | | |
|---|---|---|---|---|---|---|---|---|---|---|---|
| | | | C | | $S_C$ | | $S_A$ | | N | | I |
| 53 | 62 |  | · | 64 | · | 67 | · | 105 | — | | · |
| 54 | 63 |  | · | 71 | · | 79 | · | 104 | — | | · |
| 55 | 65 |  | · | 69 | | | (53) | | · | | · |
| 56 | 66 |  | · | 75 | · | (72) | · | 94 | — | | · |
| 57 | 67 |  | · | 68 | · | (55) | · | 78 | — | | · |
| 58 | 68 |  | · | 83 | · | (56) | | (78) | — | (55) | · |

TABLE 2-continued

| Example No. | Exemplified compound No. | | Phase transition temperature (°C.) | | | | |
|---|---|---|---|---|---|---|---|
| | | C | S_C | S_A | N | I |
| 59 | 72 | n-C₁₀H₂₁O–⟨F⟩–COO–⟨naphthalene⟩–COOCH₂CH(C₂H₅)₂ | · 56 | · (48) | · 67 | — | · |
| 60 | 86 | n-C₈H₁₇O–⟨⟩–COO–⟨naphthalene⟩–COOC₈H₁₇-n | · 75 | · (58) | · 108 | — | · |
| 61 | 106 | n-C₈H₁₇O–⟨⟩–COO–⟨naphthalene⟩–COOC₁₀H₂₁-n | · 79 | · (72) | · 105 | — | · |
| 62 | 107 | n-C₁₀H₂₁O–⟨⟩–COO–⟨naphthalene⟩–COOC₁₀H₂₁-n | · 86 | · (77) | · 107 | — | · |
| 63 | 148 | H(CF₂)₄CH₂O–⟨⟩–COO–⟨naphthalene⟩–COOCH₂CH(CH₃)₂ | · 103 | — | · 127 | — | · |
| 64 | 149 | H(CF₂)₆CH₂O–⟨⟩–COO–⟨naphthalene⟩–COOCH₂CH(CH₃)₂ | · 96 | · (88) | · 148 | — | · |

TABLE 2-continued

| Example No. | Exemplified compound No. | Phase transition temperature (°C.) C | $S_C$ | $S_A$ | N | I |
|---|---|---|---|---|---|---|
| 65 | 150 — H(CF₂)₆CH₂O—⌬—COO—⌬⌬—COOCH₂CH(CH₃)₂ | · 103 | — | · 170 | — | · |
| 66 | 152 — F(CF₂)₈(CH₂)₃O—⌬—COO—⌬⌬—COOCH₂CH(CH₃)₂ | · 112 | · (111) | · 228 | — | · |
| 67 | 161 — H(CF₂)₄CH₂O—⌬—COO—⌬⌬—COO(CH₂)₂CH(CH₃)₂ | · 80 | · (76) | · 99 | — | · |
| 68 | 162 — H(CF₂)₆CH₂O—⌬—COO—⌬⌬—COO(CH₂)₂CH(CH₃)₂ | · 81 | · (78) | · 115 | — | · |
| 69 | 163 — H(CF₂)₈CH₂O—⌬—COO—⌬⌬—COO(CH₂)₂CH(CH₃)₂ | · 102 | · (77) | · 138 | — | · |
| 70 | 164 — F(CF₂)₈(CH₂)₃O—⌬—COO—⌬⌬—COO(CH₂)₂CH(CH₃)₂ | · 120 | · 140 | · 206 | — | · |

TABLE 2-continued

| Example No. | Exemplified compound No. | Structure | C | $S_C$ | $S_A$ | N | I |
|---|---|---|---|---|---|---|---|
| 71 | 185 | n-C$_8$H$_{17}$O—C$_6$H$_4$—COO—Naphthalene—COOCH$_2$(CF$_2$)$_4$H | · 91 · | (88) | · 108 | — | · |
| 72 | 187 | n-C$_{10}$H$_{21}$O—C$_6$H$_4$—COO—Naphthalene—COOCH$_2$(CF$_2$)$_4$H | · 79 · | 88 · | 110 | — | · |
| 73 | 188 | n-C$_{12}$H$_{25}$O—C$_6$H$_4$—COO—Naphthalene—COOCH$_2$(CF$_2$)$_4$H | · 72 · | 87 · | 104 | — | · |
| 74 | 189 | n-C$_8$H$_{17}$O—C$_6$H$_4$—COO—Naphthalene—COOCH$_2$(CF$_2$)$_6$H | · 93 · | 103 · | 133 | — | · |
| 75 | 190 | n-C$_{10}$H$_{21}$O—C$_6$H$_4$—COO—Naphthalene—COOCH$_2$(CF$_2$)$_6$H | · 82 · | 110 · | 124 | — | · |
| 76 | 191 | n-C$_{12}$H$_{25}$O—C$_6$H$_4$—COO—Naphthalene—COOCH$_2$(CF$_2$)$_6$H | · 93 · | 110 · | 116 | — | · |

TABLE 2-continued

| Example No. | Exemplified compound No. | Phase transition temperature (°C.) | | | | | |
|---|---|---|---|---|---|---|---|
| | | C | | $S_C$ | | $S_A$ | N | I |

| Example No. | Compound No. | Structure | C | $S_C$ | $S_A$ | N | I |
|---|---|---|---|---|---|---|---|
| 77 | 193 | n-C$_8$H$_{17}$O—⌬—COO—⌬⌬—COO(CH$_2$)$_2$(CF$_2$)$_4$F | · 84 · | 136 · | 157 · | — | · |
| 78 | 194 | n-C$_9$H$_{19}$O—⌬—COO—⌬⌬—COO(CH$_2$)$_2$(CF$_2$)$_4$F | · 89 · | 138 · | 150 · | — | · |
| 79 | 195 | n-C$_{10}$H$_{21}$O—⌬—COO—⌬⌬—COO(CH$_2$)$_2$(CF$_2$)$_4$F | · 83 · | 137 · | 146 · | — | · |
| 80 | 196 | n-C$_{11}$H$_{23}$O—⌬—COO—⌬⌬—COO(CH$_2$)$_2$(CF$_2$)$_4$F | · 89 · | 134 · | 141 · | — | · |
| 81 | 197 | n-C$_{12}$H$_{25}$O—⌬—COO—⌬⌬—COO(CH$_2$)$_2$(CF$_2$)$_4$F | · 87 · | 130 · | 136 · | — | · |
| 82 | 202 | n-C$_8$H$_{17}$O—⌬—COO—⌬⌬—COO(CH$_2$)$_2$(CF$_2$)$_6$F | · 102 · | 150 · | 176 · | — | · |

TABLE 2-continued

| Example No. | Exemplified compound No. | Structure | C | $S_C$ | $S_A$ | N | I |
|---|---|---|---|---|---|---|---|
| 83 | 203 | n-C₁₀H₂₁O—⟨⟩—COO—⟨⟩⟨⟩—COO(CH₂)₂(CF₂)₆F | · 96 | · 151 | · 164 | — | · |
| 84 | 204 | n-C₁₂H₂₅O—⟨⟩—COO—⟨⟩⟨⟩—COO(CH₂)₂(CF₂)₆F | · 101 | · 146 | · 152 | — | · |
| 85 | 207 | H(CF₂)₈CH₂O—⟨⟩—COO—⟨⟩⟨⟩—COOCH₂(CF₂)₄H | · 116 | · (92) | · 123 | — | · |
| 86 | 216 | H(CF₂)₈CH₂O—⟨⟩—COO—⟨⟩⟨⟩—COO(CH₂)₂(CF₂)₄H | · 116 | · 132 | · 134 | — | · |
| 87 | 220 | n-C₆H₁₃OCH₂CH₂O—⟨⟩—COO—⟨⟩⟨⟩—COOC₈H₁₇-n | · 52 | · (35) | · 57 | — | · |
| 88 | 221 | n-C₆H₁₃OCH₂CH₂O—⟨⟩—COO—⟨⟩⟨⟩—COOC₁₀H₂₁-n | · 66 | — | · (59) | — | · |

TABLE 2-continued

| Example No. | Exemplified compound No. | Structure | C | S_C | S_A | N | I |
|---|---|---|---|---|---|---|---|
| 89 | 224 | n-C$_6$H$_{13}$(OCH$_2$CH$_2$)$_2$O—⦿⦿—COO—⬡—COOC$_{10}$H$_{21}$-n | • 48 | — | • (36) | — | • |
| 90 | 232 | n-C$_6$H$_{13}$OCH$_2$CH$_2$O—⦿⦿—COO—⬡—COOCH$_2$(CF$_2$)$_6$H | • 83 | • (72) | • 95 | — | • |
| 91 | 233 | n-C$_6$H$_{13}$OCH$_2$CH$_2$O—⦿⦿—COO—⬡—COO(CH$_2$)$_2$(CF$_2$)$_4$H | • 74 | • 89 | • 126 | — | • |
| 92 | 236 | n-C$_6$H$_{13}$(OCH$_2$CH$_2$)$_2$O—⦿⦿—COO—⬡—COO(CH$_2$)$_2$(CF$_2$)$_4$F | • 57 | • 87 | • 115 | — | • |
| 93 | 244 | n-C$_{10}$H$_{21}$O—⬡—COO—⦿⦿—COO—⬡—COOCH$_2$CH$_2$OC$_4$H$_9$-n | • 71 | • (50) | • 88 | — | • |
| 94 | 245 | n-C$_{12}$H$_{25}$O—⬡—COO—⦿⦿—COO—⬡—COOCH$_2$CH$_2$OC$_4$H$_9$-n | • 71 | — | • 90 | — | • |

TABLE 2-continued

| Example No. | Exemplified compound No. | Phase transition temperature (°C.) | | | | |
|---|---|---|---|---|---|---|
| | | C | $S_C$ | $S_A$ | N | I |
| 95 | 248 — naphthalene-based structure with n-$C_{10}H_{21}O$ and $COOCH_2CH_2OC_6H_{13}$-n | · 72 | — | · 86 | — | · |
| 96 | 249 — naphthalene-based structure with n-$C_{12}H_{25}O$ and $COOCH_2CH_2OC_6H_{13}$-n | · 74 | — | · 87 | — | · |
| 97 | 257 — naphthalene-based structure with n-$C_{10}H_{21}O$ and $COO(CH_2CH_2O)_2C_6H_{13}$-n | · 60 | — | · (57) | — | · |
| 98 | 258 — naphthalene-based structure with n-$C_{12}H_{25}O$ and $COO(CH_2CH_2O)_2C_6H_{13}$-n | · 65 | — | · (60) | — | · |
| 99 | 306 — naphthalene-biphenyl structure with n-$C_{10}H_{21}O$ and $COOCH_2CH(CH_3)_2$ | · 112 | · 164 | · 243 | — | · |
| 100 | 308 — naphthalene-fluorobiphenyl structure with n-$C_{10}H_{21}O$ and $COOCH_2CH(CH_3)_2$ | · 105 | · 143 | · 225 | — | · |

TABLE 2-continued

| Example No. | Exemplified compound No. | Phase transition temperature (°C.) | | | | |
|---|---|---|---|---|---|---|
| | | C | S_C | S_A | N | I |
| 101 | 309 | · 117 | · 186 | · 231 | — | · |
| 102 | 310 | · 102 | · 151 | · 218 | — | · |
| 103 | 316 | · 117 | · 186 | · 227 | — | · |
| 104 | 318 | · 76 | · 162 | · 204 | — | · |
| 105 | 323 | · 134 | · 181 | · 212 | — | · |
| 106 | 335 | · 111 | · 139 | · 204 | — | · |

TABLE 2-continued

| Example No. | Exemplified compound No. | Phase transition temperature (°C.) | | | | |
|---|---|---|---|---|---|---|
| | | C | S_C | S_A | N | I |
| 107 | 340 (n-C_6H_13(OCH_2CH_2)_2O-[naphthalene]-COO-[phenyl]-[phenyl]-COO(CH_2)_2CH(CH_3)_2) | · 71 | · 132 | · 180 | — | · |
| 108 | 345 (n-C_6H_13OCH_2CH_2O-[naphthalene]-COO-[phenyl]-[phenyl]-COOCH_2CH(C_2H_5)_2) | · 74 | · 135 | · 178 | — | · |
| 109 | 346 (n-C_6H_13(OCH_2CH_2)_2O-[naphthalene]-COO-[phenyl]-[phenyl]-COOCH_2CH(C_2H_5)_2) | · 32 | · 111 | · 152 | — | · |
| 110 | 363 (n-C_10H_21O-[naphthalene]-COO-[phenyl]-[phenyl]-COO(CH_2CH_2O)_3C_4H_9-n) | · 109 | · 119 | · 170 | — | · |
| 111 | 364 (n-C_12H_25O-[naphthalene]-COO-[phenyl]-[phenyl]-COO(CH_2CH_2O)_3C_4H_9-n) | · 91 | · 120 | · 156 | — | · |
| 112 | 403 (n-C_12H_25O-[naphthalene]-COO-[naphthalene]-COO(CH_2)_2CH(CH_3)_2) | · 90 | · 116 | · 148 | — | · |

TABLE 2-continued

| Example No. | Exemplified compound No. | | C | Phase transition temperature (°C) $S_C$ | $S_A$ | N | I |
|---|---|---|---|---|---|---|---|
| | | | | | | | |
| 113 | 460 | n-C$_{10}$H$_{21}$O—[pyridine]—COO—[naphthalene]—COOCH$_2$CH(CH$_3$)$_2$ | • 111 | — | — | — | • |
| 114 | 521 | n-C$_5$H$_{11}$—[cyclohexane-H]—COO—[naphthalene]—COO(CH$_2$)$_2$CH(CH$_3$)$_2$ | • 88 | — | — | — | • |

Example 115
Preparation of Liquid Crystal Composition

The following compounds were blended in the ratio shown below and heated at 100° C. to be dissolved, whereby a liquid crystal composition A (ferroelectric liquid crystal composition) was prepared. In the formulas, the mark "*" shows optically active carbon.

Phase transition temperatures (°C.):

I→S$_A$→Sc*→C 84   54   0° C. or lower

Composition A

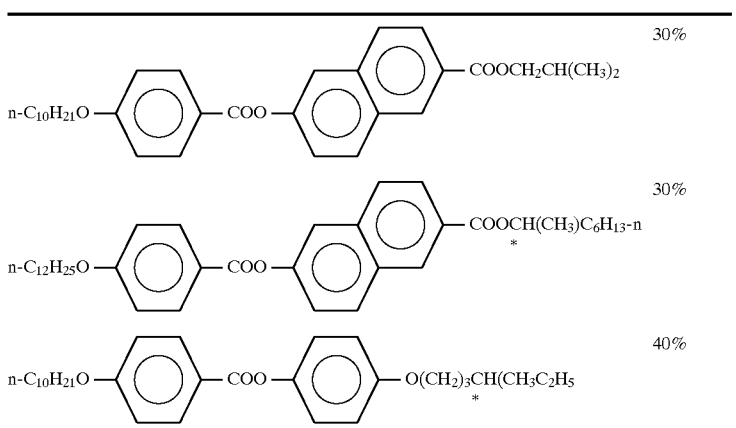

Preparation of Liquid Crystal Element

Figure 2:
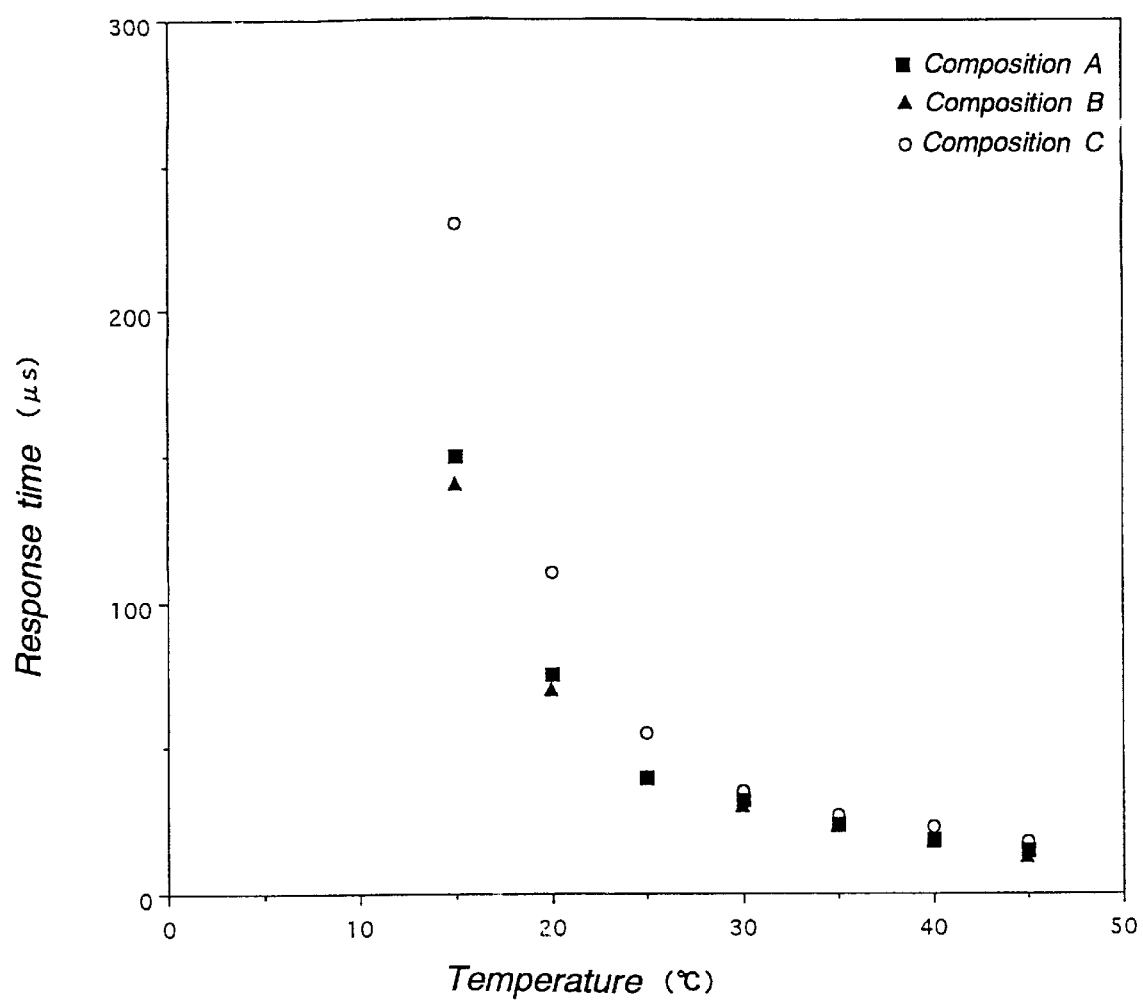
FIG. 2 is a graph showing the temperature dependency of the response time of the liquid crystal compositions of Examples 115 and 116 and the comparative example.

Transparent electrodes and insulating orientation controlling layers made of polyimide were provided on two glass plates having a thickness of 0.7 mm, and alumina beads having an average particle diameter of 2 μm were dispersed on one of the glass plates. Then, the glass plates were stuck together with sealant to prepare a cell shown in FIG. 1. This cell was charged with the liquid crystal composition prepared above after heating it to be in an isotropic phase, and the liquid crystal composition was gradually cooled down to be in a ferroelectric liquid crystal phase at a rate of 1° C./minute, whereby a liquid crystal element was prepared. This liquid crystal element was interposed between two polarizing plates disposed in a cross-nicol state, and was applied a voltage of 20 V to detect an optical response (change in a transmitted light quantity: 10 to 90%), whereby the response time was determined. The measured results are shown in FIG. 2.

Example 116
Preparation of Liquid Crystal Composition

The following compounds were blended in the ratio shown below and heated at 100° C. to be dissolved, whereby a liquid crystal composition B (ferroelectric liquid crystal composition) was prepared. In the formulas, the mark "*" shows optically active carbon.

Phase transition temperatures (°C.):

I→S$_A$→Sc*→C 88   60   0° C. or lower

Composition B

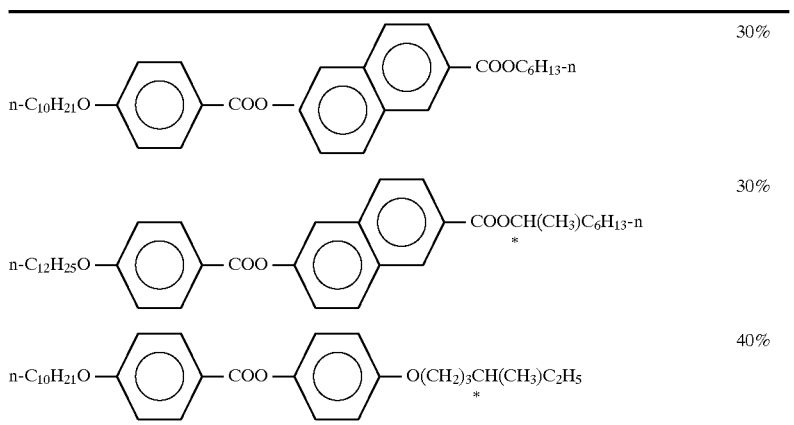

Preparation of Liquid Crystal Element

Transparent electrodes and insulating orientation controlling layers made of polyimide were provided on two glass plates having a thickness of 0.7 mm, and alumina beads having an average particle diameter of 2 μm were dispersed on one of the glass plates. Then, the glass plates were stuck together with sealant to prepare a cell shown in FIG. 1. This cell was charged with the liquid crystal composition prepared above after heating it to be in an isotropic phase, and the liquid crystal composition was gradually cooled down to be in a ferroelectric liquid crystal phase at a rate of 1° C./minute, whereby a liquid crystal element was prepared. This liquid crystal element was interposed between two polarizing plates disposed in a cross-nicol state, and was applied a voltage of 20 V to detect an optical response (change in a transmitted light quantity: 10 to 90%), whereby the response time was determined. The measured results are shown in FIG. 2.

Comparative Example
Preparation of Liquid Crystal Composition

The following compounds were blended in the ratio shown below and heated at 100° C. to be dissolved, whereby a liquid crystal composition C (ferroelectric liquid crystal composition) was prepared. In the formulas, the mark "*" shows optically active carbon.

Phase transition temperatures (°C.):

I→SA→Sc*→C
80 52 0° C. or lower
Composition C

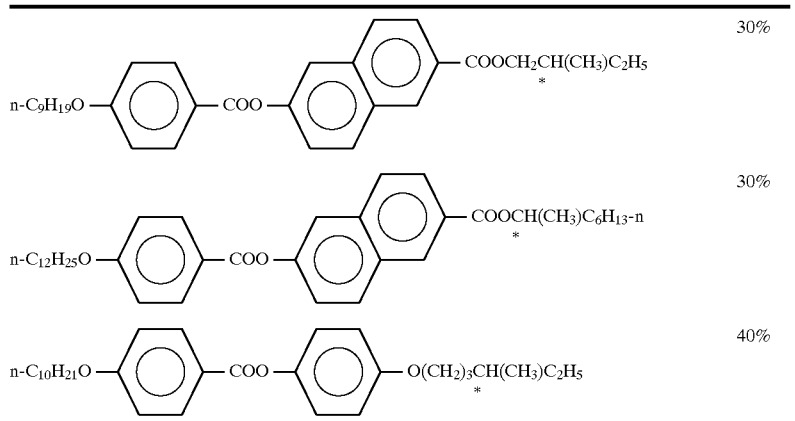

Preparation of Liquid Crystal Element

Transparent electrodes and insulating orientation controlling layers made of polyimide were provided on two glass plates having a thickness of 0.7 mm, and alumina beads having an average particle diameter of 2 μm were dispersed on one of the glass plates. Then, the glass plates were stuck together with sealant to prepare a cell shown in FIG. 1. This cell was charged with the liquid crystal composition prepared above after heating it to be in an isotropic phase, and the liquid crystal composition was gradually cooled down to be in a ferroelectric liquid crystal phase at a rate of 1° C./minute, whereby a liquid crystal element was prepared. This liquid crystal element was interposed between two polarizing plates disposed in a cross-nicol state, and was applied a voltage of 20 V to detect an optical response (change in a transmitted light quantity: 10 to 90%), whereby the response time was determined. The measured results are shown in FIG. 2.

It has been found from the comparison of the examples of the present invention with the comparative example each shown in FIG. 2 that while the response time is 55 μsec at 25° C. in the liquid crystal composition C, it is 40 μsec in the liquid crystal compositions A and B and therefore the response time is shortened. With respect to a variation in the response time at 20°–40° C., while the response time at 20° C. is about five times as long as the response time at 40° C. in the liquid crystal composition C, a variation in the response time is about four times in the liquid crystal compositions A and B. Accordingly, it can be found that the liquid crystal compositions of the present invention have less temperature dependency on the response time.

What is claimed is:

1. A naphthalene compound represented by the following Formula (1):

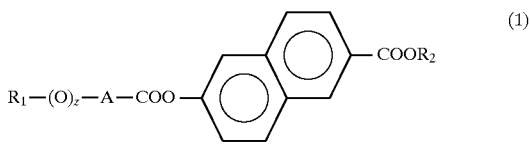

wherein $R_1$ and $R_2$ each represent a linear or branched alkyl group having 1 to 20 carbon atoms, an alkoxyalkyl group having 2 to 20 carbon atoms, or an alkenyl group having 2 to 20 carbon atoms which may be substituted with halogen atoms and have no asymmetric carbon atoms, provided that at least one of $R_1$ and $R_2$ is an alkyl group or alkoxyalkyl group represented by Formulas (II) or (III):

$$—(CH_2)_b CH(C_c H_{2c+1})_2 \qquad (II)$$

$$—C_d H_{2d} O(C_e H_{2e} O)_f C_g H_{2g+1} \qquad (II)$$

wherein b represents a natural number of 0 to 17, c represents a natural number of 1 to 9, d represents a natural number of 1 to 10, e represents a natural number of 1 to 10, f represents a natural number of 0 to 5, and g represents a natural number of 1 to 12, provided that b+c×2≦19 and d+e×f+g≦20; A represents any of the groups represented by the following formulas:

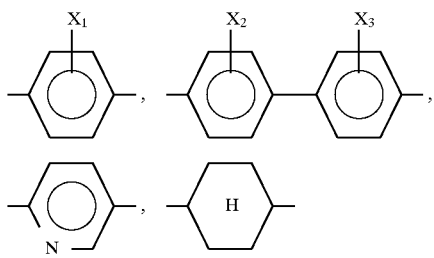

wherein $X_1$, $X_2$, and $X_3$ each represent a hydrogen atom or a halogen atom, and when A is a 1,4-cyclohexylene ring, it is disposed in a trans position; and z represents 0 or 1.

2. A naphthalene compound as described in claim 1, wherein A is any of the groups represented by the following formulas:

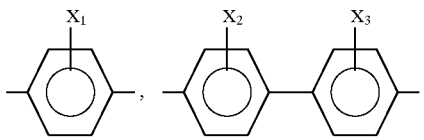

wherein $X_1$, $X_2$, and $X_3$ each represent a hydrogen atom or a halogen atom.

3. A liquid crystal composition containing at least one naphthalene compound as described in claim 1.

4. A liquid crystal element comprising the liquid crystal composition as described in claim 3 disposed between a pair of electrode substrates.

5. A naphthalene compound represented by the following Formula (1):

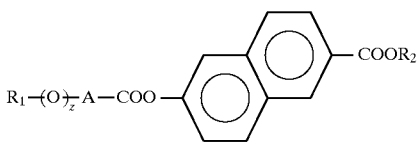

wherein $R_1$, and $R_2$ each represent a linear or branched alkyl group having 1 to 20 carbon atoms, an alkoxyalkyl group having 2 to 20 carbon atoms, or an alkenyl group having 2 to 20 carbon atoms which may be substituted with halogen atoms and have no asymmetric carbon atoms, provided that at least one of $R_1$ and $R_2$ is a halogenated alkyl group represented by Formulas (IV), (V), or (VI):

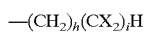      (IV)

      (V)

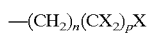      (VI)

wherein X represents a halogen atom, h represents a natural number of 0 to 19, i represents a natural number of 1 to 20, j represents a natural number of 0 to 18, k represents a natural number of 1 to 10, l represents a natural number of 1 to 19, and m represents a natural number of 1 to 19, n represents a natural number of 0 to 19, p represents a natural number of 1 to 20, provided that $h+i \leq 20$, $j+k\times l+m \leq 20$ and $n+p \leq 20$; A represents any of the groups represented by the following formulas:

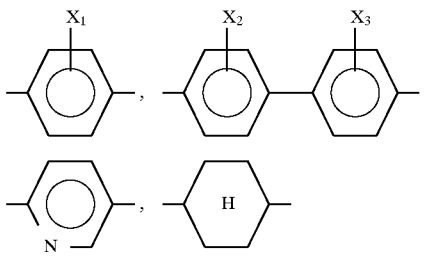

wherein $X_1$, $X_2$, and $X_3$ each represent a hydrogen atom or a halogen atom, and when A is a 1,4-cyclohexylene ring, it is disposed in a trans position; and z represents 0 or 1.

6. A naphthalene compound as described in claim 5, wherein either of $R_1$ and $R_2$ is a halogenated alkyl group represented by Formulas (IV), (V) or (VI):

      (IV)

      (V)

      (VI)

wherein X represents a halogen atom; h represents a natural number of 0 to 19; i represents a natural number of 1 to 20; j represents a natural number of 0 to 18; k represents a natural number of 1 to 10; l represents a natural number of 1 to 19; and m represents a natural number of 1 to 19; n represents a natural number of 0 to 19; p represents a natural number of 1 to 20, provided that $h+i \leq 20$, $j+k\times l+m \leq 20$ and $n+p \leq 20$, and the other is an alkyl group or alkoxyalkyl group represented by Formulas (I), (II) or (III):

      (I)

      (II)

      (III)

wherein a represents a natural number of 1 to 20; b represents a natural number of 0 to 17; c represents a natural number of 1 to 9; d represents a natural number of 1 to 10; e represents a natural number of 1 to 10; f represents a natural number of 0 to 5; and g represents a natural number of 1 to 12, provided that $b+c\times 2 \leq 19$ and $d+e\times f+g \leq 20$.

7. A naphthalene compound as described in claim 6, wherein A is any of the groups represented by the following formulas:

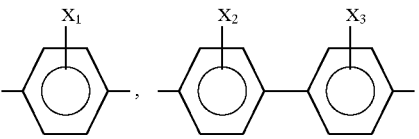

wherein $X_1$, $X_2$, and $X_3$ each represent a hydrogen atom or a halogen atom.

8. A naphthalene compound as described in claim 5, wherein A is any of the groups represented by the following formulas:

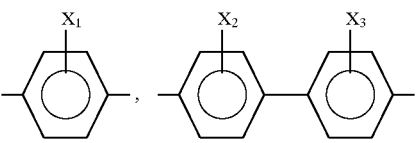

wherein $X_1$, $X_2$, and $X_3$ each represent a hydrogen atom or a halogen atom.

9. A liquid crystal composition containing at least one naphthalene compound as described in claim 5.

10. A liquid crystal element comprising the liquid crystal composition as described in claim 9 disposed between a pair of electrode substrates.

11. A naphthalene compound represented by the following Formula (2):

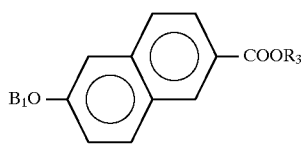

(2)

wherein $R_3$ represents a branched alkyl group having 3 to 20 carbon atoms which have no asymmetric carbon atoms, or a linear or branched halogenated alkyl group having 1 to 20 carbon atoms, or an alkoxyalkyl group having 2 to 20 carbon atoms or an alkenyl group having 2 to 20 carbon atoms which may be substituted with halogen atoms and have no asymmetric carbon atoms; and $B_1$ represents a hydrogen atom or a benzyl group.

* * * * *